United States Patent [19]

Ihle et al.

[11] Patent Number: 5,728,536
[45] Date of Patent: Mar. 17, 1998

[54] JAK KINASES AND REGULATION OF CYTOKINE SIGNAL TRANSDUCTION

[75] Inventors: James N. Ihle; Bruce A. Witthuhn, both of Memphis; Frederick W. Quelle, Cordova, all of Tenn.; Ollie Silvennoinen, New York, N.Y.

[73] Assignee: St. Jude Children's Research Hospital, Memphis, Tenn.

[21] Appl. No.: 97,997

[22] Filed: Jul. 29, 1994

[51] Int. Cl.$^6$ .................. G01N 33/567; G01N 33/573; G01N 33/53; G01N 33/543
[52] U.S. Cl. .................. 435/7.21; 435/7.4; 435/7.72; 436/518
[58] Field of Search .................. 435/7.21, 7.4, 435/7.72; 436/518

[56] References Cited

U.S. PATENT DOCUMENTS 5,441,868  8/1995  Lin .................................. 435/69.4
5,470,952  11/1995  Stahl et al. ........................ 530/350

FOREIGN PATENT DOCUMENTS

WO 92/10519  6/1992  WIPO .

OTHER PUBLICATIONS

Nakajima et al., Interleukin–6 Signals Activating junB and Tls1 1 Gene Transcription in a B–Cell Hybridoma, Molecule and Cellular Biology 11(3):1409–1418, 1991.
Bird, T. et al., "Evidence That MAP (Mitogen–Activated Protein) Kinase Activation May Be A Necessary But Not Sufficient Signal For A Restricted Subset Of Responses In IL–1–Treated Epidermoid Cells," *Cytokine* 4(6):429–440 (Nov. 1993).
Campbell, G.S. et al., "Evidence for Involvement of the Growth Hormone Receptor–associated Tyrosine Kinase in Actions of Growth Hormone," *J. Biol. Chem.* 268 (10):7427–7434 (Apr. 5, 1993).
Carroll, M.P. et al., "Interleukin–3 and Granulocyte–Macrophage Colony–stimulating Factor Mediate Rapid Phosphorylation and activation of Cytosolic c–raf," *J. Biol. Chem.* 265 (32):19812–19817 (Nov. 15, 1990).
Carroll, M.P. et al., "Erythropoietin Induces Raf–1 Activation and Raf–1 Is Required for Erythropoietin–mediated Proliferation," *J. Biol. Chem.* 266 (23):14964–14969 (Aug. 15, 1991).
Cleveland, J.L. et al., "Tyrosine Kinase Oncogenes Abrogate Interleukin–3 Dependence of Murine Myeloid Cells through Signaling Pathways Involving c–myc: Conditional Regulation of c–myc Transcription by Temperature–Sensitive v–abl," *Mol. and Cell. Biol.* 9 (12):5685–5695 (Dec. 1989).
Dusanter–Fourt, I. et al., "Erythropoietin Induces the Tyrosine Phosphorylation of Its Own Receptor in Human Erythropoietin–responsive Cells," *J. Biol. Chem.* 267 (15):10670–10675 (May 25, 1992).
Edgington, S.M., "Molecular Crosstalk: Will virology and growth–factor research aid cytokine drug discovery?" *Bio/Technol.* 11:465–468 (Apr. 1993).

Firmbach–Kraft, I. et al., "tyk2, prototype of a novel class of non–receptor tyrosine kinase genes," *Oncogene* 5:1329–1336 (3 May 1990).
Fu, X.–Y., "A Transcription Factor with SH2 and SH3 Domains Is Directly Activated by an Interferon α–Induced Cytoplasmic Protein Tyrosine Kinase(s)," *Cell* 70:323–335 (Jul. 24, 1992).
Fung, M.R. et al., "A Tyrosine Kinase Physically Associates With The β–Subunit Of The Human IL–2 Receptor," *J. Immunol.* 147 (4):1253–1260 (Aug. 15, 1991).
Hanks, S.K. et al., "The Protein Kinase Family: Conserved Features and Deduced Phytogeny of the Catalytic Domains," *Science* 241:42–52 (1 Jul. 1988).
Harpur, A.G. et al., "JAK2, a third member of the JAK family of protein tyrosine kinases," *Oncogene* 7:1347–1353 (1992).
Howard, O.M.Z. et al., "Characterization of a class 3 tyrosine kinase," *Oncogene* 7:895–900 (1992).
Hunter, T., "A Thousand and One Protein Kinases," *Cell* 50:823–829 (Sep. 11, 1987).
Ihle, J.N., "Interleukin–3 and Hematopoiesis," *Interleukins: Mol. Biol. and Immunol.* 51:65–106.
Kishimoto, T. (ed.) Basel, Karger (1992).
Isfort, R.J. et al., "Interleukin 3 binds to a 140–kDa phosphotyrosine–containing cell surface protein," *Proc. Natl. Acad. Sci. USA* 85:7982–7986 (Nov. 1988).
Koch, C.A. et al., "SH2 and SH3 Domains: Elements That Control Interactions of Cytoplasmic Signaling Proteins," *Science* 252:668–674 (3 May 1991).
Linnekin, D. et al., "Signal transduction of human interleukin 3 and granulocyte–macrophage colony–stimulating factor through serine and tyrosine phosphorylation," *J. Biochem* 271:317–324 (1990).
Linnekin, D. et al., "Association of the erythropoietin receptor with protein tyrosine kinase activity," *Proc. Natl. Acad. Sci. USA* 89:6237–6241 (Jul. 1992).

(List continued on next page.)

*Primary Examiner*—Marian C. Knode
*Assistant Examiner*—Donna C. Wortman
*Attorney, Agent, or Firm*—Sterne, Kessler, Goldstein & Fox P.L.L.C.

[57] ABSTRACT

The present invention is based on the discovery that a critical step in the cellular response to several cytokines is the activation (i.e. tyrosine phosphorylation) of a member of the Jak kinase family. In particular, several cytokines whose activity is mediated by the activation of Jak2 kinase are identified. The present invention provides novel methods for regulating the cellular response to these cytokines by inhibiting or enhancing the Jak kinase activity which mediates the response. Assays for identifying inhibitors of Jak kinase activity or cytokine-induced Jak kinase activation useful in the methods of the invention are also provided. Antibodies raised against peptide fragments of Jak1, Jak2, and Tyk2 kinase capable of specifically binding to these Jak kinases without interfering with kinase activity are also provided. In addition, the complete DNA coding sequence and amino acid structure of Jak2 kinase is provided by the invention.

4 Claims, 23 Drawing Sheets

OTHER PUBLICATIONS

Mano, H. et al., "Expression of a novel form of Tec kinase in hematopoietic cells and mapping of the gene to chromosome 5 near Kit," *Oncogene* 8:417–424 (1993).

Metcalf, D., "The molecular control of cell division, differentiation commitment and maturation in haemopietic cells," *Nature* 339:27–30 (4 May 1989).

Miura, O. et al., "Induction of Tyrosine Phosphorylation by the Erythropoietin Receptor Correlates with Mitogenesis," *Mol. and Cell. Biol.* 11 (10):4895–4902 (Oct. 1991).

Miyajima, A. et al., "Cytokine Receptors and Signal Transduction," *Annu. Rev. Immunol.* 10:295–331 (1992).

Morla, A.O. et al., "Hematopoietic Growth Factors Activate the Tyrosine Phosphorylation of Distinct Sets of Proteins in Interleukin-3-Dependent Murine Cell Lines," *Mol. and Cell. Biol.* 8(5):2214–2218 (May 1988).

Partanen, J. et al., "Putative tyrosine kinases expressed in K-562 human Leukemia cells," *Proc. Natl. Acad. Sci. USA* 87:8913–8917 (Nov. 1990).

Pellegrini, S. et al., "Use of a Selectable Marker Regulated by Alpha Interferon To Obtain Mutations in the Signaling Pathway," *Mol. and Cell. Biol.* 9(11):4605–4612 (Nov. 1989).

Pritchard, M.A. et al., "Two members of the JAK family of protein tyrosine kinases map to Chromosomes 1p31.3 and 9p24," *Mammalian Genome* 3:36–38 (1992).

Quelle, F.W. et al., "Proliferative Action of Erythropoietin Is Associated with Rapid Protein Tyrosine Phosphorylation in Responsive B6SUtEP Cells," *J. Biol. Chem.* 266 (1):609–614 (Jan. 5, 1991).

Schindler, C. et al., "Interferon-Dependent Tyresine Phosphorytation of a Latent Cytoplasmic Transcription Factor," *Science* 257:809–813 (7 Aug. 1992).

Shuai, K. et al., "Activation of Transcription by IFN-γ: Tyrosine Phosphorylation of a 91-kD DNA Binding Protein," *Science* 258:1808–1812 (11 Dec. 1992).

Sorensen, P. et al., "Interleukin-3 Stimulates the Tyrosine Phosphorylation of the 140-Kilodalton Interteukin-3 Receptor," *J. Biol. Chem.* 264 (32):19253–19258 (Nov. 15, 1989).

Spangler, R. et al., "Erythropoietin Increases c-myc mRNA by a Protein Kinase C-dependent Pathway," *J. Biol. Chem.* 266 (2):681–684 (Jan. 15, 1991).

Torigoe, T. et al., "Interleukin-3 Regulates the Activity of the LYN Protein-Tyrosine Kinase in Myeloid Committed Leukemic Cell Lines," *Blood* 80 (3):617–624 (Aug. 1, 1992).

Turner, B. et al., "Interleukin 2 induces tyrosine phosphorylation and activation of p72–74 Raf–1 kinase in a T–cell line," *Proc. Natl. Acad. Sci USA* 88:1227–1231 (Feb. 1991).

Uttrich, A. et al., "Signal Transduction by Receptors with Tyrosine Kinase Activity," *Cell* 61:203–212 (Apr. 20, 1990).

Valezquez, L. et al., "A Protein Tyrosine Kinase in the Interferon α/β Signaling Pathway," *Cell* 70:313–322 (Jul. 24, 1992).

Wang, X. et al., "Growth Hormone-promoted Tyrosyl Phosphorytation of a 121–kDa Growth Hormone Receptor-associated Protein," *J. Biol. Chem.* 268 (5):3573–3579 (Feb. 15, 1993).

Wilks, A.F., "Two putative protein–tyrosine kinases identified by application of the polymerase chain reaction," *Proc. Natl. Acad. Sci. USA* 86:1603–1607 (Mar. 1989).

Wilks, A.F., "Structure And Function Of The Protein Tyrosine Kinases," *Prog. in Growth Factor Res.* 2:97–111 (1990).

Wilks, A.F., "Cloning Members of Protein–Tyrosine Kinase Family Using Polymerase Chain Reaction," *Meth. in Enzylmol.* 200:533–546 (1991).

Wilks, A. et al., "Two Novel Protein–Tyrosine Kinases, Each with a Second Phosphotransferase-Related Catalytic Domain, Define a New Class of Protein Kinase," *Mol. and Cell. Biol.* 11 (4):2057–2065 (Apr. 1991).

Yarden, Y. et al., "Growth Factor Receptor Tyrosine Kinases," *Ann. Rev. Biochem.* 57:443–478 (1988).

Yoshimura, A. et al., "Point mutation in the exoplasmic domain of the erythropoietin receptor resulting in hormone-independent activation and tumorigenicity," *Nature* 348:647–649 (Dec. 1990).

Yoshimura, A. et al., "In Vitro Phosphorylation of the Erythropoietin Receptor and an Associated Protein, p. 130," *Mol. and Cell. Biol.* 12 (2):706–715 (Feb. 1992).

```
CGGGGGAACA AGATGTGAAC TGTTTTCCCT CCCCAGAAGA AGAGGCCCTT TTTTTCCCTC        60

CCGCGAAGGC CAATGTTCTG AAAAAAGCTC TAG ATG GGA ATG GCC TGC CTT ACA       114
                                    Met Gly Met Ala Cys Leu Thr
                                     1                   5

ATG ACA GAA ATG GAG GCA ACC TCC ACA TCT CCT GTA CAT CAG AAT GGT        162
Met Thr Glu Met Glu Ala Thr Ser Thr Ser Pro Val His Gln Asn Gly
         10              15              20

GAT ATT CCT GGA AGT GCT AAT TCT GTG AAG CAG ATA GAG CCA GTC CTT        210
Asp Ile Pro Gly Ser Ala Asn Ser Val Lys Gln Ile Glu Pro Val Leu
 25              30              35

CAA GTG TAT CTG TAC CAT TCT CTT GGG CAA GCT GAA GGA GAG TAT CTG        258
Gln Val Tyr Leu Tyr His Ser Leu Gly Gln Ala Glu Gly Glu Tyr Leu
 40              45              50              55

AAG TTT CCA AGT GGA GAG TAT GTT GCA GAA GAA ATT TGT GTG GCT GCT        306
Lys Phe Pro Ser Gly Glu Tyr Val Ala Glu Glu Ile Cys Val Ala Ala
                 60              65              70

TCT AAA GCT TGT GGT ATT ACG CCT GTG TAT CAT AAT ATG TTT GCG TTA        354
Ser Lys Ala Cys Gly Ile Thr Pro Val Tyr His Asn Met Phe Ala Leu
         75              80              85

ATG AGT GAA ACC GAA AGG ATC TGG TAC CCA CCC AAT CAT GTC TTC CAC        402
Met Ser Glu Thr Glu Arg Ile Trp Tyr Pro Pro Asn His Val Phe His
         90              95             100

ATA GAC GAG TCA ACC AGG CAT GAC ATA CTC TAC AGG ATA AGG TTC TAC        450
Ile Asp Glu Ser Thr Arg His Asp Ile Leu Tyr Arg Ile Arg Phe Tyr
        105             110             115

TTC CCT CAT TGG TAC TGT AGT GGC AGC AGC AGA ACC TAC AGA TAC GGA        498
Phe Pro His Trp Tyr Cys Ser Gly Ser Ser Arg Thr Tyr Arg Tyr Gly
120             125             130             135
                         >
GTG TCC CGT GGG GCT GAA GCT CCT CTG CTT GAT GAC TTT GTC ATG TCT        546
Val Ser Arg Gly Ala Glu Ala Pro Leu Leu Asp Asp Phe Val Met Ser
                140             145             150
```

FIG.1A

```
        cc  c
TAC CTT TTT GCT CAG TGG CGG CAT GAT TTT GTT CAC GGA TGG ATA AAA      594
Tyr Leu Phe Ala Gln Trp Arg His Asp Phe Val His Gly Trp Ile Lys
        S   P                   160             165
            155

GTA CCT GTG ACT CAT GAA ACT CAG GAA GAG TGT CTT GGG ATG GCG GTG      642
Val Pro Val Thr His Glu Thr Gln Glu Glu Cys Leu Gly Met Ala Val
            170             175             180

TTA GAC ATG ATG AGA ATA GCT AAG GAG AAA GAC CAG ACT CCA CTG GCT      690
Leu Asp Met Met Arg Ile Ala Lys Glu Lys Asp Gln Thr Pro Leu Ala
            185             190             195

GTC TAT AAC TCT GTC AGC TAC AAG ACA TTC TTA CCA AAG TGC GTT CGA      738
Val Tyr Asn Ser Val Ser Tyr Lys Thr Phe Leu Pro Lys Cys Val Arg
200             205             210             215

GCG AAG ATC CAA GAC TAT CAC ATT TTA ACC CGG AAG CGA ATC AGG TAC      786
Ala Lys Ile Gln Asp Tyr His Ile Leu Thr Arg Lys Arg Ile Arg Tyr
                220             225             230

AGA TTT CGC AGA TTC ATT CAG CAA TTC AGT CAA TGT AAA GCC ACT GCC      834
Arg Phe Arg Arg Phe Ile Gln Gln Phe Ser Gln Cys Lys Ala Thr Ala
                235             240             245

AGG AAC CTA AAA CTT AAG TAT CTT ATA AAC CTG GAA ACC CTG CAG TCT      882
Arg Asn Leu Lys Leu Lys Tyr Leu Ile Asn Leu Glu Thr Leu Gln Ser
            250             255             260

GCC TTC TAC ACA GAA CAG TTT GAA GTA AAA GAA TCT GCA AGA GGT CCT      930
Ala Phe Tyr Thr Glu Gln Phe Glu Val Lys Glu Ser Ala Arg Gly Pro
    265             270             275

TCA GGT GAG GAG ATT TTT GCA ACC ATT ATA ATA ACT GGA AAC GGT GGA      978
Ser Gly Glu Glu Ile Phe Ala Thr Ile Ile Ile Thr Gly Asn Gly Gly
280             285             290             295

ATT CAG TGG TCA AGA GGG AAA CAT AAG GAA AGT GAG ACA CTC ACA GAA     1026
Ile Gln Trp Ser Arg Gly Lys His Lys Glu Ser Glu Thr Leu Thr Glu
                300             305             310
```

FIG.1B

```
                                                                    t                                c             g              g   c
CAG GAC GTA CAG TTA TAT TGT GAT TTC CCT GAT ATT ATT GAT GTC AGT     ATT AAG CAA GCA AAC CAG GAA TGC TCA AAT GAA AGT AGA ATT GTA ACT     1074
Gln Asp Val Gln Leu Tyr Cys Asp Phe Pro Asp Ile Ile Asp Val Ser     Ile Lys Gln Ala Asn Gln Glu Cys Ser Asn Glu Ser Arg Ile Val Thr     1122
        315                 320                 325                         330                  335    T         340 V
``` c   g g   c g g   c
GTC CAT AAA CAA GAT GGT AAA GTT TTG GAG ATA GAA CTT AGC TCA TTA     1170
Val His Lys Gln Asp Gly Lys Val Leu Glu Ile Glu Leu Ser Ser Leu
        345                 350                 355 t            g
AAA GAA GCC TTG TCA TTC GTG TCA TTA ATT GAC GGG TAT TAC AGA CTA     1218
Lys Glu Ala Leu Ser Phe Val Ser Leu Ile Asp Gly Tyr Tyr Arg Leu
360                  365                 370                 375 g                      t              t       c
ACT GCG GAT GCG CAC CAT TAC CTC TGC AAA GAG GTG GCT CCC CCA GCT    1266
Thr Ala Asp Ala His His Tyr Leu Cys Lys Glu Val Ala Pro Pro Ala
                    380                 385                 390 t  q                        t                 t
GTG CTC GAG AAC ATA CAC AGC AAC TGC CAC GGC CCA ATA TCA ATG GAT    1314
Val Leu Glu Asn Ile His Ser Asn Cys His Gly Pro Ile Ser Met Asp
                395                 400                 405 c                              a  a                    g
TTT GCC ATT AGC AAA CTA AAG AAG GCG GGT AAC CAG ACT GGA CTA TAT    1362
Phe Ala Ile Ser Lys Leu Lys Lys Ala Gly Asn Gln Thr Gly Leu Tyr
                410                 415                 420 q   t   t                                 c
GTG CTA CGA TGC AGC CCT AAG GAC TTC AAC AAA TAC TTT CTG ACC TTT    1410
Val Leu Arg Cys Ser Pro Lys Asp Phe Asn Lys Tyr Phe Leu Thr Phe
        425                 430                 435 c                       t                                   q
GCT GTT GAG CGA GAA AAT GTC ATT GAA TAT AAA CAC TGT TTG ATT ACG    1458
Ala Val Glu Arg Glu Asn Val Ile Glu Tyr Lys His Cys Leu Ile Thr
440                 445                 450                 455 g             t
AAG AAT GAG AAT GGA GAA TAC AAC CTC AGC GGG ACT AAG AGG AAC TTC    1506
Lys Asn Glu Asn Gly Glu Tyr Asn Leu Ser Gly Thr Lys Arg Asn Phe
                460                 465                 470

FIG.1C

```
                gt
AGT AAC CTT AAG GAC CTT TTG AAT TGC TAC CAG ATG GAA ACT GTG CGC    1554
Ser Asn Leu Lys Asp Leu Leu Asn Cys Tyr Gln Met Glu Thr Val Arg
     S      475             480             485 c                       t   t           g
TCA GAC AGT ATC ATC TTC CAG TTT ACC AAA TGC TGC CCC CCA AAG CCA    1602
Ser Asp Ser Ile Ile Phe Gln Phe Thr Lys Cys Cys Pro Pro Lys Pro
         490             495             500 t                       g
AAA GAT AAA TCA AAC CTT CTC GTC TTC AGA ACA AAT GGT ATT TCT GAT    1650
Lys Asp Lys Ser Asn Leu Leu Val Phe Arg Thr Asn Gly Ile Ser Asp
     505             510             515    V c
GTT CAG ATC TCA CCA ACA TTA CAG AGG CAT AAT AAT GTG AAT CAA ATG    1698
Val Gln Ile Ser Pro Thr Leu Gln Arg His Asn Asn Val Asn Gln Met
520      L       525             530             535 g                       c
GTG TTT CAC AAA ATC AGG AAT GAA GAT TTA ATA TTT AAT GAA AGT CTT    1746
Val Phe His Lys Ile Arg Asn Glu Asp Leu Ile Phe Asn Glu Ser Leu
             540             545             550 c                   a
GGC CAA GGT ACT TTT ACA AAA ATT TTT AAA GGT GTA AGA AGA GAA GTT    1794
Gly Gln Gly Thr Phe Thr Lys Ile Phe Lys Gly Val Arg Arg Glu Val
             555             560             565 g       g   c
GGA GAT TAT GGT CAA CTG CAC AAA ACG GAA GTT CTT TTG AAA GTC CTA    1842
Gly Asp Tyr Gly Gln Leu His Lys Thr Glu Val Leu Leu Lys Val Leu
         570             K               580
                         575 a                           t
GAT AAA GCA CAT AGG AAC TAT TCA GAG TCT TTC TTC GAA GCA GCA AGC    1890
Asp Lys Ala His Arg Asn Tyr Ser Glu Ser Phe Phe Glu Ala Ala Ser
         585             590             595 a   a
ATG ATG AGT CAG CTT TCT CAC AAG CAT TTG GTT TTG AAT TAT GGT GTC    1938
Met Met Ser Gln Leu Ser His Lys His Leu Val Leu Asn Tyr Gly Val
600             605             610             615 t           g
TGT GTC TGT GGA GAG GAG AAC ATT CTG GTT CAA GAA TTT GTA AAA TTT    1986
Cys Val Cys Gly Glu Glu Asn Ile Leu Val Gln Glu Phe Val Lys Phe
             620             625             630
```

FIG.1D

```
                              t
GGA TCA CTG GAT ACA TAC CTG AAG AAG AAC AAA AAT TCC ATA AAT ATA        2034
Gly Ser Leu Asp Thr Tyr Leu Lys Lys Asn Lys Asn Ser Ile Asn Ile
        635                 640                 645
                    g                                   c   c
TTA TGG AAA CTT GGA GTG GCT AAG CAG TTG GCA TGG GCC ATG CAT TTT        2082
Leu Trp Lys Leu Gly Val Ala Lys Gln Leu Ala Trp Ala Met His Phe
        650                 655                 660

CTA GAA GAA AAA TCC CTT ATT CAT GGG AAT GTG TGT GCT AAA AAT ATC        2130
Leu Glu Glu Lys Ser Leu Ile His Gly Asn Val Cys Ala Lys Asn Ile
        665                 670                 675

CTG CTT ATC AGA GAA GAA GAC AGG AGA ACC GGG AAC CCA CCT TTC ATC        2178
Leu Leu Ile Arg Glu Glu Asp Arg Arg Thr Gly Asn Pro Pro Phe Ile
680                 685                 690                 695

AAA CTT AGT GAT CCT GGC ATT AGC ATT ACA GTT CTA CCG AAG GAC ATT        2226
Lys Leu Ser Asp Pro Gly Ile Ser Ile Thr Val Leu Pro Lys Asp Ile
                700                 705                 710
                                a   g
CTT CAG GAG AGA ATA CCA TGG GTA CCT CCT GAA TGC ATT GAG AAT CCT        2274
Leu Gln Glu Arg Ile Pro Trp Val Pro Pro Glu Cys Ile Glu Asn Pro
            715 T               720                 725
    a   c
AAA AAT CTC AAT CTG GCA ACA GAC AAG TGG AGC TTC GGG ACC ACT CTG        2322
Lys Asn Leu Asn Leu Ala Thr Asp Lys Trp Ser Phe Gly Thr Thr Leu
        730 T               735                 740

TGG GAG ATC TGC AGT GGA GGA GAT AAG CCC CTG AGT GCT CTG GAT TCT        2370
Trp Glu Ile Cys Ser Gly Gly Asp Lys Pro Leu Ser Ala Leu Asp Ser
        745                 750                 755

CAA AGA AAG CTG CAG TTC TAT GAA GAT AAG CAT CAG CTT CCT GCA CCC        2418
Gln Arg Lys Leu Gln Phe Tyr Glu Asp Lys His Gln Leu Pro Ala Pro
760                 765                 770                 775
```

FIG.1E

```
                          g
AAG TGG ACA GAG TTA GCA AAC CTT ATA AAT AAT TGC ATG GAC TAT GAG      2466
Lys Trp Thr Glu Leu Ala Asn Leu Ile Asn Asn Cys Met Asp Tyr Glu
                780             785             790

CCA GAT TTC AGG CCT GCT TTC ACA GCT GTC ATC CGT GAT CTT AAC AGC      2514
Pro Asp Phe Arg Pro Ala Phe Arg Ala Val Ile Arg Asp Leu Asn Ser
                795             800             805

CTG TTT ACT CCA GAT TAT GAA CTA CTA ACA GAA AAT GAC ATG CTA CCA      2562
Leu Phe Thr Pro Asp Tyr Glu Leu Leu Thr Glu Asn Asp Met Leu Pro
            810             815             820

AAC ATG AGA ATA GGT GCC CTA GGG TTT TCT GGT GCT TTT GAA GAC AGG      2610
Asn Met Arg Ile Gly Ala Leu Gly Phe Ser Gly Ala Phe Glu Asp Arg
            825             830             835

GAC CCT ACA CAG TTT GAA GAG AGA CAC TTG AAG TTT CTA CAG CAG CTT      2658
Asp Pro Thr Gln Phe Glu Glu Arg His Leu Lys Phe Leu Gln Gln Leu
        840             845             850             855

GGC AAA GGT AAC TTC GGG AGT GTG GAG ATG TGC CGC TAT GAC CCG CTG      2706
Gly Lys Gly Asn Phe Gly Ser Val Glu Met Cys Arg Tyr Asp Pro Leu
                860             865             870

CAG GAC AAC ACT GGC GAG GTG GTC GCT GTG AAG AAA CTC CAG CAC AGC      2754
Gln Asp Asn Thr Gly Glu Val Val Ala Val Lys Lys Leu Gln His Ser
            875             880             885

ACT GAA GAG CAC CTC CGA GAC TTT GAG AGG GAG ATC GAG ATC CTG AAA      2802
Thr Glu Glu His Leu Arg Asp Phe Glu Arg Glu Ile Glu Ile Leu Lys
            890             895             900

TCC TTG CAG CAT GAC AAC ATC GTC AAG TAC AAG GGA GTG TGC TAC AGT      2850
Ser Leu Gln His Asp Asn Ile Val Lys Tyr Lys Gly Val Cys Tyr Ser
            905             910             915

GCG GGT CGG CGC AAC CTA AGA TTA ATT ATG GAA TAT TTA CCA TAT GGA      2898
Ala Gly Arg Arg Asn Leu Arg Leu Ile Met Glu Tyr Leu Pro Tyr Gly
920             925             930             935
```

FIG.1F

```
AGT TTA CGA GAC TAT CTC CAA AAA CAT AAA GAA CGG ATA GAT CAC AAA         2946
Ser Leu Arg Asp Tyr Leu Gln Lys His Lys Glu Arg Ile Asp His Lys
            940                 945                 950

AAA CTT CTT CAA TAC ACA TCT CAG ATA TGC AAG GGC ATG GAA TAT CTT         2994
Lys Leu Leu Gln Tyr Thr Ser Gln Ile Cys Lys Gly Met Glu Tyr Leu
            955                 960                 965

GGT ACA AAA AGG TAT ATC CAC AGG GAC CTG GCA ACA AGG AAC ATA TTG         3042
Gly Thr Lys Arg Tyr Ile His Arg Asp Leu Ala Thr Arg Asn Ile Leu
            970                 975                 980

GTG GAA AAT GAG AAC AGG GTT AAA ATA GGA GAC TTC GGA TTA ACC AAA         3090
Val Glu Asn Glu Asn Arg Val Lys Ile Gly Asp Phe Gly Leu Thr Lys
            985                 990                 995

GTC TTG CCG CAG GAC AAA GAA TAC TAC AAA GTA AAG GAG CCA GGG GAA         3138
Val Leu Pro Gln Asp Lys Glu Tyr Tyr Lys Val Lys Glu Pro Gly Glu
1000            1005                1010                1015

AGC CCC ATA TTC TGG TAC GCA CCT GAA TCC TTG ACG GAG AGC AAG TTT         3186
Ser Pro Ile Phe Trp Tyr Ala Pro Glu Ser Leu Thr Glu Ser Lys Phe
                1020                1025                1030

TCT GTG GCC TCA GAT GTG TGG AGC TTT GGA GTG GTT CTA TAC GAA CTT         3234
Ser Val Ala Ser Asp Val Trp Ser Phe Gly Val Val Leu Tyr Glu Leu
                1035                1040                1045

TTC ACA TAC ATC GAG AAG AGT AAA AGT CCA CCC GTG GAA TTT ATG CGA         3282
Phe Thr Tyr Ile Glu Lys Ser Lys Ser Pro Pro Val Glu Phe Met Arg
                1050                1055                1060

ATG ATT GGC AAT GAT AAA CAA GGG CAA ATG ATT GTG TTC CAT TTG ATA         3330
Met Ile Gly Asn Asp Lys Gln Gly Gln Met Ile Val Phe His Leu Ile
                1065                1070                1075

GAG CTA CTG AAG AGC AAC GGA AGA TTG CCA AGG CCA GAA GGA TGC CCA         3378
Glu Leu Leu Lys Ser Asn Gly Arg Leu Pro Arg Pro Glu Gly Cys Pro
1080            1085                1090                1095
```

FIG.1G

```
GAT GAG ATT TAT GTG ATC ATG ACA GAG TGC TGG AAC AAC AAT GTG AGC      3426
Asp Glu Ile Tyr Val Ile Met Thr Glu Cys Trp Asn Asn Asn Val Ser
            1100            1105            1110
                                    c
CAG CGT CCC TCC TTC AGG GAC CTT TCG TTC GGG TGG ATC AAA TCC GGG      3474
Gln Arg Pro Ser Phe Arg Asp Leu Ser Phe Gly Trp Ile Lys Ser Gly
            1115            1120            1125

ACA GTA TAGCTGCGTG AAAGAGATGG CCTTCACTCA GAGACCAAGC AGACTTCCAG        3530
Thr Val
                                                c
AACCAGAACA AAGCTCTGTA GCCTTGTGTC TACACATCCT TATCATGATG CTAGCTAGGC      3590
 (o) (o)               (o)
AGAAGAAACT GTGACGCCGT CTGCTCAAAG CTTTGCTTC                             3629
```

FIG.1H

Human JAK1

| | |
|---|---|
| ATG GCT TTC TGT GCT AAA ATG AGG AGC TCC AAG AAG ACT GAG GTG AAC | 123 |
| Met Ala Phe Cys Ala Lys Met Arg Ser Ser Lys Lys Thr Glu Val Asn | 16 |
| CTG GAG GCC CCT GAG CCA GGG GTG GAA GTG ATC TTC TAT CTG TCG GAC | 171 |
| Leu Glu Ala Pro Glu Pro Gly Val Glu Val Ile Phe Tyr Leu Ser Asp | 32 |
| AGG GAG CCC CTC CGG CTG GGC AGT GGA GAG TAC ACA GCA GAG GAA CTG | 219 |
| Arg Glu Pro Leu Arg Leu Gly Ser Gly Glu Tyr Thr Ala Glu Glu Leu | 48 |
| TGC ATC AGG GCT GCA CAG GCA TGC CGT ATC TCT CCT CTT TGT CAC AAC | 267 |
| Cys Ile Arg Ala Ala Gln Ala Cys Arg Ile Ser Pro Leu Cys His Asn | 64 |
| CTC TTT GCC CTG TAT GAC GAG AAC ACC AAG CTC TGG TAT GCT CCA AAT | 315 |
| Leu Phe Ala Leu Tyr Asp Glu Asn Thr Lys Leu Trp Tyr Ala Pro Asn | 80 |
| CGC ACC ATC ACC GTT GAT GAC AAG ATG TCC CTC CGG CTC CAC TAC CGG | 363 |
| Arg Thr Ile Thr Val Asp Asp Lys Met Ser Leu Arg Leu His Tyr Arg | 96 |
| ATG AGG TTC TAT TTC ACC AAT TGG CAT GGA ACC AAC GAC AAT GAG CAG | 411 |
| Met Arg Phe Tyr Phe Thr Asn Trp His Gly Thr Asn Asp Asn Glu Gln | 112 |
| TCA GTG TGG CGT CAT TCT CCA AAG AAG CAG AAA AAT GGC TAC GAG AAA | 459 |
| Ser Val Trp Arg His Ser Pro Lys Lys Gln Lys Asn Gly Tyr Glu Lys | 128 |
| AAA AAG ATT CCA GAT GCA ACC CCT CTC CTT GAT GCC AGC TCA CTG GAG | 507 |
| Lys Lys Ile Pro Asp Ala Thr Pro Leu Leu Asp Ala Ser Ser Leu Glu | 144 |
| TAT CTG TTT GCT CAG GGA CAG TAT GAT TTG GTG AAA TGC CTG GCT CCT | 555 |
| Tyr Leu Phe Ala Gln Gly Gln Tyr Asp Leu Val Lys Cys Leu Ala Pro | 160 |
| ATT CGA GAC CCC AAG ACC GAG CAG GAT GGA CAT GAT ATT GAG AAC GAG | 603 |
| Ile Arg Asp Pro Lys Thr Glu Gln Asp Gly His Asp Ile Glu Asn Glu | 176 |
| TGT CTA GGG ATG GCT GTC CTG GCC ATC TCA CAC TAT GCC ATG ATG AAG | 651 |
| Cys Leu Gly Met Ala Val Leu Ala Ile Ser His Tyr Ala Met Met Lys | 192 |
| AAG ATG CAG TTG CCA GAA CTG CCC AAG GAC ATC AGC TAC AAG CGA TAT | 699 |
| Lys Met Gln Leu Pro Glu Leu Pro Lys Asp Ile Ser Tyr Lys Arg Tyr | 208 |
| ATT CCA GAA ACA TTG AAT AAG TCC ATC AGA CAG AGG AAC CTT CTC ACC | 747 |
| Ile Pro Glu Thr Leu Asn Lys Ser Ile Arg Gln Arg Asn Leu Leu Thr | 224 |
| AGG ATG CGG ATA AAT AAT GTT TTC AAG GAT TTC CTA AAG GAA TTT AAC | 795 |
| Arg Met Arg Ile Asn Asn Val Phe Lys Asp Phe Leu Lys Glu Phe Asn | 240 |
| AAC AAG ACC ATT TGT GAC AGC AGC GTG TCC ACG CAT GAC CTG AAG GTG | 843 |
| Asn Lys Thr Ile Cys Asp Ser Ser Val Ser Thr His Asp Leu Lys Val | 256 |
| AAA TAC TTG GCT ACC TTG GAA ACT TTG ACA AAA CAT TAC GGT GCT GAA | 891 |
| Lys Tyr Leu Ala Thr Leu Glu Thr Leu Thr Lys His Tyr Gly Ala Glu | 272 |

FIG.2A

```
ATA TTT GAG ACT TCC ATG TTA CTG ATT TCA TCA GAA AAT GAG ATG AAT      939
Ile Phe Glu Thr Ser Met Leu Leu Ile Ser Ser Glu Asn Glu Met Asn      288

TGG TTT CAT TCG AAT GAC GGT GGA AAC GTT CTC TAC TAC GAA GTG ATG      987
Trp Phe His Ser Asn Asp Gly Gly Asn Val Leu Tyr Tyr Glu Val Met      304

GTG ACT GGG AAT CTT GGA ATC CAG TGG AGG CAT AAA CCA AAT GTT GTT     1035
Val Thr Gly Asn Leu Gly Ile Gln Trp Arg His Lys Pro Asn Val Val      320

TCT GTT GAA AAG GAA AAA AAT AAA CTG AAG CGG AAA AAA CTG GAA AAT     1083
Ser Val Glu Lys Glu Lys Asn Lys Leu Lys Arg Lys Lys Leu Glu Asn      336

AAA GAC AAG AAG GAT GAG GAG AAA AAC AAG ATC CGG GAA GAG TGG AAC     1131
Lys Asp Lys Lys Asp Glu Glu Lys Asn Lys Ile Arg Glu Glu Trp Asn      352

AAT TTT TCA TTC TTC CCT GAA ATC ACT CAC ATT GTA ATA AAG GAG TCT     1179
Asn Phe Ser Phe Phe Pro Glu Ile Thr His Ile Val Ile Lys Glu Ser      368

GTG GTC AGC ATT AAC AAG CAG GAC AAC AAG AAA ATG GAA CTG AAG CTC     1227
Val Val Ser Ile Asn Lys Gln Asp Asn Lys Lys Met Glu Leu Lys Leu      384

TCT TCC CAC GAG GAG GCC TTG TCC TTT GTG TCC CTG GTA GAT GGC TAC     1275
Ser Ser His Glu Glu Ala Leu Ser Phe Val Ser Leu Val Asp Gly Tyr      400

TTC CGG CTC ACA GCA GAT GCC CAT CAT TAC CTC TGC ACC GAC GTG GCC     1323
Phe Arg Leu Thr Ala Asp Ala His His Tyr Leu Cys Thr Asp Val Ala      416

CCC CCG TTG ATC GTC CAC AAC ATA CAG AAT GGC TGT CAT GGT CCA ATC     1371
Pro Pro Leu Ile Val His Asn Ile Gln Asn Gly Cys His Gly Pro Ile      432

TGT ACA GAA TAC GCC ATC AAT AAA TTG CGG CAA GAA GGA AGC GAG GAG     1419
Cys Thr Glu Tyr Ala Ile Asn Lys Leu Arg Gln Glu Gly Ser Glu Glu      448

GGG ATG TAC GTG CTG AGG TGG AGC TGC ACC GAC TTT GAC AAC ATC CTC     1467
Gly Met Tyr Val Leu Arg Trp Ser Cys Thr Asp Phe Asp Asn Ile Leu      464

ATG ACC GTC ACC TGC TTT GAG AAG TCT GAG CAG GTG CAG GGT GCC CAG     1515
Met Thr Val Thr Cys Phe Glu Lys Ser Glu Gln Val Gln Gly Ala Gln      480

AAG CAG TTC AAG AAC TTT CAG ATC GAG GTG CAG AAG GGC CGC TAC AGT     1563
Lys Gln Phe Lys Asn Phe Gln Ile Glu Val Gln Lys Gly Arg Tyr Ser      496

CTG CAC GGT TCG GAC CGC AGC TTC CCC AGC TTG GGA GAC CTC ATG AGC     1611
Leu His Gly Ser Asp Arg Ser Phe Pro Ser Leu Gly Asp Leu Met Ser      512

CAC CTC AAG AAG CAG ATC CTG CGC ACG GAT AAC ATC AGC TTC ATG CTA     1659
His Leu Lys Lys Gln Ile Leu Arg Thr Asp Asn Ile Ser Phe Met Leu      528

AAA CGC TGC TGC CAG CCC AAG CCC CGA GAA ATC TCC AAC CTG CTG GTG     1707
Lys Arg Cys Cys Gln Pro Lys Pro Arg Glu Ile Ser Asn Leu Leu Val      544

GCT ACT AAG AAA GCC CAG GAG TGG CAG CCC GTC TAC CCC ATG AGC CAG     1755
Ala Thr Lys Lys Ala Gln Glu Trp Gln Pro Val Tyr Pro Met Ser Gln      560
```

FIG.2B

| | |
|---|---|
| CTG AGT TTC GAT CGG ATC CTC AAG AAG GAT CTG GTC CAG GGC GAG CAC | 1803 |
| Leu Ser Phe Asp Arg Ile Leu Lys Lys Asp Leu Val Gln Gly Glu His | 576 |
| CTT GGG AGA GGC ACG AGA ACA CAC ATC TAT TCT GGG ACC CTG ATG GAT | 1851 |
| Leu Gly Arg Gly Thr Arg Thr His Ile Tyr Ser Gly Thr Leu Met Asp | 592 |
| TAC AAG GAT GAC GAA GGA ACT TCT GAA GAG AAG AAG ATA AAA GTG ATC | 1899 |
| Tyr Lys Asp Asp Glu Gly Thr Ser Glu Glu Lys Lys Ile Lys Val Ile | 608 |
| CTC AAA GTC TTA GAC CCC AGC CAC AGG GAT ATT TCC CTG GCC TTC TTC | 1947 |
| Leu Lys Val Leu Asp Pro Ser His Arg Asp Ile Ser Leu Ala Phe Phe | 624 |
| GAG GCA GCC AGC ATG ATG AGA CAG GTC TCC CAC AAA CAC ATC GTG TAC | 1995 |
| Glu Ala Ala Ser Met Met Arg Gln Val Ser His Lys His Ile Val Tyr | 640 |
| CTC TAT GGC GTC TGT GTC CGC GAC GTG GAG AAT ATC ATG GTG GAA GAG | 2043 |
| Leu Tyr Gly Val Cys Val Arg Asp Val Glu Asn Ile Met Val Glu Glu | 656 |
| TTT GTG GAA GGG GGT CCT CTG GAT CTC TTC ATG CAC CGG AAA AGT GAT | 2091 |
| Phe Val Glu Gly Gly Pro Leu Asp Leu Phe Met His Arg Lys Ser Asp | 672 |
| GTC CTT ACC ACA CCA TGG AAA TTC AAA GTT GCC AAA CAG CTG GCC AGT | 2139 |
| Val Leu Thr Thr Pro Trp Lys Phe Lys Val Ala Lys Gln Leu Ala Ser | 688 |
| GCC CTG AGC TAC TTG GAG GAT AAA GAC CTG GTC CAT GGA AAT GTG TGT | 2187 |
| Ala Leu Ser Tyr Leu Glu Asp Lys Asp Leu Val His Gly Asn Val Cys | 704 |
| ACT AAA AAC CTC CTC CTG GCC CGT GAG GGA ATC GAC AGT GAG TGT GGC | 2235 |
| Thr Lys Asn Leu Leu Leu Ala Arg Glu Gly Ile Asp Ser Glu Cys Gly | 720 |
| CCA TTC ATC AAG CTC AGT GAC CCC GGC ATC CCC ATT ACG GTG CTG TCT | 2283 |
| Pro Phe Ile Lys Leu Ser Asp Pro Gly Ile Pro Ile Thr Val Leu Ser | 736 |
| AGG CAA GAA TGC ATT GAA CGA ATC CCA TGG ATT GCT CCT GAG TGT GTT | 2331 |
| Arg Gln Glu Cys Ile Glu Arg Ile Pro Trp Ile Ala Pro Glu Cys Val | 752 |
| GAG GAC TCC AAG AAC CTG AGT GTG GCT GCT GAC AAG TGG AGC TTT GGA | 2379 |
| Glu Asp Ser Lys Asn Leu Ser Val Ala Ala Asp Lys Trp Ser Phe Gly | 768 |
| ACC ACG CTC TGG GAA ATC TGC TAC AAT GGC GAG ATC CCC TTG AAA GAC | 2427 |
| Thr Thr Leu Trp Glu Ile Cys Tyr Asn Gly Glu Ile Pro Leu Lys Asp | 784 |
| AAG ACG CTG ATT GAG AAA GAG AGA TTC TAT GAA AGC CGG TGC AGG CCA | 2475 |
| Lys Thr Leu Ile Glu Lys Glu Arg Phe Tyr Glu Ser Arg Cys Arg Pro | 800 |
| GTG ACA CCA TCA TGT AAG GAG CTG GCT GAC CTC ATG ACC CGC TGC ATG | 2523 |
| Val Thr Pro Ser Cys Lys Glu Leu Ala Asp Leu Met Thr Arg Cys Met | 816 |
| AAC TAT GAC CCC AAT CAG AGG CCT TTC TTC CGA GCC ATC ATG AGA GAC | 2571 |
| Asn Tyr Asp Pro Asn Gln Arg Pro Phe Phe Arg Ala Ile Met Arg Asp | 832 |
| ATT AAT AAG CTT GAA GAG CAG AAT CCA GAT ATT GTT TCC AGA AAA AAA | 2619 |
| Ile Asn Lys Leu Glu Glu Gln Asn Pro Asp Ile Val Ser Arg Lys Lys | 848 |

FIG. 2C

| | |
|---|---|
| AAC CAG CCA ACT GAA GTG GAC CCC ACA CAT TTT GAG AAG CGC TTC CTA<br>Asn Gln Pro Thr Glu Val Asp Pro Thr His Phe Glu Lys Arg Phe Leu | 2667<br>864 |
| AAG AGG ATC CGT GAC TTG GGA GAG GGC CAC TTT GGG AAG GTT GAG CTC<br>Lys Arg Ile Arg Asp Leu Gly Glu Gly His Phe Gly Lys Val Glu Leu | 2715<br>880 |
| TGC AGG TAT GAC CCC GAA GAC AAT ACA GGG GAG CAG GTG GCT GTT AAA<br>Cys Arg Tyr Asp Pro Glu Asp Asn Thr Gly Glu Gln Val Ala Val Lys | 2763<br>896 |
| TCT CTG AAG CCT GAG AGT GGA GGT AAC CAC ATA GCT GAT CTG AAA AAG<br>Ser Leu Lys Pro Glu Ser Gly Gly Asn His Ile Ala Asp Leu Lys Lys | 2811<br>912 |
| GAA ATC GAG ATC TTA AGG AAC CTC TAT CAT GAG AAC ATT GTG AAG TAC<br>Glu Ile Glu Ile Leu Arg Asn Leu Tyr His Glu Asn Ile Val Lys Tyr | 2859<br>928 |
| AAA GGA ATC TGC ACA GAA GAC GGA GGA AAT GGT ATT AAG CTC ATC ATG<br>Lys Gly Ile Cys Thr Glu Asp Gly Gly Asn Gly Ile Lys Leu Ile Met | 2907<br>944 |
| GAA TTT CTG CCT TCG GGA AGC CTT AAG GAA TAT CTT CCA AAG AAT AAG<br>Glu Phe Leu Pro Ser Gly Ser Leu Lys Glu Tyr Leu Pro Lys Asn Lys | 2955<br>960 |
| AAC AAA ATA AAC CTC AAA CAG CAG CTA AAA TAT GCC GTT CAG ATT TGT<br>Asn Lys Ile Asn Leu Lys Gln Gln Leu Lys Tyr Ala Val Gln Ile Cys | 3003<br>976 |
| AAG GGG ATG GAC TAT TTG GGT TCT CGG CAA TAC GTT CAC CGG GAC TTG<br>Lys Gly Met Asp Tyr Leu Gly Ser Arg Gln Tyr Val His Arg Asp Leu | 3051<br>992 |
| GCA GCA AGA AAT GTC CTT GTT GAG AGT GAA CAC CAA GTG AAA ATT GGA<br>Ala Ala Arg Asn Val Leu Val Glu Ser Glu His Gln Val Lys Ile Gly | 3099<br>1008 |
| GAC TTC GGT TTA ACC AAA GCA ATT GAA ACC GAT AAG GAG TAT TAC ACC<br>Asp Phe Gly Leu Thr Lys Ala Ile Glu Thr Asp Lys Glu Tyr Tyr Thr | 3147<br>1024 |
| GTC AAG GAT GAC CGG GAC AGC CCT GTG TTT TGG TAT GCT CCA GAA TGT<br>Val Lys Asp Asp Arg Asp Ser Pro Val Phe Trp Tyr Ala Pro Glu Cys | 3195<br>1040 |
| TTA ATG CAA TCT AAA TTT TAT ATT GCC TCT GAC GTC TGG TCT TTT GGA<br>Leu Met Gln Ser Lys Phe Tyr Ile Ala Ser Asp Val Trp Ser Phe Gly | 3243<br>1056 |
| GTC ACT CTG CAT GAG CTG CTG ACT TAC TGT GAT TCA GAT TCT AGT CCC<br>Val Thr Leu His Glu Leu Leu Thr Tyr Cys Asp Ser Asp Ser Ser Pro | 3291<br>1072 |
| ATG GCT TTG TTC CTG AAA ATG ATA GGC CCA ACC CAT GGC CAG ATG ACA<br>Met Ala Leu Phe Leu Lys Met Ile Gly Pro Thr His Gly Gln Met Thr | 3339<br>1088 |
| GTC ACA AGA CTT GTG AAT ACG TTA AAA GAA GGA AAA CGC CTG CCG TGC<br>Val Thr Arg Leu Val Asn Thr Leu Lys Glu Gly Lys Arg Leu Pro Cys | 3387<br>1104 |
| CCA CCT AAC TGT CCA GAT GAG GTT TAT CAG CTT ATG AGA AAA TGC TGG<br>Pro Pro Asn Cys Pro Asp Glu Val Tyr Gln Leu Met Arg Lys Cys Trp | 3435<br>1120 |
| GAA TTC CAA CCA TCC AAT CGG ACA AGC TTT CAG AAC CTT ATT GAA GGA<br>Glu Phe Gln Pro Ser Asn Arg Thr Ser Phe Gln Asn Leu Ile Glu Gly | 3483<br>1136 |
| TTT GAA GCA CTT TTA AAA TAA<br>Phe Glu Ala Leu Leu Lys * | 3504<br>1143 |

FIG.2D

Human TYK2

| | | |
|---|---|---|
| ATG CCT CTG CGC CAC TGG GGG ATG GCC AGG GGC AGT AAG CCC GTT GGG | 354 |
| Met Pro Leu Arg His Trp Gly Met Ala Arg Gly Ser Lys Pro Val Gly | 16 |
| GAT GGA GCC CAG CCC ATG GCT GCC ATG GGA GGC CTG AAG GTG CTT CTG | 402 |
| Asp Gly Ala Gln Pro Met Ala Ala Met Gly Gly Leu Lys Val Leu Leu | 32 |
| CAC TGG GCT GGT CCA GGC GGC GGG GAG CCC TGG GTC ACT TTC AGT GAG | 450 |
| His Trp Ala Gly Pro Gly Gly Gly Glu Pro Trp Val Thr Phe Ser Glu | 48 |
| TCA TCG CTG ACA GCT GAG GAA GTC TGC ATC CAC ATT GCA CAT AAA GTT | 498 |
| Ser Ser Leu Thr Ala Glu Glu Val Cys Ile His Ile Ala His Lys Val | 64 |
| GGT ATC ACT CCT CCT TGC TTC AAT CTC TTT GCC CTC TTC GAT GCT CAG | 546 |
| Gly Ile Thr Pro Pro Cys Phe Asn Leu Phe Ala Leu Phe Asp Ala Gln | 80 |
| GCC CAA GTC TGG TTG CCC CCA AAC CAC ATC CTA GAG ATC CCC AGA GAT | 594 |
| Ala Gln Val Trp Leu Pro Pro Asn His Ile Leu Glu Ile Pro Arg Asp | 96 |
| GCA AGC CTG ATG CTA TAT TTC CGC ATA AGG TTT TAT TTC CGG AAC TGG | 642 |
| Ala Ser Leu Met Leu Tyr Phe Arg Ile Arg Phe Tyr Phe Arg Asn Trp | 112 |
| CAT GGC ATG AAT CCT CGG GAA CCG GCT GTG TAC CGT TGT GGG CCC CCA | 690 |
| His Gly Met Asn Pro Arg Glu Pro Ala Val Tyr Arg Cys Gly Pro Pro | 128 |
| GGA ACC GAG GCA TCC TCA GAT CAG ACA GCA CAG GGG ATG CAA CTC CTG | 738 |
| Gly Thr Glu Ala Ser Ser Asp Gln Thr Ala Gln Gly Met Gln Leu Leu | 144 |
| GAC CCA GCC TCA TTT GAG TAC CTC TTT GAG CAG GGC AAG CAT GAG TTT | 786 |
| Asp Pro Ala Ser Phe Glu Tyr Leu Phe Glu Gln Gly Lys His Glu Phe | 160 |
| GTG AAT GAC GTG GCA TCA CTG TGG GAG CTC TCG ACC GAG GAG GAG ATC | 834 |
| Val Asn Asp Val Ala Ser Leu Trp Glu Leu Ser Thr Glu Glu Glu Ile | 176 |
| CAC CAC TTT AAG AAT GAG AGC CTG GGC ATG GCC TTT CTG CAC CTC TGT | 882 |
| His His Phe Lys Asn Glu Ser Leu Gly Met Ala Phe Leu His Leu Cys | 192 |
| CAC CTC GCT CTC CGC CAT GGC ATC CCC CTC GAG GAG GTG GCC AAG AAG | 930 |
| His Leu Ala Leu Arg His Gly Ile Pro Leu Glu Glu Val Ala Lys Lys | 208 |
| ACC AGC TTC AAG GAC TGC ATC CCG CGC TCC TTC CGC CGG CAT ATC CGG | 978 |
| Thr Ser Phe Lys Asp Cys Ile Pro Arg Ser Phe Arg Arg His Ile Arg | 224 |
| CAG CAC AGC GCC CTG ACC CGG CTG CGC CTT CGG AAC GTC TTC CGC AGG | 1026 |
| Gln His Ser Ala Leu Thr Arg Leu Arg Leu Arg Asn Val Phe Arg Arg | 240 |
| TTC CTG CGG GAC TTC CAG CCG GGC CGA CTC TCC CAG CAG ATG GTC ATG | 1074 |
| Phe Leu Arg Asp Phe Gln Pro Gly Arg Leu Ser Gln Gln Met Val Met | 256 |
| GTC AAA TAC CTA GCC ACA CTC GAG CGG CTG GCA CCC CGC TTC GGC ACA | 1122 |
| Val Lys Tyr Leu Ala Thr Leu Glu Arg Leu Ala Pro Arg Phe Gly Thr | 272 |

FIG. 3A

```
GAG CGT GTG CCC GTG TGC CAC CTG AGG CTG CTG GCC CAG GCC GAG GGG    1170
Glu Arg Val Pro Val Cys His Leu Arg Leu Leu Ala Gln Ala Glu Gly     288

GAG CCC TGC TAC ATC CGG GAC AGT GGG GTG GCC CCT ACA GAC CCT GGC    1218
Glu Pro Cys Tyr Ile Arg Asp Ser Gly Val Ala Pro Thr Asp Pro Gly     304

CCT GAG TCT GCT GCT GGG CCC CCA ACC CAC GAG GTG CTG GTC ACA GGC    1266
Pro Glu Ser Ala Ala Gly Pro Pro Thr His Glu Val Leu Val Thr Gly     320

ACT GGT GGC ATC CAG TGG TGG CCA GTA GAG GAG GAG GTG AAC AAG GAG    1314
Thr Gly Gly Ile Gln Trp Trp Pro Val Glu Glu Glu Val Asn Lys Glu     336

GAG GGT TCT AGT GGC AGC AGT GGC AGG AAC CCC CAA GCC AGC CTG TTT    1362
Glu Gly Ser Ser Gly Ser Ser Gly Arg Asn Pro Gln Ala Ser Leu Phe     352

GGG AAG AAG GCC AAG GCT CAC AAG GCA TTC GGC CAG CCG GCA GAC AGG    1410
Gly Lys Lys Ala Lys Ala His Lys Ala Phe Gly Gln Pro Ala Asp Arg     368

CCG CGG GAG CCA CTG TGG GCC TAC TTC TGT GAC TTC CGG GAC ATC ACC    1458
Pro Arg Glu Pro Leu Trp Ala Tyr Phe Cys Asp Phe Arg Asp Ile Thr     384

CAC GTG GTG CTG AAA GAG CAC TGT GTC AGC ATC CAC CGG CAG GAC AAC    1506
His Val Val Leu Lys Glu His Cys Val Ser Ile His Arg Gln Asp Asn     400

AAG TGC CTG GAG CTG AGC TTG CCT TCC CGG GCT GCG GCG CTG TCC TTC    1554
Lys Cys Leu Glu Leu Ser Leu Pro Ser Arg Ala Ala Ala Leu Ser Phe     416

GTG TCG CTG GTG GAC GGC TAT TTC CGC CTG ACG GCC GAC TCC AGC CAC    1602
Val Ser Leu Val Asp Gly Tyr Phe Arg Leu Thr Ala Asp Ser Ser His     432

TAC CTG TGC CAC GAG GTG GCT CCC CCA CGG CTG GTG ATG AGC ATC CGG    1650
Tyr Leu Cys His Glu Val Ala Pro Pro Arg Leu Val Met Ser Ile Arg     448

GAT GGG ATC CAC GGA CCC CTG CTG GAG CCA TTT GTG CAG GCC AAG CTG    1698
Asp Gly Ile His Gly Pro Leu Leu Glu Pro Phe Val Gln Ala Lys Leu     464

CGG CCC GAG GAC GGC CTG TAC CTC ATT CAC TGG AGC ACC AGC CAC CCC    1746
Arg Pro Glu Asp Gly Leu Tyr Leu Ile His Trp Ser Thr Ser His Pro     480

TAC CGC CTG ATC CTC ACA GTG GCC CAG CGT AGC CAG GCA CCA GAC GGC    1794
Tyr Arg Leu Ile Leu Thr Val Ala Gln Arg Ser Gln Ala Pro Asp Gly     496

ATG CAG AGC TTG CGG CTC CGA AAG TTC CCC ATT GAG CAG CAG GAC GGG    1842
Met Gln Ser Leu Arg Leu Arg Lys Phe Pro Ile Glu Gln Gln Asp Gly     512

GCC TTC GTG CTG GAG GGC TGG GGC CGG TCC TTC CCC AGC GTT CGG GAA    1890
Ala Phe Val Leu Glu Gly Trp Gly Arg Ser Phe Pro Ser Val Arg Glu     528

CTT GGG GCT GCC TTG CAG GGC TGC TTG CTG AGG GCC GGG GAT GAC TGC    1938
Leu Gly Ala Ala Leu Gln Gly Cys Leu Leu Arg Ala Gly Asp Asp Cys     544

TTC TCT CTG CGT CGC TGT TGC CTG CCC CAA CCA GGA GAA ACC TCC AAT    1986
Phe Ser Leu Arg Arg Cys Cys Leu Pro Gln Pro Gly Glu Thr Ser Asn     560
```

FIG.3B

```
CTC ATC ATC ATG CGG GGG GCT CGG GCC AGC CCC AGG ACA CTC AAC CTC   2034
Leu Ile Ile Met Arg Gly Ala Arg Ala Ser Pro Arg Thr Leu Asn Leu    576

AGC CAG CTC AGC TTC CAC CGG GTT GAC CAG AAG GAG ATC ACC CAG CTG   2082
Ser Gln Leu Ser Phe His Arg Val Asp Gln Lys Glu Ile Thr Gln Leu    592

TCC CAC TTG GGC CAG GGC ACA AGG ACC AAC GTG TAT GAG GGC CGC CTG   2130
Ser His Leu Gly Gln Gly Thr Arg Thr Asn Val Tyr Glu Gly Arg Leu    608

CGA GTG GAG GGC AGC GGG GAC CCT GAG GAG GGC AAG ATG GAT GAC GAG   2178
Arg Val Glu Gly Ser Gly Asp Pro Glu Glu Gly Lys Met Asp Asp Glu    624

GAC CCC CTC GTG CCT GGC AGG GAC CGT GGG CAG GAG CTA CGA GTG GTG   2226
Asp Pro Leu Val Pro Gly Arg Asp Arg Gly Gln Glu Leu Arg Val Val    640

CTC AAA GTG CTG GAC CCT AGT CAC CAT GAC ATC GCC CTG GCC TTC TAC   2274
Leu Lys Val Leu Asp Pro Ser His His Asp Ile Ala Leu Ala Phe Tyr    656

GAG ACA GCC AGC CTC ATG AGC CAG GTC TCC CAC ACG CAC CTG GCC TTC   2322
Glu Thr Ala Ser Leu Met Ser Gln Val Ser His Thr His Leu Ala Phe    672

GTG CAT GGC GTC TGT GTG CGC GGC CCT GAA AAT AGC ATG GTG ACA GAG   2370
Val His Gly Val Cys Val Arg Gly Pro Glu Asn Ser Met Val Thr Glu    688

TAC GTG GAG CAC GGA CCC CTG GAT GTG TGG CTG CGG AGG GAG CGG GGC   2418
Tyr Val Glu His Gly Pro Leu Asp Val Trp Leu Arg Arg Glu Arg Gly    704

CAT GTG CCC ATG GCT TGG AAG ATG GTG GTG GCC CAG CAG CTG GCC AGC   2466
His Val Pro Met Ala Trp Lys Met Val Val Ala Gln Gln Leu Ala Ser    720

GCC CTC AGC TAC CTG GAG AAC AAG AAC CTG GTT CAT GGT AAT GTG TGT   2514
Ala Leu Ser Tyr Leu Glu Asn Lys Asn Leu Val His Gly Asn Val Cys    736

GGC CGG AAC ATC CTG CTG GCC CGG CTG GGG TTG GCA GAG GGC ACC AGC   2562
Gly Arg Asn Ile Leu Leu Ala Arg Leu Gly Leu Ala Glu Gly Thr Ser    752

CCC TTC ATC AAG CTG AGT GAT CCT GGC GTG GGC CTG GGC GCC CTC TCC   2610
Pro Phe Ile Lys Leu Ser Asp Pro Gly Val Gly Leu Gly Ala Leu Ser    768

AGG GAG GAG CGG GTG GAG AGG ATC CCC TGG CTG GCC CCC GAA TGC CTA   2658
Arg Glu Glu Arg Val Glu Arg Ile Pro Trp Leu Ala Pro Glu Cys Leu    784

CCA GGT GGG GCC AAC AGC CTA AGC ACC GCC ATG GAC AAG TGG GGG TTT   2706
Pro Gly Gly Ala Asn Ser Leu Ser Thr Ala Met Asp Lys Trp Gly Phe    800

GGC GCC ACC CTC CTG GAG ATC TGC TTT GAC GGA GAG GCC CCT CTG CAG   2754
Gly Ala Thr Leu Leu Glu Ile Cys Phe Asp Gly Glu Ala Pro Leu Gln    816

AGC CGC AGT CCC TCC GAG AAG GAG CAT TTC TAC CAG AGC CAG CAC CGG   2802
Ser Arg Ser Pro Ser Glu Lys Glu His Phe Tyr Gln Ser Gln His Arg    832

CTG CCC GAG CCC TCC TGC CCA CAG CTG GCC ACA CTC ACC AGC CAG TGT   2850
Leu Pro Glu Pro Ser Cys Pro Gln Leu Ala Thr Leu Thr Ser Gln Cys    848
```

FIG. 3C

```
CTG ACC TAT GAG CCA ACC CAG AGG CCA TCA TTC CGC ACC ATC CTG CGT    2898
Leu Thr Tyr Glu Pro Thr Gln Arg Pro Ser Phe Arg Thr Ile Leu Arg    864

GAC CTC ACC CGC GTG CAG CCC CAC AAT CTT GCT GAC GTC TTG ACT GTG    2946
Asp Leu Thr Arg Val Gln Pro His Asn Leu Ala Asp Val Leu Thr Val    880

AAC CGG GAC TCA CCG GCC GTC GGA CCT ACT ACT TTC CAC AAG CGC TAT    2994
Asn Arg Asp Ser Pro Ala Val Gly Pro Thr Thr Phe His Lys Arg Tyr    896

TTG AAA AAG ATC CGA GAT CTG GGC GAG GGT CAC TTC GGC AAG GTC AGC    3042
Leu Lys Lys Ile Arg Asp Leu Gly Glu Gly His Phe Gly Lys Val Ser    912

TTG TAC TGC TAC GAT CCG ACC AAC GAC GGC ACT GGC GAG ATG GTG GCG    3090
Leu Tyr Cys Tyr Asp Pro Thr Asn Asp Gly Thr Gly Glu Met Val Ala    928

GTG AAA GCC CTC AAG GCA GAC TGC GGC CCC CAG CAC CGC TCG GGC TGG    3138
Val Lys Ala Leu Lys Ala Asp Cys Gly Pro Gln His Arg Ser Gly Trp    944

AAG CAG GAG ATT GAC ATT CTG CGC ACG CTC TAC CAC GAG CAC ATC ATC    3186
Lys Gln Glu Ile Asp Ile Leu Arg Thr Leu Tyr His Glu His Ile Ile    960

AAG TAC AAG GGC TGC TGC GAG GAC CAA GGC GAG AAG TCG CTG CAG CTG    3234
Lys Tyr Lys Gly Cys Cys Glu Asp Gln Gly Glu Lys Ser Leu Gln Leu    976

GTC ATG GAG TAC GTG CCC CTG GGC AGC CTC CGA GAC TAC CTG CCC CGG    3282
Val Met Glu Tyr Val Pro Leu Gly Ser Leu Arg Asp Tyr Leu Pro Arg    992

CAC AGC ATC GGG CTG GCC CAG CTG CTG CTC TTC GCC CAG CAG ATC TGC    3330
His Ser Ile Gly Leu Ala Gln Leu Leu Leu Phe Ala Gln Gln Ile Cys    1008

GAG GGC ATG GCC TAT CTG CAC GCG CAC GAC TAC ATC CAC CGA GAC CTA    3378
Glu Gly Met Ala Tyr Leu His Ala His Asp Tyr Ile His Arg Asp Leu    1024

GCC GCG CGC AAC GTG CTG CTG GAC AAC GAC AGG CTG GTC AAG ATC GGG    3426
Ala Ala Arg Asn Val Leu Leu Asp Asn Asp Arg Leu Val Lys Ile Gly    1040

GAC TTT GGC CTA GCC AAG GCC GTG CCC GAA GGC CAC GAG TAC TAC CGC    3474
Asp Phe Gly Leu Ala Lys Ala Val Pro Glu Gly His Glu Tyr Tyr Arg    1056

GTG CGC GAG GAT GGG GAC AGC CCC GTG TTC TGG TAT GCC CCA GAG TGC    3522
Val Arg Glu Asp Gly Asp Ser Pro Val Phe Trp Tyr Ala Pro Glu Cys    1072

CTG AAG GAG TAT AAG TTC TAC TAT GCG TCA GAT GTC TGG TCC TTC GGG    3570
Leu Lys Glu Tyr Lys Phe Tyr Tyr Ala Ser Asp Val Trp Ser Phe Gly    1088

GTG ACC CTG TAT GAG CTG CTG ACG CAC TGT GAC TCC AGC CAG AGC CCC    3618
Val Thr Leu Tyr Glu Leu Leu Thr His Cys Asp Ser Ser Gln Ser Pro    1104

CCC ACG AAA TTC CTT GAG CTC ATA GGC ATT GCT CAG GGT CAG ATG ACA    3666
Pro Thr Lys Phe Leu Glu Leu Ile Gly Ile Ala Gln Gly Gln Met Thr    1120

GTT CTG AGA CTC ACT GAG TTG CTG GAA CGA GGG GAG AGG CTG CCA CGG    3714
Val Leu Arg Leu Thr Glu Leu Leu Glu Arg Gly Glu Arg Leu Pro Arg    1136
```

FIG.3D

| | |
|---|---|
| CCC GAC AAA TGT CCC TGT GAG GTC TAT CAT CTC ATG AAG AAC TGC TGG | 3762 |
| Pro Asp Lys Cys Pro Cys Glu Val Tyr His Leu Met Lys Asn Cys Trp | 1152 |
| | |
| GAG ACA GAG GCG TCC TTT CGC CCA ACC TTC GAG AAC CTC ATA CCC ATT | 3810 |
| Glu Thr Glu Ala Ser Phe Arg Pro Thr Phe Glu Asn Leu Ile Pro Ile | 1168 |
| | |
| CTG AAG ACA GTC CAT GAG AAG TAC CAA GGC CAG GCC CCT TCA GTG TTC | 3858 |
| Leu Lys Thr Val His Glu Lys Tyr Gln Gly Gln Ala Pro Ser Val Phe | 1184 |
| | |
| AGC GTG TGC | 3867 |
| Ser Val Cys | 1187 |

FIG.3E

```
pileup.msf(Jak1)  ..MQYLNIKE  DCNAMAFCAK  MRSFKKTEVK  QVVP.EPGVE  VTFYLLDREP
pileup.msf(Tyk2)  MPLRHWGMAR  GSKPVG....  .....DGAQ   PMAA.MGGLK  VLLHWAGPGG
pileup.msf(Jak2)  MGMACLTMTE  MEATSTSPVH  QNGDIPGSAN  SVKQIEPVLQ  VYLYHSLGQA
Consensus         M-M--L-M-E  ----------  -------A--  -V---EPGL-  V-LY------ pileup.msf(Jak1)  ....LRLGSG  EYTAEELCIR  AAQECSISPL  CHNLFALYDE  STKLWYAPNR
pileup.msf(Tyk2)  GEPWVTFSES  SLTAEEVCIH  IAHKVGITPP  CFNLFALFDA  QAQVWLPPNH
pileup.msf(Jak2)  EGEYLKFPSG  EYVAEEICVA  ASKACGITPV  YHNMFALMSE  TERIWYPPNH
Consensus         ----L-FSG   EYTAEE-CI-  AA--CGITP-  CHNLFAL-DE  ---WYPPNH pileup.mfs(Jak1)  IITVDDKTSL  RLHYRMRFYF  TNWHGTNDNE  QSVWRHSPKK  QKNGYEKKRV
pileup.msf(Tyk2)  ILEIPRDASL  MLYFRIRFYF  RNWHGMNPRE  PAVYRCGPPG  TEASSD..QT
pileup.msf(Jak2)  VFHIDESTRH  DILYRIRFYF  PHWY......  ........    RTYRGVSRG
Consensus         I--ID--TSL  -L-YRIRFYF  -NWHG-N--E  --V-RCSP--  ----Y---R- pileup.msf(Jak1)  PEATPLLDAS  SLEYLFAQGQ  YDLIKFLAPI  RDPKTEQDGH  DIENECLGMA
pileup.msf(Tyk2)  AQGMQLLDPA  SFEYLFEQGK  HEFVNDVASL  WELSTEEEIH  HFKNESLGMA
pileup.msf(Jak2)  AEA.PLLDDF  VMSYLFAQWR  HDFVHGWIKV  ........PVTH  ETQEECLGMA
Consensus         AEA-PLLD--  S-EYLFAQG-  HDFV---A--  ----TE---H  ---NECLGMA pileup.msf(Jak1)  VLAISHYAMM  KKMQLPELPK  DISYKRYIPE  TLNKSIRQRN  LLTRMRINNV
pileup.msf(Tyk2)  FLHLCHLALR  HGIPLEEVAK  KTSFKDCIPR  SFRRHIRQHS  ALTRLRLRNV
pileup.msf(Jak2)  VLDMMRIAKE  KDQTPLAVYN  SVSYKTFLPK  CVRAKIQDYH  ILTRKRIRYR
Consensus         VL---H-A--  K---L-EV-K  --SYK--IP-  --R--IRQ--  -LTR-RIRNV
```

FIG.5A

```
pileup.msf(Jak1)   FKDFLKEFNN   KTICDSSVST   HDLKVKYLAT   LETLTKHYGA   EIFETSMLLI
pileup.msf(Tyk2)   FRRFLRDFQ.   ...PGRLSQ    QMVMVKYLAT   LERLAPRFGT   ERVPVCHLRL
pileup.msf(Jak2)   FRRFIQQF..   ...SQCKATA   RNLKLKYLIN   LETLQSAFYT   EQFEV.....
       Consensus   FRRFL--F--   -------S-    --LKVKYLAT   LETL---FGT   E-FEV--L-- pileup.msf(Jak1)   SSENELSRCH   SNDS......   .......GNV   LYEVMVTGNL   GIQWRQXPNV
pileup.msf(Tyk2)   LAQAEGEPCY   IRDSGVAPTD   PGPESAAGPP   THEVLVTGTG   GIQWMPVEEE
pileup.msf(Jak2)   .........    .......KE    SARGPSQEEI   FATIIITGNG   GIQWS.....
       Consensus   ----E---C-   ---DS-----   -------G--   --EV-VTGNG   GIQWS----- pileup.msf(Jak1)   VPVEKE....   ....KNKLK    RKKLEYNKHK   KDDERNKLRE   EWNNFSYFPE
pileup.msf(Tyk2)   VNKEEGSSGS   SGRNPQASLF   GKKAKAHKAF   GQPADRPREP   LWAYFCDFRD
pileup.msf(Jak2)   .........    .........    RGK          HKESETLTEQ   DVQLYCDFPD
       Consensus   V--E------   -------L--   -KK----K-K   --------E-   -W--FCDFPD pileup.msf(Jak1)   ITHIVIKE..   .......SVV   SINKQDNKNM   ELKLSSREEA   LSFVSLVDGY
pileup.msf(Tyk2)   ITHVVLKE..   .......HCV   SIHRQDNKCL   ELSLPSRAAA   LSFVSLVDGY
pileup.msf(Jak2)   IIDVSIKQAN   QECSNESRIV   TVHKQDGKVL   EIELSSLKEA   LSFVSLIDGY
       Consensus   ITHVVIKE--   ---------V   SIHKQDNK-L   EL-LSSR-EA   LSFVSLVDGY pileup.msf(Jak1)   FRLTADAHHY   LCTDVAPPLI   VHNIQNGCHG   PICTEYAINK   LRQEGSEEGM
pileup.msf(Tyk2)   FRLTADSSHY   LCHEVAPPRL   VMSIRDGIHG   PLLEPFVQAK   LR...PEDGL
pileup.msf(Jak2)   YRLTADAHHY   LCKEVAPPAV   LENIHSNCHG   PTSMDFAISK   LKKAGNQTGL
       Consensus   FRLTADAHHY   LC-EVAPP--   V-NI--GCHG   PI---FAI-L   LR--G-E-GL
```

FIG.5B

```
pileup.msf(Jak1)    YVLRWSCTDF    DNILMTVTCG    EKSEVLGGQK    .QFNFQIE     VQKFRYSLHG
pileup.msf(Tyk2)    YLIHWSTSHP    YRLILTVA..    QRSQAPDGMQ    SLRLRKFPIE   QQDGAFVLEG
pileup.msf(Jak2)    YVLRCSPKDF    NKYFLTFA.V    ERENVIEYKH    CLITKN....   .ENGEYNLSG
Consensus           YVLRWS--DF    ----LTVA--    ERS-V--G--    -L--KNF-IE   -Q-G-Y-L-G pileup.msf(Jak1)    SMDHFPSLRD    LMNHLKKQIL    RTDNISFVLK    RCCQPKPREI   SNLLV.....
pileup.msf(Tyk2)    WGRSFPSVRE    LGAALQGCLL    RAGDDCFSLR    RCCLPQPGET   SNLIT.....
pileup.msf(Jak2)    TKRNFSNLKD    LLNCYQMETV    RSDSIIFQFT    KCCPPKPKDK   SNLLVFRTNG
Consensus           --R-FPSLRD    L-N-LQ---L    R-D-I-F-L-    RCC-PKP-E-   SNLLV----- pileup.msf(Jak1)    ..ATKKAQEW    QPVYSMSQLS    FDRILKKDII    QGEHLGRGTR   THIYSGTLL.
pileup.msf(Tyk2)    ...MRGARAS    PRTLNLSQLS    FHRVDQKEIT    QLSHLGQGTR   TNVYEGRLRV
pileup.msf(Jak2)    ISDVQISPTL    QRHNNVNQMV    FHKIRNEDLI    FNESLGQGTF   TKIFKGVRRE
Consensus           -----A----    QR--N-SQLS    FHRI--KDII    Q-EHLGQGTR   T-IY-G-LRpileup.msf(Jak1)    .........D    YKDEEGIAEE    K....KIKVI    LKVLDPSHRD   ISLAFFEAAS
pileup.msf(Tyk2)    EGSGDPEEGK    MDDEDPLVPG    RDRGQELRVV    LKVLDPSHHD   IALAFYETAS
pileup.msf(Jak2)    .........-    ........VGD    YGQLHKTEVL    LKVLDKAHRN   YSESFFEAAS
Consensus           ----------    -----DE---    -----K--V-    LKVLDPSHRD   ISLAFFEAAS pileup.msf(Jak1)    MMRQVSHKHI    VYLYGVCVRD    VENIMVEEFV    EGGPLDLFMH   RKSDALTTPW
pileup.msf(Tyk2)    LMSQVSHTHL    AFVHGVCVRG    PENIMTEYV     EHGPLDVWLR   RERGHVPMAW
pileup.msf(Jak2)    MMSQLSHKHL    VLNYGVCVCG    EENILVQEFV    KFGSLDTYLK   KNKNSINILW
Consensus           MMSQVSHKHL    V--YGVCVRG    -ENIMV-EFV    E-GPLD--L-   R-------W
```

FIG.5C

```
pileup.msf(Jak1)   KFKVAKQLAS   ALSYLEDKDL   VHGNVCTKNL   LLAR.EGIDS   DIGPFIKSLD
pileup.msf(Tykw)   KMVVAQQLAS   ALSYLENKNL   VHGNVCGRNI   LLAR.LGLAE   GTSPFIKLSD
pileup.msf(Jak2)   KLGVAKQLAW   AMHFLEEKSL   IHGNVCAKNI   LLIREEDRRT   GNPPFIKLSD
         Consensus K--VAKQLAS   ALSYLE-L-L   VHGNVC-KNI   LLAR-EG---   G--PFIKLSD pileup.msf(Jak1)   PGIPVSVLTR   QECIERIPWI   APECVEDSKN   .LSVAADKWS   FGTTLWEICY
pileup1msf(Tyk2)   PGVGLGALSR   EERVERIPWL   APECLPGGAN   SLSTAMDKWG   FGATLLEICF
pileup.msf(Jak2)   PGISITVLPK   DILQERIPWV   PPECIENPKN   .LNLATDKWS   FGTTLWEICS
         Consensus PGI---VL-R   -E--ERIPW-   APEC-E--KN   -LS-A-DKWS   FGTTLWEICpileup.msf(Jak1)   NGEIPLKDKT   LIEKERFYES   RCRPVTPSCK   ELADLMTRCM   NYDPNQRPFF
pileup.msf(Tyk2)   DGEAPLQSRS   PSEKEHFYQR   APECLPGGAN   QLATLTSQCL   FGATLLEICF
pileup.msf(Jak2)   GGDKPLSALD   SQRKLQFYED   KHQLPAPKWT   ELANLINNCM   FGTTLWEICS
         Consensus -GE-PL----   --EKE-FYE-   -HRLP-PSC-   ELA-L---CM   -YEP-QRP-F pileup.msf(Jak1)   RAIMRDINKL   ..........E  EQN.PDI...   .VSEKQPTTE   VDPTHFEKRF
pileup.msf(Tyk2)   RTILRDLTRL   ..........Q  PHNLADV...   .LTVNPDSPA   SDPTVFHKRY
pileup.msf(Jak2)   RAVIRDLNSL   FTPDYELLTE   NDMLPNMRIG   ALGFSGAFED   RDPTQFEERH
         Consensus RAI-RDLN-L   ---------E   --NLPD----   -L--------   -DPT-FEKRpileup.msf(Jak1)   LKKRIRDLGEG  HFGKVELCRY   DPECDNTGEQ   VAVKSLKPES   GGNHIADLKK
pileup.msf(Tyk2)   LKKIRDLGEG   HFGKVSLYCY   DPTNDGTGEM   VAVKALKADC   GPQHRSGWKQ
pileup.msf(Jak2)   LKFLQQLGKG   NFGSVEMCRY   DPLQDNTGEV   VAVKKLQ.HS   TEEHLRDFER
         Consensus LK-IRDLGEG   HFGKVELCRY   DP--DNTGE-   VAVK-LK--S   G--H-D-K-
```

FIG.5D

|  |  |  |  |  |  |
|---|---|---|---|---|---|
| pileup.msf(Jak1) | EIEILRNLYH | ENIVKYKGIC | MEDGGNGIKL | IMEFLPSGSL | KEYLPKNKNK |
| pileup.msf(Tyk2) | EIDILRTLYH | EHIIKYKGCC | EDQGEKSLQL | VMEYVPLGSL | RDYLP..RHS |
| pileup.msf(Jak2) | EIEILKSLQH | DNVKYKGVCQ | YSAGRRNLRL | IMEYLPYGSL | RDYLQKHKER |
| Consensus | EIEILR-LYH | ENIVKYKG-C | ---G---L-L | IMEYLP-GSL | RDYLPK-K-- |
|  |  |  |  |  |  |
| pileup.msf(Jak1) | INLKQQLKYA | IQICKGMDYL | GSRQYVHRDL | AARNVLVESE | HQVKIGDFGL |
| pileup.msf(Tyk2) | IGLAQLLLFA | QQICECMAYL | HAQHYIHRDL | AARNVLLDND | RLVKIGDFGL |
| pileup.msf(Jak2) | IDHKKLLQYT | SQICKGMEYL | GTKRYIHRDL | ATRNILVENE | NRVKIGDFGL |
| Consensus | I-LKQLL-YA | -QICKGM-YL | G---YIHRDL | AARNVLVENE | --VKIGDFGL |
|  |  |  |  |  |  |
| pileup.msf(Jak1) | TKAIETDKEY | YTVKDDRDSP | VFWYAPECLI | QCKFYIASDV | WSFGVTLHEL |
| pileup.msf(Tyk2) | AKAVPEGHEY | YRVREDGDSP | VFWYAPECLK | EYKFYYASDV | WSFGVTLYEL |
| pileup.msf(Jak2) | TKVLPQDKEY | YKVKEPGESP | IFWYAPESLT | ESKFSVASDV | WSFGVVLYEL |
| Consensus | TAK-P-DKEY | Y--VKEDGDSP | VFWYAPECL- | ESKFSVASDV | WSFGVVLYEL |
|  |  |  |  |  |  |
| pileup.msf(Jak1) | LTYCDSDFSP | MALFLKMIGP | T.HGQMTVTR | LVNTLKEGKR | LPCPPNCPDE |
| pileup.msf(Tyk2) | LTHCDSSQSP | PTKFLELIGI | A.QGQMTVLR | LTELLERGER | LPRPDKCPCE |
| pileup.msf(Jak2) | FTYIEKSKSP | PVEFMRMIGN | DKQGQMIVFH | LIELLSKNGR | LPRPEGCPDE |
| Consensus | LTYCDSS-SP | P--FL-MIG- | --QGQMTV-R | L-ELLK-G-R | LPRP--CPDE |
|  |  |  |  |  |  |
| pileup.msf(Jak1) | VYQLMRKCWE | FQPSNRTTFQ | NLIEGFEALL | K........ | LPCPPNCPDE |
| pileup.msf(Tyk2) | VYHLMKNCWE | TEASFRPTFE | NLIPILKTVH | EKYQGQAPSV | FSVC* |
| pileup.msf(Jak2) | IYVIMTECWN | NNVSQRPSFR | DLSFGWIKSG | TVI...... |  |
| Consensus | VY-LM--CWE | ---S-RPTF- | NLI-G---- | ---------- | ---- |

FIG.5E

JAK KINASES AND REGULATION OF CYTOKINE SIGNAL TRANSDUCTION

STATEMENT AS TO RIGHTS TO INVENTIONS MADE UNDER FEDERALLY-SPONSORED RESEARCH AND DEVELOPMENT

Part of the work performed during development of this invention utilized U.S. Government funds under Grant No. RO1 DK42932 from the National Institute of Diabetes and Digestive and Kidney Diseases. The U.S. Government has certain rights in this invention.

BACKGROUND OF THE INVENTION

1. Field of the Invention

The present invention relates generally to the Jak family of kinases and their role in the cellular response to the binding of cytokines to their respective receptors, and particularly those cytokines which bind to members of the cytokine receptor superfamily. The invention relates more specifically to the cytokine-induced activation of members of the Jak kinase family, to the identification of interactions between specific cytokines and members of the Jak kinase family, and to methods of regulating this interaction.

2. Description of the Background Art

The growth, differentiation and function of eukaryotic cells is regulated in large part by extracellular factors, referred to generally as cytokines herein. These cytokines induce cellular responses by binding to their respective receptors. The receptors for cytokines fall into two major families, the cytokine receptor superfamily and the tyrosine kinase receptor superfamily.

Receptors belonging to the tyrosine kinase receptor superfamily are characterized by the presence of an identifiable cytoplasmic tyrosine kinase domain involved in the transduction of the cytokine-receptor binding signal. Members of this receptor family have been further classified into three structural subgroups (Yarden, Y. et al., Ann. Rev. Biochem. 57:443–478(1988). Members of the first subgroup are characterized as monomeric with two cysteine rich sequence repeat regions within their extracellular domains and include the receptor for epidermal growth factor (EGF) and TGF-α (Ullrich, A. et al., Nature 309:418–425 (1984). Members of the second subgroup are characterized as functioning as heterotetramers and include the receptors for insulin (Ullrich, A. et al., Nature 313:756–761 (1985); Ebina, Y. et al., Cell. 40:747–758 (1985)) and insulin-like growth factor-1 (IGF-1)(Ullrich, A. et al., EMBO J. 5:2503–2512 (1986). Members of the third subgroup are characterized by the presence of conserved repeat structures and the interruption of their catalytic domains by long (77–107 amino acids) insertion sequences. This third subgroup includes receptors for platelet-derived growth factor (PDGF-R) (Yarden, Y. et al., Nature 323:226–232 (1986)) and macrophage growth factor (CSF-1)(Sherr, C. J. et al., Cell 41:665–676 (1985)).

Receptors belonging to the cytokine receptor superfamily are characterized by the presence of four positionally conserved cysteines and a WSXWS (SEQ ID No. 1) motif in the extracellular domain. The family is also characterized by variably sized cytoplasmic domains that show very limited sequence similarity and which do not contain identifiable motifs that might indicate the signal transducing mechanisms. Members of the cytokine receptor superfamily include the hematopoietic growth actor receptors, receptors for growth hormone, the prolactin receptor, cilliary neurotrophic factor and others (Bazan, J. F., Science 257:410–413 (1992)). The receptors for interferon, although more distantly related, have been speculated to have evolved from a progenitor common to this receptor superfamily.

In spite of the lack of catalytic domains, considerable evidence suggests that signal transduction of members of the cytokine receptor superfamily involves tyrosine phosphorylation (Miyajima, A., et al., Annu. Rev. Immunol. 10:295–331 (1992); Metcalf, D., Nature 339:27–30 (1989)). There is also some evidence that members of this receptor superfamily may utilize common tyrosine phosphorylation pathways for signal transduction. Specifically, binding of hematopoietic growth factors to their respective receptors have been found to induce comparable patterns of tyrosine phosphorylation (Ihle, J. N., in Interleukins: Molecular Biology and Immunology, Kishimoto, T., ed., Karger, Basel, pp. 65–106 (1992)).

While it is widely appreciated that cytokine receptors from both families described above play a key role in cellular growth regulation, little is known about the biochemical cascades triggered by the binding of cytokines to these receptors. An understanding of the steps involved in the transduction of the cytokine signal through these receptors would be useful for identifying molecules which play a critical role in signal transduction and which can serve as targets for regulating the activity of these cytokines.

A model for the study of receptor signal transduction has been developed for the erythropoietin receptor (EpoR), one of the hematopoietic growth factor receptors and a member of the cytokine receptor superfamily. Introduction of the EpoR into interleukin-3 (IL-3) dependent cell lines confers on the cells the ability to proliferate in response to Epo (D'Andrea et al., Cell 57:277–285 (1989); Miura et al., Mol. Cell Biol. 11:4895–4902 (1991)). In transfected cells, Epo induces the expression of a series of immediate early genes including c-myc, c-fos, c-pim-1 and egr-1 (Miura et al., Mol. Cell. Biol. 13:1788–1795 (1993)). In addition, Epo induces the rapid tyrosine phosphorylation of a series of cellular substrates (Linnekin et al., Proc. Natl. Acad. Sci. USA 89:6237–6241 (1992); Dusanter-Fourt et al., J. Biol. Chem. 267:10670–10675 (1992); Quelle and Wojchowski, J. Biol. Chem. 266:609–614 (1991); Miura et al., Mol. Cell Biol. 11:4895–4902 (1991); Yoshimura and Lodish, Mol. Cell. Biol. 12:706–715 (1992); Damen et al., Blood 80:1923–1932 (1992)), suggesting that EpoR may function by coupling ligand binding to the activation of a protein tyrosine kinase.

Although the importance of protein tyrosine phosphorylation for biological activities associated with Epo-EpoR binding has been clearly demonstrated, very little has been known concerning the kinases that might be involved. The rapid induction of tyrosine phosphorylation of the carboxyl region of EpoR (Miura et al., Mol. Cell Biol. 11:4895–4902 (1991); Yoshimura and Lodish, Mol. Cell. Biol. 12:706–715 (1992); Dusanter-Fourt et al., J. Biol. Chem. 267:10670–10675 (1992)) suggests that the receptor is closely associated with a kinase, either constitutively or following ligand binding. One study (Yoshimura and Lodish, Mol. Cell. Biol. 12:706–715 (1992)) identified a non-glycosylated protein of 130 kDa that could be cross-linked with the receptor and which was tyrosine phosphorylated either in vivo or in in vitro kinase assays as assessed by its ability to be detected by an antiphosphotyrosine antibody. Whether the 130 kDa protein was a kinase could not be determined. Recent studies (Linnekin et al., Proc. Natl. Acad. Sci. USA 89:6237–6241 (1992)) also identified a 97 kDa substrate of tyrosine phosphorylation which could be radiolabeled with an azido derivative of ATP, suggesting that it was a kinase. Whether the 130 kDa or 97 kDa potential kinases are previously characterized kinases was not determined.

Tyrosine phosphorylation has also been observed in response to the cytokine interferon gamma (IFNγ). Recent studies (Shuai et al., *Science* 259:1808–1812 (1992)) have demonstrated that IFNγ induces tyrosine phosphorylation of a 91 kDa protein, and that this 91 kDa protein migrates to the nucleus and binds a γ-activated site.

Tyrosine phosphorylation has further been associated with the response to the cytokine growth hormone (GH). Studies in 3T3-F442A cells showing rapid GH-dependent tyrosyl phosphorylation of multiple proteins, tyrosyl phosphorylation of microtubule-associated protein kinases, and stimulation of microtubule-associated protein kinase activity, as well as the inhibition of these actions by inhibitors of growth hormone receptor (GHR)-associated tyrosine kinase (Campbell, G. S. et al., *J. Biol. Chem.* 268:7427–7434 (1993)), suggest a central role for a GHR-associated tyrosine kinase activity in signaling by GH. In addition, the presence of a tyrosine kinase activity in a complex with GH receptor (GHR) prepared from GH-treated fibroblasts has been reported (Carter-Su., C. et al., *J. Biol. Chem.* 264:18654–18661 (1989); Stred, S. E. et al., *Endocrinol.* 130:1626–1636 (1992); Wang, X. et al., *J. Biol. Chem.* 267:17390–17396 (1992)). More recently, a nonreceptor tyrosyl phosphorylated 122 kd protein was identified in a kinase-active GH-GHR preparation (Wang, X. et al., *J. Biol. Chem.* 268:3573–3579 (1993)).

To identify the spectrum of protein tyrosine kinases that are expressed in IL-3-dependent cells which might be involved in signal transduction, polymerase chain reactions (PCR) have been done with degenerative oligonucleotides to conserved protein tyrosine kinase domains (Wilks, A. F., *Methods Enzymol.* 200:533–546 (1991)). Using this approach and Northern blot analysis, IL-3 dependent cells have been shown to express the genes for a number of protein tyrosine kinases including lyn, Tec, c-fes, Jak1 and Jak2 (Mano, H., et al., *Oncogene* 8:417–424 (1993)). Whether these tyrosine kinases, or other as yet unidentified tyrosine kinases, are involved in cytokine signal transduction is largely unknown.

The potential involvement of lyn kinase in signal transduction was indicated by a recent studies that indicated that IL-3 stimulation increased lyn kinase activity in immune precipitates (Torigoe, T., et al., *Blood* 80:617–624 (1992)).

Two of the other tyrosine kinases expressed in IL-3-dependent cells, Jak1 and Jak2, belong to the Jak family of kinases. The Jak (Janus kinase; alternatively referred to as just another kinase) family of kinases were initially detected in PCR amplification of tyrosine kinase domains in hematopoietic cells (Wilks, A. F., *Proc. Natl. Acad. Sci. USA* 86:1603–1607 (1989)). These studies identified two closely related genes (FD17 and FD22; later termed Jak2 and Jak1) from which the major PCR amplification products were derived. The complete structure of the human Jak1 gene has been reported (Wilks, A. F., et al., *Mol. Cell. Biol.* 11:2057–2065 (1991)) and, recently, a partial sequence of the murine Jak2 gene was published (Harpur, A. G., et al., *Oncogene* 7:1347–1353 (1992)). Independently a third member of the family (Tyk2) was isolated by screening a cDNA library with a tyrosine kinase domain probe from the c-fms gene (Firmbach-Kraft, I., et al., *Oncogene* 5:1329–1336 (1990)). The family is characterized by the presence of two kinase domains, one of which is a carboxyl domain that has all the hallmarks of protein kinases. The second domain is immediately amino terminal and bears all the hallmarks of a protein kinase but differs significantly from both the protein tyrosine and serine/threonine kinases. Amino terminal to the kinase domains, there are no SH2 and SH3 domains that characterize most of the non-receptor tyrosine kinases. However, there is extensive similarity in this region among the Jak family members and a number of homology domains have been defined (Harpur, A. G., et al., *Oncogene* 7:1347–1353 (1992)).

A link between one member of the Jak family of kinases and the signal transduction of interferon alpha (IFNα) has been recently reported (Velazquez, L., et al., *Cell* 70:313–322 (1992); Fu, X. Y., *Cell* 70:323–335 (1992); Schindler, C., et al., *Science* 257:809–813 (1992)). Using a genetic approach, the Tyk2 gene was cloned by its ability to functionally reconstitute the cellular response to IFNα in a mutant human cell line that was unresponsive to IFNα. No other link between Tyk2, or any other member of the Jak kinase family, and the signal transduction of any cytokine other than IFNα has been reported.

SUMMARY OF THE INVENTION

The present invention is based in part upon the discovery that the cellular response to several cytokines, particularly those cytokines which function by binding to members of the cytokine receptor superfamily, is mediated by the activation (i.e. phosphorylation) of a member of the Jak kinase family. According to the invention, Jak kinases mediate cytokine activity through their tyrosine phosphorylation (i.e. activation) in response to cytokine-receptor binding.

The present invention is drawn in part to novel methods for regulating cytokines whose activity is mediated by the activation of a Jak kinase.

One object of the present invention is to provide methods for inhibiting the cellular response to cytokines whose activity is mediated by activation of Jak2 kinase activity.

Another object of the present invention is to provide methods for treating disease conditions caused by an excessive response to a cytokine whose activity is mediated by the activation of a Jak kinase, such as cytokine induced excessive proliferation of eukaryotic cells.

Yet another object of the present invention is to provide assays for identifying compositions capable of inhibiting the biological response of a eukaryotic cell to a cytokine whose activity is mediated by the activation of a Jak kinase.

Yet another object of the present invention is to provide a method for enhancing the biological response of a eukaryotic cell to a cytokine whose activity is mediated by the activation of Jak2 kinase activity.

Yet another object of the present invention is to provide antibodies useful for detecting and extracting a particular Jak protein without interfering with its kinase activity.

According to one aspect of the invention, particular cytokines whose activity is mediated by Jak2 kinase are identified, including interleukin-3 (IL-3), granulocyte-macrophage specific colony stimulating factor (GM-CSF), erythropoietin (Epo), granulocyte colony stimulating factor (G-CSF), interferon-γ (IFN-γ), prolactin hormone and growth hormone.

The present invention is also based on the elucidation of the complete DNA and amino acid sequence for Jak2 kinase. Accordingly, another object of the invention is to provide gene sequences coding for the entire Jak2 kinase, expression vehicles containing the gene sequence capable of expressing the full-length Jak2 kinase, and hosts transformed therewith.

BRIEF DESCRIPTION OF THE DRAWINGS

FIGS. 1A–1H. Sequence of the murine Jak2 cDNA

Figure 4:
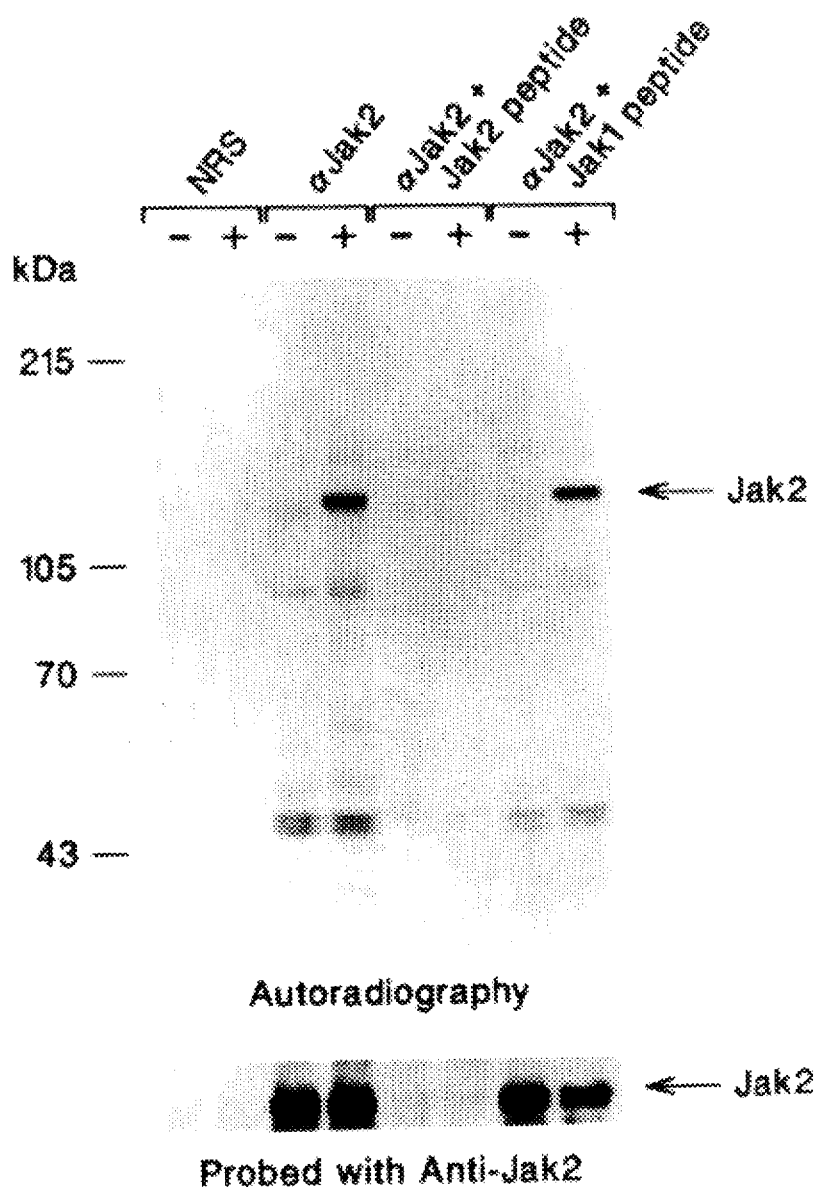

The nucleotide sequence of the Jak2 open reading frame and flanking non-coding regions is shown (SEQ ID No. 8). The single letter amino acid sequence is shown below (SEQ ID No. 9). Nucleotide and amino acid sequence information from the published partial Jak2 cDNA sequence (Harpur, A. G., et al., *Oncogene* 7:1347–1353 (1992)) is shown above and below the sequences provided where that information is different. The ATG codons are indicated (*). The arrow (>) above nucleotide 522 designates the 5' end of the reported Jak2 sequence. The arrow (^) at nucleotide position 2226 indicates the location of a 7 amino acid insert, detected in previous studies (Harpur, A. G., et al., *Oncogene* 7:1347–1353 (1992)). The nucleotides in parenthesis in the 3' non-coding region were present in the previous studies (Harpur, A. G., et al., *Oncogene* 7:1347–1353 (1992)) and not detected in our studies.

FIGS. 2A–2D. Sequence of the human Jak1 amino acid and DNA coding sequence

The published amino acid (SEQ ID No. 11) and DNA coding sequence (SEQ ID No. 10) for human Jak1 kinase is shown (Wilks, A. F. et al., *Mol. Cell. Biol.* 11:2057–2065 (1991)). Nucleotide numbering is retained from the published sequence, with the coding sequence beginning at nucleotide 76 and ending at nucleotide 3504.

FIGS. 3A–3E. Sequence of the human Tyk2 amino acid and DNA coding sequence

The published amino acid (SEQ ID No. 13) and DNA coding sequence (SEQ ID No. 12) for human Tyk2 kinase is shown (Firmbach-Kraft, I. et al., *Oncogene* 5:1329–1336 (1990)). Nucleotide numbering is retained from the published sequence, with the coding sequence beginning at nucleotide 307 and ending at nucleotide 3867.

FIG. 4. IL-3 Stimulation Activates Jak2 In Vitro Kinase Activity in Immunoprecipitates DA-3 cells were removed from growth factors and were either unstimulated (−) or stimulated (+) with IL-3 for 10 min as described in Materials and Methods. Cell extracts were then immunoprecipitated with normal rabbit serum (NRS) or the antipeptide antiserum specific for Jak2 in the absence of competing peptide (αJak2) or in the presence of the peptide (30 μg/ml) to which the antiserum was raised (αJak2+Jak2 peptide) or in the presence of an equivalent amount of the peptide that corresponds to the comparable region of Jak1 (αJak2+Jak1 peptide). The immunoprecipitates were used for in vitro kinase assays as described in Methods and Materials (Example 1). The products of the reactions were resolved by SDS-PAGE, transferred to nitrocellulose and detected by autoradiography (top panel). The blots were subsequently probed with the antiserum against Jak2 (bottom panel).

FIGS. 5A–5E. Comparison of Jak Kinase Amino Acid Sequences

An alignment of the amino acid sequences of Jak1 (line 1; SEQ ID NO. 14)), Tyk2 (line 2; SEQ ID NO. 13), and Jak2 (line 3; SEQ ID NO. 9)), along with the consensus sequence (line 4) generated using the Intelligenetics computer program "Pileup" is shown (Plurality=2.00; Threshold=1.00; AveWeight=1.00; AveMatch=0.54; AvMisMatch=−0.4).

DETAILED DESCRIPTION OF THE INVENTION

One aspect of the present invention is directed to novel methods for regulating the cellular response to cytokines. These methods are based upon the general role of the Jak family of kinases in the cellular response to several cytokines revealed by the present invention.

By "cytokine" is meant any polypeptide secreted by cells that affects the function of other cells. Examples of cytokines include, among others, peptide hormones and growth factors.

By "cellular response to a cytokine" or "cytokine activity" is meant the general biological effect upon a eukaryotic cell or cell population which ultimately results from the association of a particular cytokine with its cellular receptor and typically involves the modification of gene expression within the cell. The invention relates to cytokine activity which is mediated by the activation of a Jak kinase. Examples of such activity include, but are not limited to, the proliferation and differentiation of hematopoietic progenitor cells in response to interleukin-3 (IL-3), the proliferation and differentiation of erythroid lineage cells in response to erythropoietin (Epo), somatic cell growth in response to growth hormone (GH), etc.

The methods taught by the invention apply to any cytokine whose activity is mediated by a member of the Jak kinase family, which includes Jak1, Jak2, and Tyk2. Cytokines of this type include those which function by binding to members of the cytokine receptor superfamily, and also those which function by binding to members of the tyrosine kinase receptor superfamily. More specifically, these cytokines include, but are not limited to, interleukin-3 (IL-3), granulocyte-macrophage specific colony stimulating factor (GM-CSF), erythropoietin (Epo), granulocyte colony stimulating factor (G-CSF), interferon-γ (IFN-γ), prolactin hormone and growth hormone.

According to the invention, Jak kinases mediate cytokine activity through their tyrosine phosphorylation (i.e. activation) in response to cytokine-receptor binding. Thus, cytokines susceptible to the methods of regulation provided by the present invention may be identified on the basis of their ability to cause the tyrosine phosphorylation (i.e. activation) of one or more members of the Jak kinase family. Tyrosine phosphorylation of a Jak kinase in a cell following cytokine stimulation may be detected, for example, by assaying for its ability to bind antiphosphotyrosine monoclonal antibody; only tyrosine phosphorylated Jak kinases will bind this type of antibody. Alternatively, in vitro kinase assays as described below may be used to determine the state of activation (tyrosine phosphorylation) of a Jak kinase in a cell following cytokine stimulation.

Methods for Inhibiting Cytokine Activity Dependent Upon Jak kinases

According to the invention, the activity of a cytokine may be inhibited by inhibiting the activity of the Jak kinase which mediates that cytokine's effect upon the cell.

One way of inhibiting Jak kinase activity within the scope of the present invention is by inhibiting Jak gene expression. Expression of Jak kinases may be inhibited using antisense molecules or ribozymes.

Antisense molecules and their use for inhibiting gene expression are well known in the art (see, for example, Cohen, J., *Oligodeoxyribonucleotides, Antisense Inhibitors of Gene Expression*, CRC Press (1989); Toole, WO 92/10590). Antisense molecules useful for inhibiting the expression of a Jak kinase contain nucleic acid sequences complementary to, and capable of binding to, the mRNA and/or DNA gene sequence of the Jak kinase desired to be inhibited. Such antisense molecules may be provided to the cell via genetic expression using DNA encoding the antisense molecule as taught by U.S. Pat. No. 5,190,931, issued Mar. 2, 1993 to Inoue, M. (incorporated by reference herein in its entirety). Alternatively, antisense molecules of the invention may be made synthetically and then provided to the cell. Synthetic antisense molecules contemplated by the invention include oligonucleotide derivatives known in the art which have improved biological activity compared to unmodified oligonucleotides (see Cohen, J., supra; U.S. Pat. No. 5,023,243, issued Jun. 11, 1991 to Tullis, R. H. and incorporated by reference herein in its entirety).

Ribozymes and their use for inhibiting gene expression are also well known in the art (see, for example, Cech et al., *J. Biol. Chem.* 267:17479–17482 (1992); Hampel et al., *Biochemistry* 28:4929–4933 (1989); Haseloff et al., *Nature* 334:585–591 (1988); Eckstein et al., WO 92/07065; and U.S. Pat. No. 5,168,053 issued to Altman et al. and incorporated by reference herein in its entirety). Like antisense molecules, ribozymes contain target sequences complementary to the mRNA of the genes whose expression they are designed to inhibit. Ribozymes useful for inhibiting the expression of a Jak kinase may be designed by incorporating target sequences into the basic ribozyme structure which are complementary to the mRNA sequence of the Jak kinase desired to be inhibited. Ribozymes targeting a Jak kinase may be synthesized using commercially available reagents (Applied Biosystems) or they may be genetically expressed from DNA encoding them.

As will be recognized by the skilled artisan, antisense and ribozyme molecules may be designed to inhibit a specific member of the Jak kinase family by targetting sequences unique to that member. Alternatively, antisense and ribozyme molecules may be designed to inhibit more than one Jak kinase by targetting sequences shared by the Jak members desired to be inhibited.

Jak kinase activity may also be inhibited through the use of compounds or peptides which inhibit the ability of the Jak protein to function as a kinase. Such inhibitors include, but are not limited to, drugs, anti-Jak kinase antibody, Jak kinase agonists and antagonists, trans-dominant mutants of Jak kinase, and general inhibitors of tyrosine kinase activity such as genestein. These inhibitors may have a general inhibitory effect upon all Jak kinases or they may possess a more specific inhibitory effect upon a specific member or subset of the Jak kinase family.

The term "antibody", as used herein, refers both to monoclonal antibodies which are a substantially homogeneous population and to polyclonal antibodies which are heterogeneous populations. Such antibodies may be of any immunoglobulin class including IgG, IgM, IgE, IgA, IgD and any subclass thereof. The term "antibody", as used herein, is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)). Such fragments are typically produced by proteolytic cleavage, using enzymes such as papain (to produce Fab fragments) or pepsin (to produce F(ab')$_2$ fragments).

Both monoclonal and polyclonal antibodies to Jak kinase may be made according to methods well known in the art (see, for example, Ausubel, F. M. et al., *Current Protocols in Molecular Biology*, published by Current Protocols, pp. 11.4.2–11.13.4 (1993)). Antibodies may be generated against Jak kinase protein produced recombinantly or isolated from cells and tissues where the Jak kinase naturally occurs. Antibodies may be generated against the entire Jak kinase protein or, more preferably, antibodies are generated against peptide subfragments representing functional domains of the Jak kinase protein required for its cytokine-induced tyrosine kinase activity. Antibodies for specifically inhibiting a particular Jak kinase may be generated against peptide fragments unique to that Jak kinase. Alternatively, antibodies for generally inhibiting more than one member of the Jak kinase family may be generated against peptide fragments shared by the Jak kinases desired to be inhibited.

Another method for inhibiting Jak kinase activity taught by the invention is through the use of inhibitors of the cytokine-dependent activation of the Jak kinase. Prior to cytokine stimulation, cellular Jak kinase is present in an inactivated state. Inhibitors of Jak kinase activation may be identified by their ability to inhibit the conversion of the Jak kinase into its catalytically active state, which can be detected by in vitro kinase assay as described below and in the Examples.

As discovered by the present inventors, Jak kinases are activated by their cytokine-induced tyrosine phosphorylation. Accordingly, inhibitors may also be identified according to the invention as those compounds or peptides which block or significantly reduce the cytokine-induced tyrosine phosphorylation of the Jak kinase into its catalytically active form. The state of tyrosine phosphorylation of a Jak kinase following cytokine stimulation may be assayed, for example, by the ability of the Jak kinase to be detected with an antiphosphotyrosine monoclonal antibody.

Activation of a Jak kinase by a particular cytokine may require the physical association of the Jak kinase with the receptor for that cytokine (see Example 2). According to the invention, peptide antagonists mimicking those portions of the Jak kinase or cytokine receptor involved in this association are useful as inhibitors of Jak kinase activation. These peptides are contemplated by the invention to act as inhibitors by associating with either the cytokine receptor (for the Jak kinase peptides) or the Jak kinase (for the cytokine receptor peptides), thus blocking the association of the Jak kinase with the cytokine receptor.

In particular, the invention teaches that Jak2 activation by Epo requires the physical association of Jak2 with the Epo receptor (EpoR) and that this association requires a membrane proximal region of EpoR that is essential for mitogenesis. According to the invention, peptide antagonists mimicking this membrane proximal region and capable of blocking the EpoR-Jak2 interaction are useful as inhibitors of Jak2 activation by Epo.

Assays for Inhibitors of Jak kinase activity

The present invention also provides screening assays for identifying inhibitors of Jak kinase activity useful in the methods described herein above.

Jak tyrosine kinase activity can be assayed in vitro by combining catalytically active Jak kinase, a Jak phosphorylation substrate(s), and ATP with the phosphorous at the γ position delectably labelled with, for example, a radiolabel such as $^{32}$P. In this assay, the Jak kinase catalyzes the transfer of the labelled phosphorous from ATP to the substrate and Jak kinase activity is detected by the generation of substrate containing detectably labelled phosphorous (i.e. labelled substrate). Inhibitors of Jak kinase activity are identified as those compounds or peptides which, when incorporated into the assay, significantly reduce or eliminate the generation of labelled substrate.

Catalytically active Jak kinase for use in this assay may be obtained from a variety of sources. Preferably, a catalytically active Jak kinase is obtained from insect cells transformed with a baculovirus vector capable of expressing the Jak kinase at high levels. Jak2 kinase produced in this way has been found to be catalytically active and useful in in vitro kinase assays. It is expected that other Jak kinases produced in large amounts in insect cells in a similar manner will also be catalytically active.

A catalytically active Jak kinase may also be obtained from cells carrying mutations which result in constitutive activation of the Jak kinase. For example, an EpoR mutation known as $R^{199}$->C results in constitutive activation of the EpoR (Yoshimura et al., Nature 348:647–649 (1990)). In cells expressing this mutation, in the absence of Epo, Jak2 kinase is constitutively tyrosine phosphorylated and possesses in vitro kinase activity.

Catalytically active forms of each Jak kinase may also be obtained from cells stimulated with a cytokine which causes their activation. For example, catalytically active Jak2 kinase may be obtained from cells stimulated with Epo, growth hormone, IL-3, etc., while catalytically active Tyk2 may be obtained from cells stimulated with IFNα.

Any phosphorylation substrate of the Jak kinase whose activity is being determined may be used in the assay. For a Jak kinase which possesses autophosphorylation activity, a preferred substrate is the Jak kinase itself, or a subfragment thereof containing the autophosphorylation site. Tyrosine kinases such as the Jak kinases generally tend to possess autophosphorylation activity (see, for example, Hanks, S. K. et al., Science 241:42–52 (1988). Moreover, autophosphorylation activity for Jak2 has been established and the autophosphorylation site has been found to reside on a peptide fragment containing amino acids 1000–1015 of Jak2 (see FIG. 1; the sequence is VLPQDKEYYKVKEPG (SEQ ID No. 2)). Similar peptides fragments exist in the Jak1 protein at amino acids 1015–1029 (see FIG. 2; the sequence is AIETDKEYYTVKDDR (SEQ ID NO. 3)) and in the Tyk2 protein at amino acids 1047–1061 (see FIG. 3; the sequence is AVPEGHEYYRVREDG (SEQ ID No. 4)). Based on structural and functional similarities among the Jak kinases, as well as functional similarities among tyrosine kinases in general, it is expected that the other members of the Jak kinase family also possess autophosphorylation activity.

The present invention also provides an assay for inhibitors of cytokine-induced activation of a Jak kinase. Cytokine-induced activation of a Jak kinase can be assayed by preparing Jak kinase extracts from cells following cytokine induction and assaying the extracts for in vitro kinase activity as described herein. Inhibitors of cytokine-induced activation of a Jak kinase are identified as those compounds or peptides which, when present in the cells before and/or during cytokine induction, significantly reduce or eliminate the in vitro kinase activity detected in the Jak kinase extracts prepared from the cells following cytokine induction.

The present invention also provides an assay for inhibitors of Jak kinase-cytokine receptor interactions which are potential inhibitors of cytokine-induced Jak kinase activation. For those cytokine receptors which are phosphorylated by an activated Jak kinase, the Jak kinase-cytokine receptor interaction may be detected using the in vitro kinase assay described above by incorporating the cytokine receptor into the assay as the phosphorylation substrate. For example, phosphorylation of the erythropoietin receptor (EpoR) by Jak2 kinase may be detected using this assay. Inhibitors of the Jak kinase-cytokine receptor interactions are identified as those compounds or peptides which, when incorporated into this assay, significantly reduce or eliminate the generation of phosphorylated (labelled) cytokine receptor protein.

Cytokine receptor protein is preferably obtained for use in this assay by production and purification from a recombinant host suitable for such purposes as described herein for the production of Jak kinases. A preferable host is insect cells transformed with a baculovirus vector capable of expressing cytokine receptor at high levels. Alternatively, cytokine receptor protein may be isolated from natural sources.

Methods for Enhancing Cytokine Activity Dependent Upon Jak kinases

In those situations where the biological response of a cell to a cytokine is deficient due to insufficient amounts of a Jak kinase, the present invention provides for enhancing this response by increasing the levels of the Jak kinase in the cell (see Example 4). This situation could be due to mutations which reduce the amount of the Jak kinase produced by the cell to sub-normal levels. This situation could also be due to mutations which reduce the rate or degree of cytokine-induced Jak activation such that the level of Jak kinase produced by the cell does not provide sufficient levels of activated Jak kinase following cytokine induction.

The levels of Jak kinase may be increased in a cell by adding Jak kinase protein to the cell, or by introducing a vector into the cell capable of expressing the Jak kinase. Vectors and methods for the expression of Jak2 are provided below. As will be readily apparent to one of skill in the art, these methods may also be applied to the production and expression of other members of the Jak kinase family.

Therapeutic Applications Of The Methods For Regulating Cytokine Activity

It is also contemplated by the invention that methods provided for regulating Jak kinase activity as described above may be applied to treating disease conditions caused by an abnormal cellular response to a cytokine whose activity is mediated by the activation of a Jak kinase. Thus disease conditions caused by an excessive cellular response to a cytokine whose activity is mediated by the activation of a Jak kinase may be treated by inhibiting Jak kinase activity. In particular, disease conditions caused by excessive proliferation of eukaryotic cells may be treated by inhibiting Jak kinase activity where this excessive proliferation occurs in response to a cytokine whose activity is mediated by the activation of a Jak kinase. Such disease conditions are caused by genetically acquired mutations or spontaneously acquired mutations.

For example, erythrocytosis is a genetically acquired disease that involves excess proliferation of erythrocytes from progenitor cells. The overproduction is dependent upon erythropoietin (Epo) and is caused by a mutation in the Epo receptor (EpoR) that results in the abnormal regulation of Jak2 kinase activity through Epo-EpoR binding. Comparable mutations may also occur spontaneously and give rise to this disease condition. In addition, analogous disease conditions may occur in other cell lineages that are regulated through a Jak kinase mediated cytokine response.

Alternatively, disease conditions caused by a deficient cellular response, or nonresponsiveness, to a cytokine whose activity is mediated by the activation of a Jak kinase may be treated by enhancing Jak kinase activity.

It is contemplated by the invention that administration of the compositions as described herein capable of inhibiting Jak kinase activity, including antisense molecules, ribozymes, Jak antibodies, antagonists, etc. may be accomplished by any of the methods known to the skilled artisan. For example, administration may be by parenteral, subcutaneous, intravenous, intramuscular, intra-peritoneal, or transdermal routes, administered in a pharmaceutically acceptable carrier by any means recognized as suitable by the skilled artisan.

Administration will ordinarily include an efficacious amount of the inhibitory composition supplied in a pharmaceutically acceptable vehicle. The amount of the inhibitory composition which is efficacious will be determined by a trained professional depending upon a number of considerations, including the condition being treated and its severity, the sex and body weight of the subject being treated, the method and frequency of administration, the potency of the inhibitory composition, and the presence of compositions in the pharmaceutically acceptable vehicle which affect the potency of the inhibitory composition.

Antibodies Capable of Binding To Specific Jak Proteins Without Interfering With Kinase Activity The present invention also provides antibodies useful for detecting and extracting specific Jak kinases from eukaryotic cells without disrupting their kinase activity. These antibodies are generated against a peptide fragment representing a portion of the Jak hinge region between domains 1 and 2 that is different for each Jak kinase. Peptides useful for generating such antibodies are derived from amino acids 758–776 of Jak2 (FIG. 1; the sequence is DSQRKLQFYEDKHQL-PAPK (SEQ ID No. 5)), amino acids 786–804 of Jak1 (FIG. 2; the sequence is TLIEKERFYESRCRPVTPS (SEQ ID No. 6)), and amino acids 819–837 of Tyk2 (FIG. 3; the sequence is SPSEKEHFYQRQHRLPEPS (SEQ ID No. 7)). According to the invention antibodies generated against these peptides can specifically bind to and recognize the Jak protein from which the peptide antigen was derived without interfering with kinase activity.

Through the application of standard immunoprecipitation techniques, these antibodies can be used to obtain cell extracts containing a specific Jak protein for use in the in vitro kinase assay. Such a use is demonstrated for antibody generated against the hinge region of Jak2 kinase in Examples 1–3 and 5.

The Jak2 Gene and Protein

According to the present invention, the complete cDNA sequence and amino acid sequence of murine Jak2 kinase is provided. The nucleotide sequence of a full-length Jak2 cDNA is provided in FIG. 1 (SEQ ID No. 8) and contains an open reading frame (ORF) of 3387 bp encoding the Jak2 protein, which is 1129 amino acids long and has a calculated molecular weight of 130 kDa. The 5' end of the Jak2 cDNA in FIG. 1 has three stop codons before the first ATG. Although the first ATG does not fulfill the Kozak consensus flanking sequences, it is immediately followed by an ATG codon in the typical translation initiation environment (Kozak, M., Nucl. Acids Res. 15:8125–8148 (1987)). The 5' end does not contain an obvious signal peptide. The compiled size of the 3' untranslated region of the Jak2 clones is 0.9 kb which corresponds to a 4.4 kb transcript.

The process for genetically engineering Jak2 kinase, according to the invention, is facilitated through the cloning of DNA encoding Jak2 kinase and through the expression of such sequences. DNA encoding Jak2 kinase may be derived from a variety of sources according to the invention, including genomic DNA, cDNA, synthetic DNA, and combinations thereof.

Genomic DNA may or may not include naturally occurring introns. Moreover, such genomic DNA may be obtained in association with the 5' promoter region of the Jak2 gene sequences. The 5' promoter region may be retained and employed for expression of Jak2 in those host cells which recognize the expression signals present in this promoter region.

Genomic DNA or cDNA, which does not contain introns, may be obtained in several ways. Genomic DNA can be extracted and purified from suitable cells by means well known in the art. Alternatively, messenger RNA (mRNA) may be isolated from a cell which produces Jak2 kinase and used to prepare cDNA by means well known in the art. Such suitable DNA preparations are enzymatically cleaved, or randomly sheared, and ligated into recombinant vectors to form either a genomic or cDNA sequence library (see Ausubel, F. M. et al., Current Protocols in Molecular Biology, published by Current Protocols, pp. 5.0.3–5.10.2 (1993)). Such libraries can then be screened for hybridization with nucleic acid probes based upon the Jak2 gene sequence provided in FIG. 1 (SEQ ID NO. 8) in order to identify and isolate cloned Jak2 encoding sequences (see Ausubel, F. M. et al. supra, pp. 6.0.3–6.6.1). The members of the library identified by this screen are then analyzed to determine the extent and nature of the Jak2 sequences they contain.

In lieu of the above-described recombinant methods, a gene sequence encoding Jak2 kinase can be prepared synthetically according to methods well known in the art (see Ausubel, F. M. et al., supra, pp. 2.11.1–2.11.18).

The cloned Jak2 encoding sequences, obtained through the methods described above, may be operably linked to an expression vector and introduced into a bacterial or eukaryotic cell to produce Jak2 kinase. Techniques for such manipulations are well known in the art and are disclosed in Ausubel, F. M. et al., supra, at pp. 3.0.3–3.16.11.

A DNA is said to be "capable of expressing" a polypeptide if it contains nucleotide sequences which contain transcriptional and translational regulatory information and such sequences are "operably linked" to nucleotide sequences encoding the polypeptide. An operable linkage is a linkage in which the regulatory DNA sequences and the DNA coding sequence sought to be expressed are connected in such a way as to permit expression of the coding sequence. The precise nature of the regulatory regions needed for gene expression may vary from organism to organism, but shall generally include a promoter region which, in prokaryotes, contains both the promoter (which directs the initiation of RNA transcription) as well as the DNA sequences which, when transcribed into RNA, will signal the initiation of translation of the coding sequence. Such regions will normally include those 5'-non-coding sequences involved with initiation of transcription and translation, such as the TATA box, capping sequence, CAAT sequence, and the like.

If desired, the non-coding region 3' to the gene sequence coding for the Jak2 kinase may be obtained by the above-described methods. This region may be retained for its regulatory sequences, such as transcriptional termination and polyadenylation signals. Thus by retaining the 3'-region naturally contiguous to the DNA sequence coding for Jak2 kinase, these regulatory regions may be provided. Where the regulatory signals are not satisfactorily functional in the expression host cell, then a 3' region functional in the host cell may be substituted.

To express the Jak2 kinase in a prokaryotic cell (such as, for example, E. coli, B. subtilis, Pseudomonas, Streptomyces, etc.), it is necessary to operably link the Jak2 kinase encoding sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, etc. Examples of inducible prokaryotic promoters include the major right and left promoters of bacteriophage λ ($P_L$ and $P_R$), the trp, recA, lacZ, lacI, and gal promoters of E. coli, the α-amylase (Ulmanen, I., et al., J. Bacteriol. 162:176–182

(1985)) and the σ-28-specific promoters of *B. subtilis* (Gilman, M. Z., et al., *Gene sequence* 324:11–20 (1984)), the promoters of the bacteriophages of Bacillus (Gryczan, T. J., In: *The Molecular Biology of the Bacilli*, Academic Press, Inc., NY (1982)), and Streptomyces promoters (Ward, J. M., et al., *Mol. Gen. Genet.* 203:468–478 (1986)). Prokaryotic promoters are reviewed by Glick, B. R., *J. Ind. Microbiol.* 1:277–282 (1987); Cenatiempo, Y., *Biochimie* 68:505–516 (1986); and Gottesman, S., *Ann. Rev. Genet.* 18:415–442 (1984).

Proper expression in a prokaryotic cell also requires the presence of a ribosome binding site upstream of the gene sequence-encoding sequence. Such ribosome binding sites are disclosed, for example, by Gold, L., et al., *Ann. Rev. Microbiol.* 35:365–404 (1981).

Preferred eukaryotic hosts include yeast, fungi, insect cells, mammalian cells either in vivo, or in tissue culture. Mammalian cells which may be useful as hosts include, but are not limited to, COS cells and cells or cell lines derived from fibroblasts, myeloid leukemias, or normal hematopoietic tissues.

For a mammalian host, several possible vector systems are available for the expression of the Jak2 kinase. A wide variety of transcriptional and translational regulatory sequences may be employed, depending upon the nature of the host. The transcriptional and translational regulatory signals may be derived from viral sources, such as adenovirus, bovine papilloma virus, Simian virus, or the like, where the regulatory signals are associated with a particular gene sequence which has a high level of expression. Alternatively, promoters from mammalian expression products, such as actin, collagen, myosin, etc., may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

A preferred host for production of catalytically active Jak kinases is insect cells, for example the Drosophila larvae. Using insect cells as hosts, the Drosophila alcohol dehydrogenase promoter can be used (Rubin, G. M., *Science* 240:1453–1459 (1988)). Alternatively, baculovirus vectors can be engineered to express large amounts of Jak2 kinase in insects cells (see, for example, Ausubel, F. M. et al., *Current Protocols in Molecular Biology*, published by Current Protocols, pp. 16.8.1–16.11.7 (1993); Jasny, B. R., *Science* 238:1653 (1987); Miller, D. W., et al., in *Genetic Engineering* (1986), Setlow, J. K., et al., eds., Plenum, Vol. 8, pp. 277–297). Expression of Jak2 kinase in insect cells from baculovirus vectors produces activated Jak2 kinase which may be used in screening assays for inhibitors of Jak2 kinase activity as described above.

As discussed above, expression of the Jak2 kinase in eukaryotic hosts requires the use of eukaryotic regulatory regions. Such regions will, in general, include a promoter region sufficient to direct the initiation of RNA synthesis. Preferred eukaryotic promoters include the promoter of the mouse metallothionein I gene sequence (Hamer, D., et al., *J. Mol. Appl. Gen.* 1:273–288 (1982)); the TK promoter of the Herpes virus (McKnight, S., *Cell* 31:355–365 (1982)); the SV40 early promoter (Benoist, C., et al., *Nature* (London) 290:304–310 (1981)); the yeast gal4 gene sequence promoter (Johnston, S. A., et al., *Proc. Natl. Acad. Sci. (USA)* 79:6971–6975 (1982); Silver, P. A., et al., *Proc. Natl. Acad. Sci. (USA)* 81:5951–5955 (1984)); and the 9–27 gene promoter (Reid, L. E., et al., *Proc. Natl. Acad. Sci. USA* 86:840–844 (1989)).

As is widely known, translation of eukaryotic mRNA is initiated at the codon which encodes the first methionine. For this reason, it is preferable to ensure that the linkage between a eukaryotic promoter and a DNA sequence which encodes the Jak2 kinase does not contain any intervening codons which are capable of encoding a methionine (i.e., AUG). The presence of such codons results either in a formation of a fusion protein (if the AUG codon is in the same reading frame as the Jak2 kinase encoding DNA sequence) or a frame-shift mutation (if the AUG codon is not in the same reading frame as the Jak2 kinase encoding sequence).

The Jak2 kinase encoding sequence and an operably linked promoter may be introduced into a recipient prokaryotic or eukaryotic cell either as part of a nonreplicating DNA (or RNA) molecule, which may either be a linear molecule or, more preferably, a closed covalent circular molecule. Since such molecules are incapable of autonomous replication, the expression of the Jak2 kinase may occur through the transient expression of the introduced sequence. Alternatively, permanent expression may occur through the integration of the introduced sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, H., *Molec. Cell. Biol.* 3:280 (1983).

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, πVX. Such plasmids are, for example, disclosed by Maniatis, T., et al. (In: *Molecular Cloning, A Laboratory Manual*, Cold Spring Harbor Press, Cold Spring Harbor, N.Y. (1982)). Bacillus plasmids include pC194, pC221, pT127, etc. Such plasmids are disclosed by Gryczan, T. (In: *The Molecular Biology of the Bacilli*, Academic Press, NY (1982), pp. 307–329). Suitable Streptomyces plasmids include pIJ101 (Kendall, K. J., et al., *J. Bacteriol.* 169:4177–4183 (1987)), and streptomyces bacteriophages such as φC31 (Chater, K. F., et al., In: *Sixth International Symposium on Actinomycetales Biology,*

Akademiai Kaido, Budapest, Hungary (1986), pp. 45–54). Pseudomonas plasmids are reviewed by John, J. F., et al. (*Rev. Infect. Dis.* 8:693–704 (1986)), and Izaki, K. (*Jpn. J. Bacteriol.* 33:729–742 (1978)).

Preferred eukaryotic plasmids include BPV, vaccinia, SV40, 2-micron circle, etc., or their derivatives. Such plasmids are well known in the art (Botstein, D., et al., *Miami Wntr. Symp.* 19:265–274 (1982); Broach, J. R., In: *The Molecular Biology of the Yeast Saccharomyces: Life Cycle and Inheritance*, Cold Spring Harbor Laboratory, Cold Spring Harbor, N.Y., p. 445–470 (1981); Broach, J. R., *Cell* 28:203–204 (1982); Bollon, D. P., et al., *J. Clin. Hematol. Oncol.* 10:39–48 (1980); Maniatis, T., In: *Cell Biology: A Comprehensive Treatise*, Vol. 3, *Gene sequence Expression*, Academic Press, NY, pp. 563–608 (1980)).

Once the vector or DNA sequence containing the construct(s) has been prepared for expression, the DNA construct(s) may be introduced into an appropriate host cell by any of a variety of suitable means: transformation, transfection, conjugation, protoplast fusion, electroporation, calcium phosphate-precipitation, direct microinjection, etc. After the introduction of the vector, recipient cells are grown in a selective medium, which selects for the growth of vector-containing cells. Expression of the cloned gene sequence(s) results in the production of the Jak2 kinase.

Expressed Jak2 kinase may be isolated and purified as described herein, using conventional methods such as extraction, precipitation, immunoprecipitation, chromatography, affinity chromatography, electrophoresis, or the like.

EXAMPLES

Example 1

Structure of the Murine Jak2 Protein Tyrosine Kinase and Its Role In IL-3 Signal Transduction Summary Interleukin 3 (IL-3) regulates the proliferation and differentiation of a variety of hematopoietic cells including early progenitors and cells committed to various lineages. The receptor for IL-3 consists of α and β subunits that together are required for the expression of a high affinity receptor. The IL-3 receptor chains are members of the cytokine receptor family and contain cytoplasmic domains that lack identifiable kinase catalytic domains. However, IL-3 binding rapidly induces tyrosine phosphorylation of the β chain of the receptor as well as a number of cellular proteins. To investigate the potential role of the Jak family of protein tyrosine kinases in IL-3 signal transduction, we have obtained full-length cDNA clones for murine Jak1 and Jak2 and prepared antiserum against the predicted proteins. Using antisera against Jak2 we demonstrate that IL-3 stimulation results in the rapid and specific tyrosine phosphorylation of Jak2 and activates its in vitro kinase activity. These results support the hypothesis that Jak2 couples IL-3 binding to tyrosine phosphorylation and ultimately to the biological responses mediated by IL-3.

Introduction

Hematopoiesis is regulated through the interaction of a variety of growth factors with their cognate receptors (Metcalf, D., *Nature* 339:27–30 (1989); Clark and Kamen, *Science* 236:1229–1237 (1987)). Among the known hematopoietic growth factors, interleukin-3 (IL-3) supports the proliferation and differentiation of early progenitors as well as cells that are committed to several of the myeloid lineages (Ihle, J. N., in *Interleukins: Molecular Biology and Immunology*, Kishimoto, T., ed., Karger, Basel, pp. 65–106 (1992)). The receptor for IL-3 has been shown to be composed of two subunits, an α subunit of 60–70 kDa and β subunit of 130–140 kDa which are required for high affinity binding of IL-3 (Miyajima, A., et al., *Annu. Rev. Immunol.* 10:295–331 (1992)). Both the α and β subunits contain the extracellular conserved motifs found in the cytokine receptor superfamily. Similar to other members of this superfamily, the cytoplasmic domains of the receptor subunits share only a limited similarity with other cytokine receptors and lack any detectable catalytic domains that might suggest a signal transducing mechanism. In spite of the lack of catalytic domains, considerable evidence suggests that signal transduction involves tyrosine phosphorylation (Metcalf, D., *Nature* 339:27–30 (1989); Miyajima, A., et al., *Annu. Rev. Immunol.* 10:295–331 (1992)). Specifically, activated tyrosine kinases can abrogate the requirement for IL-3 and IL-3 rapidly induces the tyrosine phosphorylation of several cellular substrates as well as the β subunit of the IL-3 receptor complex. For these reasons there has been considerable interest in identifying a protein tyrosine kinase that may associate with the receptor and be activated by ligand binding.

To identify the spectrum of protein tyrosine kinases that are expressed in IL-3 dependent cells which might be involved in signal transduction, polymerase chain reactions (PCR) have been done with degenerative oligonucleotides to conserved protein tyrosine kinase domains (Wilks, A. F., *Methods Enzymol.* 200:533–546 (1991)). Using this approach and Northern blot analysis, IL-3 dependent cells have been shown (Mano, H., et al., *Oncogene* 8:417–424 (1993)) to express the genes for a number of protein tyrosine kinases including lyn, Tec, c-fes, Jak1 and Jak2. The potential involvement of lyn kinase in signal transduction was indicated by a recent study that indicated that IL-3 stimulation increased lyn kinase activity in immune precipitates (Torigoe, T., et al., *Blood* 80:617–624 (1992)). However, we have not detected an effect of IL-3 on lyn kinase activity or on the status of lyn tyrosine phosphorylation in the murine IL-3 dependent cells we have examined. We have also not detected any tyrosine phosphorylation or activation of kinase activity of Tec or c-fes. Therefore our efforts focused on developing reagents to assess the role of murine Jak1 and Jak2 genes in IL-3 signal transduction.

The Jak (Janus kinase; alternatively referred to as just another kinase) family of kinases was initially detected in PCR amplification of tyrosine kinase domains in hematopoietic cells (Wilks, A. F., *Proc. Natl. Acad. Sci. USA* 86:1603–1607 (1989)). These studies identified two closely related genes (FD17 and FD22; later termed Jak2 and Jak1) from which the major PCR amplification products were derived. The complete structure of the human Jak1 gene has been reported (Wilks, A. F., et al., *Mol. Cell. Biol.* 11:2057–2065 (1991)) and, recently, a partial sequence of the murine Jak2 gene was published (Harpur, A. G., et al., *Oncogene* 7:1347–1353 (1992)). Independently a third member of the family (Tyk2) was isolated by screening a cDNA library with a tyrosine kinase domain probe from the c-fms gene (Firmbach-Kraft, I., et al., *Oncogene* 5:1329–1336 (1990)). The family is characterized by the presence of two kinase domains, one of which is a carboxyl domain that has all the hallmarks of protein kinases. The second domain is immediately amino terminal and bears all the hallmarks of a protein kinase but differs significantly from both the protein tyrosine and serine/threonine kinases. Amino terminal to the kinase domains, there are no SH2 and SH3 domains that characterize most of the non-receptor tyrosine kinases. However, there is extensive similarity in this region among the Jak family members and a number of homology domains have been defined (Harpur, A. G., et al., *Oncogene* 7:1347–1353 (1992)).

A link between one member of the Jak family of kinases in signal transduction has been established in recent studies examining the cellular response to interferon alpha (IFNα) (Velazquez, L., et al., *Cell* 70:313–322 (1992)). Using a genetic approach, the Tyk2 gene was cloned by its ability to functionally reconstitute the cellular response to IFNα in a mutant human cell line that was unresponsive to IFNα. It has been speculated that the kinase activity of Tyk2 is activated following IFNα binding and is responsible for the phosphorylation of the 113 and 91/84 kDa proteins of the interferon-stimulated gene factor 3 α (ISGFα) complex (Fu, X. Y., *Cell* 70:323–335 (1992); Schindler, C., et al., *Science* 257:809–813 (1992)). Following phosphorylation this complex associates with the ISGF3γ, protein and the complex migrates to the nucleus and activates gene expression by binding to the interferon-stimulated response element.

A role for Jak2 in the response to erythropoietin (Epo) is described in Example 2. The studies described demonstrated that Epo stimulation induces tyrosine phosphorylation of Jak2 and activates its in vitro autophosphorylation activity. Using a series of mutants of EpoR, the induction of Jak2 tyrosine phosphorylation was found to correlate with the induction of biological responses. Jak2 was also shown to physically associate with the membrane proximal, cytoplasmic region of the Epo receptor that is required for biological activity.

In the studies presented here we disclose the complete structure of the murine Jak2 gene. We demonstrate that Jak2 is rapidly tyrosine phosphorylated in response to IL-3 and there is an associated activation of its in vitro autophosphorylation activity. The results provide evidence that Jak2 is the protein tyrosine kinase that couples IL-3 stimulation to tyrosine phosphorylation and ultimately to the biological responses. Moreover, the involvement of Jak2 in the responses to both IL-3 and Epo suggests that Jak2, or family members, are involved in the mitogenic signalling pathway of a variety of hematopoietic growth factor receptors.

Materials and Methods

Isolation of Murine Jak2 Clones. Polymerase chain reactions (PCR) with degenerative oligonucleotides corresponding to the conserved domain were used to amplify cDNAs from murine bone marrow derived monocytes as previously described (Wilks, A. F., *Proc. Natl. Acad. Sci. USA* 86:1603–1607 (1989)). The Jak2 cDNA clone was $^{32}$P labeled by random priming and used to screen murine monocyte and IL-3 dependent myeloid NFS58 and DA3 cell phage cDNA libraries (Yi and Willman, *Oncogene* 4:1081–1087 (1989); Morishita, K., et al., *Cell* 54:831–840 (1988); Bartholomew and Ihle, *Mol. Cell. Biol.* 11:1820–1828 (1991)). The isolated cDNA fragments were cloned into pBluescript vector and analyzed by restriction mapping and sequencing. Subsequent phage library screenings were done with the most 5' Jak2 cDNA fragments. The longest cDNAs were subcloned into pBluescript vector and the nucleotide sequence was determined by dideoxy chain termination method (Sanger, F., et al., *Proc. Natl. Acad. Sci. USA* 74:5463–5467 (1977)).

Northern Analysis. Total cellular RNA and poly(A)$^+$ RNA were isolated from mouse tissues and cell lines as previously described (Cleveland, J. L., et al., *Mol. Cell. Biol.* 9:5685–5695 (1989)). Approximately 20 µg of total RNA and 4 µg of poly(A)$^+$ RNA were separated on 1.0% agarose/formaldehyde gels and transferred to nitrocellulose filters. The filters were hybridized with $^{32}$P labeled randomly primed 800 bp cDNA fragment derived from the 5' of Jak2. After autoradiography the filters were stripped and probed with β-actin.

Cells and Cell Culture. The properties of the cell lines used in these studies have been described (Ihle and Askew, *Int. J. Cell. Cloning* 1:1–30 (1989)). The cells were maintained in RPMI supplemented with 10% fetal calf serum (FCS) and murine IL-3 (25 U/ml) for IL3 dependent cells. Mouse bone marrow derived monocytes were grown as previously described (Yi and Willman, *Oncogene* 4:1081–1087 (1989)).

Computer Analysis. The DNA and protein data bases were searched with the Genetics Computer Group sequence analysis software. The SwissProt and GenBank data bases were searched with FASTA and TFASTA programs.

Generation of Antibodies. Synthetic peptides corresponding to the N-terminal portion of Jak2 protein (amino acids 19–31) and to the hinge region between domains 1 and 2 (amino acids 758–776(SEQ ID No. 5)) were coupled to keyhole limpet hemocyanin by MES coupling and used for immunization of rabbits. A synthetic peptide to the analogous hinge region of Jak1 (amino acids 786–804 (SEQ ID No. 6)) was similarly prepared and used for competition studies. Unless otherwise indicated reference to Jak2 antibody or anti-peptide antibody, and manipulations involving Jak2 antibody, refer to antibody generated against the hinge region (amino acids 758–776 (SEQ ID No. 5)).

In vitro Translation and Transcription. Full length Jak1 or Jak2 cDNAs were inserted into pBSK (Stratagene) and used to make transcripts with T3 RNA polymerase according to the protocol provided. Approximately 3 µg of RNA was used in translation reactions (Stratagene) in the presence of $^{35}$S translabel (NEN). The products were divided equally and either run on SDS-PAGE without manipulation or immunoprecipitated with Jak1 or Jak2 antisera. Peptide competitions were preformed by incubating peptides (100 µg/ml) with antisera for 1 h at 4° C. prior to use in immunoprecipitations.

In vitro Kinase Assays. Immunoprecipitated proteins on Protein A-Sepharose (Pharmacia) were washed with kinase buffer (50 mM NaCl, 5 mM MgCl$_2$, 5 mM MnCl$_2$, 0.1 mM Na$_3$VO$_4$, 10 mM HEPES pH 7.4) and subsequently were incubated for 30 min at room temperature with an equal volume of kinase buffer containing 0.25 mCi/ml $^{32}$P-γ-ATP. After extensive washing, proteins were eluted with sample buffer for SDS-PAGE and separated on 7% gels. $^{32}$P-containing proteins were visualized by autoradiography. In vitro phosphorylated Jak2 was isolated from gel slices and the phosphoamino acid content determined by published procedures (Cooper, J. A., et al., *Methods Enzymol.* 99:387–402 (1983)).

Results

The spectrum of protein tyrosine kinases expressed in hematopoietic growth factor dependent cells was identified by reverse transcriptase/polymerase chain reactions (RT/PCR) using degenerative oligonucleotides corresponding to the conserved regions of the tyrosine kinase domain (Wilks, A. F., *Methods Enzymol.* 200:533–546 (1991)). One of the most frequently isolated cDNA clones was found to be identical to the clone FD17 (renamed Jak2) (Wilks, A. F., *Proc. Natl. Acad. Sci. USA* 86:1603–1607 (1989)).

Initial expression analysis indicated that Jak2 was abundantly and widely expressed in hematopoietic cells and prompted us to obtain full length cDNA clones for functional studies. Screening of murine myeloid cDNA libraries resulted in the isolation of several overlapping clones, the longest of which (4 kb) contained the entire coding region of Jak2.

The nucleotide sequence of Jak2 contains an open reading frame (ORF) of 3387 bp and the 5' end has three stop codons before the first ATG (FIG. 1). Although the first ATG does not fulfill the Kozak consensus flanking sequences, it is immediately followed by an ATG codon in the typical translation initiation environment (Kozak, M., *Nucl. Acids Res.* 15:8125-8148 (1987)). The 5' end does not contain an obvious signal peptide. The compiled size of the 3' untranslated region of the Jak2 clones is 0.9 kb which would correspond to a 4.4 kb transcript. One cDNA clone diverged at nucleotide 3271 and had a 1.4 kb 3' untranslated region. Transcripts for this cDNA would be 4.8 kb and may correspond to the larger transcript that is typically seen (see below).

The Jak2 ORF encodes a protein of 1129 amino acids with a calculated molecular weight of 130 kDa. Hydrophilicity analysis, using the Kyte and Doolittle algorithm, failed to identify transmembrane regions. During the course of these studies, a partial sequence of Jak2 was published (Harpur, A. G., et al., *Oncogene* 7:1347-1353 (1992)) which lacked the first 143 amino acids. A comparison of the sequences indicates 71 nucleotide differences in the coding region, resulting in 9 changes in amino acids (FIG. 1). The cDNA clones we have obtained did not contain the insert of 7 amino acids in position 711 that was found in one of four cDNA clones of the studies of Harpur et al. (*Oncogene* 7:1347-1353 (1992)).

The murine Jak2 gene is very closely related to other Jak family members including the human Tyk2 and Jak1 genes (42% and 43% identities respectively). We have also obtained full length cDNA clones for the murine Jak1 gene which has 45.5% identity to Jak2 at the nucleotide level in the coding region.

Like other members of the family, the murine Jak2 protein has a 600 amino acid long N-terminus that lacks obvious SH2 or SH3 domains. Following this is a kinase related domain (domain 2) and a carboxyl kinase domain (domain 1). The carboxyl kinase domain contains all the structural and functional motifs associated with protein tyrosine kinases including the conserved residues in subdomains VI-VIII that are characteristically associated with protein tyrosine kinases (Hanks, S. K., et al., *Science* 241:42-52 (1988)). The subdomain VIII, which is hypothesized to contribute to substrate recognition, shows a unique F-W-Y motif that is found in all Jak family members. Domain 2 begins at amino acid 543 and all of the 11 conserved structural subdomains of protein kinases can be identified. However, clear differences in the amino acid composition and spacing in critical kinase subdomains I, II, VI and VIII (Hanks, S. K., et al., *Science* 241:42-52 (1988)) raise the possibility that this domain may have a regulatory function or alternatively displays a presently unknown substrate specificity.

Although the N-terminus of the Jak family proteins is less homologous than the kinase domains (36-39% verses 49-56%), comparison of the N-terminal sequences of the Jak protein reveals several stretches of homology. Database searches with the N-terminal sequence of Jak2 did not show significant homology with other proteins but the presence of several highly conserved amino acid domains suggest that Jak proteins are functionally related. Close comparisons of the Jak homology domain 3 reveals some similarity to SH2 domains, but the functional significance of this sequence similarity remains to be determined.

The expression pattern of Jak2 was studied by Northern blot analysis in the following murine tissues: bone marrow, oviduct, ovary, testes, stomach, intestine, skeletal muscle, kidney, liver, thymus, spleen, brain, fetal brain, fetal liver, fetal intestine, and fetal lung. The expression pattern of Jak2 was also studied by Northern blot analysis in the following cell lines: fibroblasts (NIH 3T3); myeloid cells (32D.3, NFS-70, NFS-107, NFS-124, DA-3, DA-22, DA-29, DA31, DA-24, M 1), a mast cell line (AFSTh2), B-cells (DA-8, NFS- 112, plasmacytoma), T-cells (DA-2, EL-4, R-12) and a macrophage cell line (BAC1.2F5). Two transcripts of 4.4 and 4.8 kb were detected in all tissues and cell lines tested, but the level of expression and the relative abundance of the two transcripts varied. The smaller transcript was most abundant in skeletal muscle, spleen and oviduct and barely detectable in liver, kidney and intestine. The Jak2 expression level in adult liver was very low, whereas a more abundant message was detected in fetal liver. The Jak2 expression was detected in all 20 cell lines including 3T3 fibroblasts, B lymphoid, T lymphoid and a variety of myeloid cells representing different stages of differentiation and growth requirements.

In order to biochemically characterize Jak2 protein, anti-peptide antisera were prepared against a region (amino acids 758-776 (SEQ ID No. 5)) that was unique for Jak2 relative to the murine Jak1. To initially assess the reactivity of this antiserum, immunoprecipitations were done with in vitro synthesized Jak2.In vitro translation of Jak2 RNA gave an expected 130 kDa protein. This 130 kDa protein was immunoprecipitated by the Jak2 anti-peptide antiserum, but not by an irrelevant antiserum prepared against a peptide, the sequence of which is not found in Jak2. Immunoprecipitation was competed by the homologous peptide to which the Jak2 antiserum was raised, but not by an irrelevant peptide or by a peptide that is the homologous region of Jak1. The Jak2 anti-peptide antiserum did not immunoprecipitate in vitro synthesized Jak1. Lastly the Jak2 anti-peptide antiserum also immunoprecipitated a comparable 130 kDa protein from in vivo methionine labeled cells which was specifically competed by the homologous peptide. These results demonstrate that the Jak2 cDNA encodes a protein of 130 kDa and that the antipeptide antiserum specifically recognizes the Jak2 protein.

IL-3 stimulation of growth factor dependent cells rapidly induces tyrosine phosphorylation of several cellular substrates including the $\beta$ subunit of the IL-3 receptor (Ihle, J. N., in *Interleukins: Molecular Biology and Immunology*, Kishimoto, T., ed., Karger, Basel, pp. 65-106 (1992); Sorensen, P., et al., *J. Biol. Chem.* 264:19253-19258 (1989) ). We therefore examined the possibility that Jak2 might be a substrate of tyrosine phosphorylation.

Western blotting of total cell lysates with a monoclonal antibody against phosphotyrosine (4G10) detected the appearance of several proteins following IL-3 stimulation, including a broad band at 130-140 kDa, a minor band at 70 kDa and major bands at 55 kDa, 50 kDa and 38 kDa. When cell extracts were immunoprecipitated with the Jak2 anti-peptide antiserum, a 130 kDa protein was readily detected in stimulated cells but not in unstimulated cells. Also of note is the presence of induced proteins of 110 kDa, 70 kDa and 60 kDa that coimmunoprecipitated with Jak2.These substrates have been consistently seen in immunoprecipitations of Jak2. Immunoprecipitation with an antiserum against the murine Jak1 consistently detected a weak band at 130 kDa indicating that Jak1 may also be a substrate. Inducible tyrosine phosphorylation of the IL-3 $\beta$ chain was observed in extracts immunoprecipitated with $\alpha$IL3R$\beta$ antiserum as a diffuse band with a slightly reduced mobility relative to Jak2 in IL-3 stimulated cells. Thus the broad band seen in total cell lysates consists of both Jak2 and the IL-3 $\beta$ chain.

To further establish that IL-3 induces Jak2 tyrosine phosphorylation, the kinetics of the response and the ability to detect induction with a second monoclonal antibody against phosphotyrosine were examined. When cells were stimulated with IL-3 and the phosphotyrosine containing fraction was isolated by binding to and elution from sepharose beads containing the 1G2 antiphosphotyrosine monoclonal antibody, Jak2 was readily detected in Western blots using the Jak2 anti-peptide antiserum. A comparable 130 kDa band was not detected in unstimulated cells.

Jak2 tyrosine phosphorylation was readily apparent following 5 min of IL-3 stimulation and subsequently decreased in a manner comparable to the general pattern of tyrosine phosphorylation seen following IL-3 stimulation (Isfort, R., et al., J. Biol. Chem. 263:19203–19209 (1988)). During this period (from 0–120 minutes after IL-3 stimulation) there was no change in the levels of Jak2 as assessed by Western blotting with the Jak2 anti-peptide antiserum.

To determine whether IL-3 binding affected Jak2 kinase activity, cells were stimulated with IL-3 for 10 min, Jak2 was immunoprecipitated and in vitro kinase assays were performed. The results are shown in FIG. 4. When extracts were immunoprecipitated with normal rabbit serum, no in vitro kinase activity was detected with extracts from unstimulated or stimulated cells. However, when extracts were immunoprecipitated with Jak2 anti-peptide antiserum, a 130 kDa was readily detected with extracts from IL-3 stimulated cells that co-migrated with the immunoprecipitated Jak2. By contrast, the 130 kDa band was not detected when extracts of unstimulated cells were used. Phosphoamino acid analysis of the 130 kDa band demonstrated the presence of predominantly phosphotyrosine.

Interestingly, there were no other major protein bands phosphorylated in these in vitro reactions, including the heavy chain of IgG (FIG. 3). As discussed below this may reflect the substrate specificity of Jak2 kinase. The specificity for Jak2 is indicated by the ability of the corresponding peptide to block precipitation of kinase activity while a peptide to the corresponding region of Jak1 had no effect. Together the data demonstrate that IL-3 stimulation results in the tyrosine phosphorylation of Jak2 and activation of its autophosphorylation activity.

Discussion

Our studies provide the first complete sequence of the murine Jak2 gene. Three lines of evidence indicate that the cDNA clones we have obtained contain the entire coding region. First, comparison of the murine Jak2 5' sequence with the published sequences of human Tyk2 and Jak1 show that all proteins start at the same site. Second, the first ATG is preceded by stop codons in all reading frames. Lastly, the sizes of the compiled cDNA sizes are consistent with the 4.4 and 4.8 kb sized transcripts.

The sequence of our murine Jak2 cDNAs varies from the published partial sequence of the gene (Harpur, A. G., et al., Oncogene 7:1347–1353 (1992)) and includes nine amino acid changes, seven of which are conservative substitutions. Our cDNA clones lacked an insert of 7 amino acids found in one of four Jak2 cDNA clones in the published sequence. A similar putative additional exon was also observed in the human Tyk2 cDNA (Velazquez, L., et al., Cell 70:313–322 (1992)).

IL-3 stimulation of hematopoietic growth factor dependent cells has been shown to rapidly induce tyrosine phosphorylation of a number of cellular substrates (Ihle, J. N., in *Interleukins: Molecular Biology and Immunology*, Kishimoto, T., ed., Karger, Basel, pp. 65–106 (1992); Ihle, J. N., in *Peptide Growth Factors and Their Receptors*, Sporn and Roberts, eds., Springer Verlag, New York (1990)). Our results demonstrate that one of these substrates is Jak2 (Ihle, J. N., in *Interleukins: Molecular Biology and Immunology*, Kishimoto, T., ed., Karger, Basel, pp. 65–106 (1992)). Among the protein tyrosine kinases that are expressed in IL-3 dependent cells and which we could examine, there was a remarkable specificity for Jak2.

In particular, we have not detected any changes in the tyrosine phosphorylation of lyn, tec or c-fes. However we have consistently seen a low level of tyrosine phosphorylation of Jak1 following IL-3 stimulation. This is not due to cross-reactivity of the antisera used and, since both Jak1 and Jak2 are expressed at comparable levels in the cells, is not due to differences in protein levels. Therefore, it is likely that Jak1 shares sufficient similarity to Jak2 to weakly associate with the IL-3 receptor complex. Alternatively, since there is considerable sequence homology between Jak1 and Jak2 at the potential autophosphorylation site, Jak1 may be a substrate for Jak2. To date, we have not detected an effect of IL-3 stimulation on Jak1 in vitro kinase activity.

IL-3 stimulation results in both the induction of tyrosine phosphorylation of Jak2 and activation of Jak2 in vitro kinase activity. The carboxyl protein tyrosine kinase domain of Jak2 contains the characteristic autophosphorylation site that is associated with the activation kinase activity of a number of kinases (Hanks, S. K., et al., Science 241:42–52 (1988)). The in vivo tyrosine phosphorylation is expected to occur at this site based on the concomitant appearance of tyrosine phosphorylation and detectable in vitro kinase activity.

The requirement for IL-3 binding for detection of kinase activity indicates that Jak2 kinase activity is highly regulated in cells, consistent with a major role in growth regulation. The primary substrate of the in vitro kinase reactions was Jak2. In particular, there was no detectable phosphorylation of immunoglobulins nor is enolase a substrate for Jak2, indicating that Jak2 may have a strict substrate specificity. The requirement for receptor activation and the substrate specificity may account for the inability to demonstrate Jak1 protein tyrosine kinase activity under a variety of conditions in previous studies (Wilks, A. F., et al., Mol. Cell. Biol. 11:2057–2065 (1991)).

Jak2 is also tyrosine phosphorylated and activated following Epo stimulation (see Example 2). Moreover, these studies demonstrated that Jak2 physically associates with a membrane proximal region of the cytoplasmic domain of the Epo receptor (EpoR) that is essential for function. Whether Jak2 physically associates with one or both subunits of the IL-3 receptor is currently being examined. However, like EpoR, the β subunit of the IL-3 receptor is rapidly tyrosine phosphorylated and it can be hypothesized that this phosphorylation is mediated by Jak2.

In the case of EpoR, tyrosine phosphorylation occurs at sites in the cytoplasmic, carboxyl end and this region is not required for mitogenesis. Whether the tyrosine phosphorylation of the IL-3 β subunit contributes to the biological response is not known.

The ability of both IL-3 and Epo to induce the tyrosine phosphorylation and activation of Jak2 suggests the possibility that Jak2 may be a component in the signal transducing pathways of several cytokine receptors. We have also found that GM-CSF and G-CSF induce the tyrosine phosphorylation of Jak2. This is consistent with several studies that have shown that these hematopoietic growth factors induce comparable patterns of tyrosine phosphorylation (Ihle, J. N., in *Interleukins: Molecular Biology and*

*Immunology*, Kishimoto, T., ed., Karger, Basel, pp. 65–106 (1992)). We have also observed tyrosine phosphorylation of Jak2 in response to IFNγ in a macrophage cell line.

The hematopoietic growth factor receptors are members of a receptor superfamily that also includes the receptors for growth hormone, the prolactin receptor, cilliary neurotropic factor and others (Bazan, J. F., *Science* 257:410–413 (1992) ). Moreover, the receptors for interferon, although more distantly related, have been speculated to have evolved from a common progenitor. Recent studies (Velazquez, L., et al., *Cell* 70:313–322 (1992)) have shown that Tyk2 is involved in IFNα signalling. Our studies have shown that Jak2 are involved in the signalling pathways of IL-3 and Epo (see Example 2) as well as G-CSF, GM-CSF and IFNγ. In addition, recent studies have implicated Jak2 in the response to growth hormone. Therefore Jak family kinases are involved in the signal transducing pathways utilized by several members of the cytokine/interferon superfamily of receptors. Moreover, the Jak family of kinases may also regulate gene expression through comparable pathways involving family members related to the ISGF3α proteins (Schindler, C., et al., *Proc. Natl. Acad. Sci. USA* 89:7836–7839 (1992); Fu, X-Y., et al., *Proc. Natl. Acad. Sci. USA* 89:7840–7843 (1992)) and the ISGF3γ related DNA binding proteins including ICSBP, IRF1, IRF2 and possibly myb (Veals, S. A., et al., *Mol. Cell. Biol.* 12:3315–3324 (1992)).

Example 2

Jak2 Associates with the Erythropoietin Receptor and Is Tyrosine Phosphorylated and Activated Following Stimulation With Erythropoietin Summary Erythropoietin (Epo) regulates the proliferation and terminal differentiation of erythroid lineage cells through its interaction with its receptor (EpoR). EpoR is a member of the cytokine receptor family and contains a cytoplasmic domain that lacks an identifiable kinase catalytic domain. Binding of Epo, however, rapidly induces tyrosine phosphorylation of EpoR as well as a number of cellular proteins. The ability to induce tyrosine phosphorylation is tightly correlated with the ability of the receptor to induce transcription of immediate early genes and to be mitogenic. These biological responses have been shown to require a membrane proximal region of the receptor cytoplasmic domain. Here we demonstrate that one of the substrates of protein tyrosine phosphorylation is the 130 kDa Jak2, a protein tyrosine kinase. Moreover, Epo stimulation activates Jak2 in vitro autophosphorylation activity. Using a series of mutants of EpoR, the induction of Jak2 tyrosine phosphorylation and autophosphorylation activity were found to correlate with the induction of biological responses. Furthermore, we show that Jak2 physically associates with the membrane proximal region of the EpoR cytoplasmic domain that is required for biological activity. Together the results indicate that Jak2 is the kinase that couples Epo binding to tyrosine phosphorylation and ultimately the biological responses that are required for erythropoiesis.

Introduction

Hematopoiesis is regulated through the interaction of a variety of hematopoietic growth factors with their cognate receptors (Clark and Kamen, *Science* 236:1229–1237 (1987); Metcalf, D., *Nature* 339:27–30 (1989)). The majority of hematopoietic growth factor receptors belong to a common cytokine receptor family that is characterized by the presence of four positionally conserved cysteines and a WSXWS (SEQ ID No. 1) motif in the extracellular domain. The family is also characterized by variably sized cytoplasmic domains that show very limited sequence similarity and which do not contain identifiable motifs that might indicate the signal transducing mechanisms. Erythropoietin (Epo) is the hematopoietic growth factor which uniquely supports the proliferation and terminal differentiation of cells committed to the erythroid lineage (Krantz, S. B., *Blood* 77:419–434 (1991)). The Epo receptor (EpoR) was cloned by expression cloning (D'Andrea et al., *Cell* 57:277–285 (1989)) and the sequence of the cDNA predicts a protein of 507 amino acids with a single membrane-spanning domain and the motifs associated with the cytokine receptor superfamily. Unlike several of the hematopoietic growth factor receptors, a single gene product has been shown to be sufficient for Epo binding and function (D'Andrea et al., *Cell* 57:277–285 (1989)).

Introduction of the EpoR into IL-3 dependent cell lines confers on the cells the ability to proliferate in response to Epo and this has provided an important model to study receptor signal transduction (D'Andrea et al., *Cell* 57:277–285 (1989); Miura et al., *Mol. Cell Biol.* 11:4895–4902 (1991)). In transfected cells, Epo induces the expression of a series of immediate early genes including c-myc, c-fos, c-pim-1 and egr-1 (Miura et al., *Mol. Cell. Biol.* 13:1788–1795 (1993)). In addition, Epo induces the rapid tyrosine phosphorylation of a series of cellular substrates (Linnekin et al., *Proc. Natl. Acad. Sci.* 89:6237–6241 (1992); Dusanter-Fourt et al., *J. Biol. Chem.* 267:10670–10675 (1992); Quelle and Wojchowski, *J. Biol. Chem.* 266:609–614 (1991); Miura et al., *Mol. Cell Biol.* 11:4895–4902 (1991); Yoshimura and Lodish, *Mol. Cell. Biol.* 12:706–715 (1992); Damen et al., *Blood* 80:1923–1932 (1992)), suggesting that EpoR may function by coupling ligand binding to the activation of a protein tyrosine kinase. One of the substrates of Epo induced tyrosine phosphorylation is the receptor (Dusanter-Fourt et al., *J. Biol. Chem.* 267:10670–10675 (1992); Yoshimura and Lodish, *Mol. Cell. Biol.* 12:706–715 (1992); Miura et al., *Mol. Cell Biol.* 11:4895–4902 (1991)).

The cytoplasmic domain of EpoR consists of 236 amino acids and contains some amino acid sequence similarity to the cytoplasmic domain of the IL-2 receptor β chain (D'Andrea et al., *Cell* 58:1023–1024 (1989)). EpoR also contains a region that has similarity to the cytokine receptor conserved domains, termed box 1 and 2, which were initially defined in the IL-6 signal transducing gp130 protein (Murakami et al., *Proc. Natl. Acad. Sci. USA* 88:11349–11353 (1991)). The membrane proximal region of the cytoplasmic domain has been shown to be essential for the biological activities of the receptor. Carboxyl truncation of 108 amino acids has no effect on the ability of the receptor to induce immediate early genes, induce tyrosine phosphorylation or cause milogenesis (Miura et al., *Mol. Cell. Biol.* 13:1788–1795 (1993); Miura et al., *Mol. Cell Biol.* 11:4895–4902 (1991)). In some cells lines, carboxyl truncations have increased the mitogenic response (D'Andrea et al., *Mol. Cell Biol.* 11:1980–1987 (1991a)), suggesting that the membrane distal region negatively affects the response to Epo.

Within the membrane proximal region, carboxyl truncations or deletions of the box 1 and box 2 domains can inactivate the receptor for all biological activities (Miura et al., *Mol. Cell. Biol.* 13:1788–1795 (1993); Miura et al., *Mol. Cell Biol.* 11:4895–4902 (1991)). The importance of this region was further demonstrated by the inactivation of receptor functions by mutation of a conserved Trp residue between box 1 and box 2.Together the results demonstrate that the membrane proximal region of EpoR is essential for all the biological responses that have been examined, including the induction of tyrosine phosphorylation.

Although the importance of EpoR to couple to protein tyrosine phosphorylation for biological activities has been clearly demonstrated, very little has been known concerning the kinases that might be involved. The rapid induction of tyrosine phosphorylation of the carboxyl region of EpoR (Miura et al., *Mol. Cell Biol.* 11:4895–4902 (1991); Yoshimura and Lodish, *Mol. Cell. Biol.* 12:706–715 (1992); Dusanter-Fourt et al., *J. Biol. Chem.* 267:10670–10675 (1992)) suggests that the receptor is closely associated with a kinase either constitutively or following ligand binding. One study (Yoshimura and Lodish, *Mol. Cell. Biol.* 12:706–715 (1992)) identified a non-glycosylated protein of 130 kDa that could be cross-linked with the receptor and which was tyrosine phosphorylated either in vivo or in in vitro kinase assays as assessed by its ability to be detected by an antiphosphotyrosine antibody. Whether the 130 kDa was a kinase could not be determined. Recent studies (Linnekin et al., *Proc. Natl. Acad. Sci. USA* 89:6237–6241 (1992)) also identified a 97 kDa substrate of tyrosine phosphorylation which could be radiolabeled with an azido derivative of ATP, suggesting that it was a kinase. Whether the 130 kDa or 97 kDa potential kinases are previously characterized kinases was not determined.

To detect potentially novel protein tyrosine kinases that might be involved in Epo signal transduction, we have utilized PCR amplification approaches comparable to those described by Wilks, A. F., *Proc. Natl. Acad. Sci. USA* 86:1603–1607 (1989). Similar to the studies of Wilks et al. (Wilks, A. F., *Proc. Natl. Acad. Sci. USA* 86:1603–1607 (1989); Wilks et al., *Mol. Cell. Biol.* 11:2057–2065 (1991)) as well as others (Partanen et al., *Proc. Natl. Acad. Sci. USA* 87:8913–8917 (1990)), two of the products encode two closely related genes (Jak1 and Jak2) which constitute a relatively new kinase subfamily termed the Janus kinases (alternatively referred to as just another kinase family) that also includes the Tyk2 gene (Firmbach-Kraft et al., *Oncogene* 5:1329–1336 (1990)). The Tyk2 gene product has recently been implicated in signal transduction through the interferon a (INFα) receptor (Velazquez et al., *Cell* 70:313–322 (1992)).

To explore the potential role of Jak1 and Jak2 genes in hematopoietic signal transduction we have isolated full-length cDNA clones for the murine genes and prepared antisera against the proteins (see Example 1). We report here that Epo stimulation rapidly induces the specific tyrosine phosphorylation of Jak2 and activates its in vitro kinase activity. The induction of tyrosine phosphorylation and activation of kinase activity is dependent upon a membrane proximal region of the EpoR cytoplasmic domain that is essential for mitogenesis. Finally, we demonstrate that Jak2 physically associates with the EpoR and this association requires the membrane proximal region. Together the data demonstrate that Jak2 is involved in EpoR signal transduction.

Results
Jak2 is Specifically and Rapidly Tyrosine Phosphorylated Following Epo Stimulation Epo rapidly induces the tyrosine phosphorylation of a number of cellular substrates, including the receptor for Epo, suggesting that the receptor associates with a cytoplasmic tyrosine kinase(s) (Yoshimura et al., *Nature* 348:647–649 (1990); Damen et al., *Blood* 80:1923–1932 (1992); Quelle and Wojchowski, *J. Biol. Chem.* 266:609–614 (1991); Quelle et al., *J. Biol. Chem.* 267:17055–17060 (1992); Miura et al., *Mol. Cell Biol.* 11:4895–4902 (1991); Linnekin et al., *Proc. Natl. Acad. Sci. USA* 89:6237–6241 (1992); Dusanter-Fourt et al., *J. Biol. Chem.* 267:10670–10675 (1992)). To identify the kinases that might be involved, we and others (Wilks, A. F., *Proc. Natl. Acad. Sci. USA* 86:1603–1607 (1989); Wilks et al., *Mol. Cell. Biol.* 11:2057–2065 (1991); Partanen et al., *Proc. Natl. Acad. Sci. USA* 87:8913–8917 (1990); see Example 1) have used PCR approaches to detect known and potentially novel kinases that are present in hematopoietic growth factor dependent cell lines. These studies, coupled with Northern blot analysis, identified transcripts for lyn, c-fes, tec, Jak1 and Jak2 in DA3 myeloid cells (Mano et al., *Oncogene* 8:417–424 (1993)).

To initially determine whether any of these kinases might be involved in Epo signal transduction we examined their ability to be inducibly tyrosine phosphorylated as follows. DA3(EpoR) cells were removed from growth factors for approximately 14 hr. The cells were either not stimulated (−) or stimulated (+) with 30 U/ml of human Epo for 10 minutes. The cells were subsequently collected by centrifugation and cell extracts prepared as described in Experimental Procedures below. Aliquots of extracts ($2 \times 10^7$ cells) from unstimulated and stimulated cells were immunoprecipitated with antisera against Jak2, Jak1, c-fes, lyn or tec. The immunoprecipitates were resolved by SDS-PAGE, transformed to nitrocellulose filters and the filters were probed with the 4G10 anti-phosphotyrosine monoclonal antibody as described in Experimental Procedures. To assess the levels of each of the immunoprecipitated tyrosine kinases, comparable blots were probed with antisera against the individual kinases as described in Experimental Procedures below.

In experiment described above, Epo stimulation resulted in the appearance of a p130 kDa band that was immunoprecipitated by an antiserum against Jak2. This band was not observed when the immunoprecipitation was done in the presence of the peptide to which the antiserum was raised. Comparable results were also obtained when the blots were probed with a different monoclonal antibody against phosphotyrosine (PY20). In contrast, there was no apparent induction of tyrosine phosphorylation of lyn, fes or tec under comparable conditions.

A weak 130 kDa band was seen with antiserum against Jak1 in several experiments conducted as described above. This was not due to the cross-reactivity of the antisera. Both antisera were prepared against peptides with minimal sequence identity between Jak1 and Jak2 and only immunoprecipitate the appropriate kinase from in vitro translation reactions (see Example 1). Together the results suggest that the Jak kinases are inducibly tyrosine phosphorylated in response to Epo but that Jak2 is preferentially phosphorylated.

To further establish that Epo stimulation induces tyrosine phosphorylation of Jak2, we examined the ability of the monoclonal antibody 1G2 to detect changes in phosphorylation. Cells were treated as above, lysed and the phosphotyrosine containing fraction of proteins was isolated by binding to and elution from 1G2 monoclonal antibody sepharose beads as previously described (Frackelton et al., *Mol. Cell Biol.* 3:1343–1352 (1983); Isfort et al., *J. Biol. Chem.* 263:19203–19209 (1988)). The eluted proteins were resolved by SDS-PAGE, blotted to filters and the filters were probed with an antiserum against Jak2. The results were as follows. Epo induced the appearance of a p130 kDa band that was readily detectable with the antiserum against Jak2 in the 1G2 eluates. Western blotting of total cell lysates indicated comparable levels of the p130 kDa Jak2 in both stimulated and unstimulated cells. Probing of blots with antisera against lyn, tec or c-fes failed to detect these kinases.

To determine the kinetics of appearance of tyrosine phosphorylated Jak2, extracts from DA3(EpoR) cells were prepared at 0, 5, 10, 30 and 60 minutes following Epo treatment, immunoprecipitated with antisera against Jak2 and the immunoprecipitates were resolved by SDS-PAGE. The proteins were transferred to nitrocellulose and Western blotted with the 4G10 monoclonal antibody. Under these conditions the induction of a 130 kDa band was readily evident. Stimulation was maximal at 5 min and subsequently declined and was not evident at 1 hour.

Together the above results indicated that Epo stimulation results in the rapid and specific tyrosine phosphorylation of Jak2, relative to other protein tyrosine kinases, in growth factor dependent cells.

Epo Stimulation Activates Jak2 In Vitro Kinase Activity

Tyrosine phosphorylation of protein tyrosine kinases is commonly associated with the activation of kinase activity (Hanks et al., Science 241:42–52 (1988)). We therefore examined the in vitro Jak2 kinase activity in immunoprecipitates. In these experiments cells were stimulated with Epo for 10 minutes, then cell extracts were prepared and immunoprecipitated with either normal rabbit serum (NRS) or antiserum specific for Jak2, in vitro kinase assays were performed and the phosphorylated proteins resolved by SDS-PAGE. Immunoprecipitates of extracts with normal rabbit serum, from unstimulated or Epo stimulated cells, had no detectable in vitro kinase activity. In contrast, immunoprecipitates of extracts with Jak2 antiserum from Epo stimulated cells had readily detectable kinase activity. The major product of phosphorylation was a 130 kDa protein that co-migrated with Jak2. A comparable activity was not detected in extracts from unstimulated cells. The specificity for Jak2 was indicated by the ability of the peptide to which the Jak2 antiserum was raised to block immunoprecipitation of kinase activity while a peptide to the comparable region of Jak1 had no effect. The primary phosphoamino acid in the in vitro kinase assays detected by 2 dimensional thin layer electrophoresis was determined to be tyrosine.

Tyrosine Phosphorylation of Jak2 and Activation of In Vitro Kinase Activity Correlates with Mitogenesis Our previous studies (Miura et al., Mol. Cell Biol. 11:4895–4902 (1991); Miura et al., Mol. Cell. Biol. 13:1788–1795 (1993)) defined a membrane proximal region of the cytoplasmic domain of EpoR that is essential for induction of tyrosine phosphorylation, induction of the expression of several immediate early genes and for mitogenesis. It was therefore important to determine whether the induction of Jak2 phosphorylation required a comparable domain and whether Jak2 phosphorylation could be correlated with these biological responses. We therefore examined Epo-induced tyrosine phosphorylation mediated by a series of mutated receptors. The H mutant of EpoR lacks the carboxyl terminal 108 amino acids but retains complete biological activity (Miura et al., Mol. Cell. Biol. 13:1788–1795 (1993)).

Epo stimulation of cells expressing the H mutant resulted in the tyrosine phosphorylation of a 130 kDa band. It should also be noted that the observed Jak2 tyrosine phosphorylation with cells expressing the H mutant was stronger than with cells expressing the wild-type receptor. This could be due to somewhat higher levels of Jak2, as indicated in the lower panel, or could be due to the removal of a negatively acting domain in the carboxyl region of the receptor (D'Andrea et al., Mol. Cell Biol. 11:1980–1987 (1991)). Also of note in these experiments is the presence of an inducible 72 kDa phosphoprotein that is detected in the Jak2 immunoprecipitates from extracts of cells expressing the wild-type receptor. This is the size expected for EpoR and the possibility that it is EpoR is further supported by the absence of a comparable band in the experiments with the H mutant in which the carboxyl truncation removes the sites of tyrosine phosphorylation (Miura et al., Mol. Cell Biol. 11:4895–4902 (1991)). This observation suggested that EpoR may physically associate with Jak2.

Carboxyl deletions that extend further than the H mutant, such as is present in the S mutant which lacks the carboxyl 146 amino acids of the receptor, inactivate the receptor for induction of tyrosine phosphorylation, induction of the immediate early genes and mitogenesis in DA-3 cells (Miura et al., Mol. Cell Biol. 11:4895–4902 (1991)). No induction of Jak2 tyrosine phosphorylation was evident following Epo stimulation of cells expressing this mutant.

We also previously demonstrated that the deletion of 20 amino acids (PB mutant) in the membrane proximal region of the cytoplasmic domain inactivates the receptor for all biological activities. No tyrosine phosphorylation of Jak2 was detected in Epo treated cells expressing this mutant.

Lastly we examined a point mutant, PM4, which contains the inactivating mutation $W^{282}$->R of the conserved W residue between the box 1 and box 2 regions (Miura et al., Mol. Cell. Biol. 13:1788–1795 (1993)). No tyrosine phosphorylation of Jak2 was seen in cells expressing this mutant.

We next examined the correlation between induction of Jak2 tyrosine phosphorylation and mitogenesis with the ability to activate in vitro Jak2 kinase activity. Clones of cells expressing the various mutant receptors were either not stimulated or stimulated with Epo for 10 min. The cells were lysed and Jak2 was immunoprecipitated and the precipitates used in in vitro kinase assays as above. Phosphorylations were assessed by resolving the immunoprecipitates by SDS-PAGE and autoradiography.

As in the previously described results, the major product of phosphorylation detected in the reactions was a 130 kDa phosphoprotein that migrates at the position of Jak2. Phosphorylation of Jak2 was evident in cells stimulated with Epo that expressed the mitogenically active H mutant. No kinase activity was detected in immunoprecipitates of Epo stimulated cells-expressing the mitogenically inactive S truncation mutation, the PB deletion mutant or the PM4 point mutant. These results demonstrate that the membrane proximal region, which is essential for biological activity, is also required for induction of Jak2 tyrosine phosphorylation and for activation of its kinase activity.

Induction of Jak Tyrosine Phosphorylation in 3T3 Cells Expressing EpoR

Jak2 is expressed in a wide variety of cell lineages (see Example 1); Harpur et al., Oncogene 7:1347–1353 (1992)). We therefore determined whether Jak2 might couple with EpoR and be inducibly tyrosine phosphorylated in a non-hematopoietic lineage. For this, we examined the response of 3T3 fibroblasts that had been transfected with EpoR expression constructs and express high affinity receptors for Epo.

To initially determine whether Epo stimulation is coupled to tyrosine phosphorylation in fibroblasts expressing the receptor, the ability of Epo to induce tyrosine phosphorylation of cellular proteins as well as the receptor was examined. When blots of extracts from 3T3(EpoR) cells were probed with a antiphosphotyrosine monoclonal antibody, a variety of bands were detected and no detectable differences were seen in cells treated with Epo. However, when the extracts were first immunoprecipitated with an antiserum against EpoR and the blots were probed for phosphotyrosine containing proteins, a 72 kDa protein was detected in Epo stimulated cells, consistent with the induction of tyrosine phosphorylation of EpoR.

When cell extracts were first immunoprecipitated with antiserum against Jak2 and then Western blotted for phosphotyrosine containing proteins or Jak2, the results obtained were as follows. Immunoprecipitates from unstimulated and Epo stimulated fibroblasts contained comparable levels of Jak2 as assessed by probing the blots with an antiserum against Jak2. Following stimulation of the cells with Epo, a 130 kDa band, co-migrating with Jak2, was readily detected by a monoclonal antibody against phosphotyrosine (4G10). A comparable band was not detected in control fibroblasts that did not contain EpoR. These data demonstrate that EpoR can functionally couple with Jak2 in fibroblasts and mediate Epo induced tyrosine phosphorylation of Jak2.

Jak2 Associates with Mitogenically Active Receptors for Erythropoietin

The rapid induction of tyrosine phosphorylation of EpoR and Jak2 suggested the possibility that Jak2 physically associates with EpoR. This possibility was particularly intriguing since previous studies (Yoshimura and Lodish, *Mol. Cell. Biol.* 12:706–715 (1992)) identified a 130 kDa protein which could be cross-linked to EpoR and which could be phosphorylated in vitro. The possibility of an association of Jak2 and EpoR was also indicated in several experiments in which a phosphotyrosine containing 72 kDa protein co-immunoprecipitated with Jak2.

To directly examine the ability of Jak2 to physically associate with Epo, a series of GST (glutathione-S-transferase)-fusion proteins containing the cytoplasmic domains of wild type and mutant EpoRs were constructed and expressed in bacteria. The fusion proteins were purified by affinity binding to glutathione-sepharose beads and the proteins, on affinity beads, were incubated with extracts of unstimulated or Epo stimulated DA3(EpoR) cells. The bound proteins were recovered from the beads, resolved on SDS-PAGE and the gels blotted to nitrocellulose. The blots were subsequently probed with antisera against various tyrosine kinases.

A 130 kDa protein was readily detectable when extracts from either unstimulated or stimulated cells were used and the blots were probed with an antiserum against Jak2. The 130 kDa protein was not detected when the antiserum was incubated with an excess of the peptide to which it was raised. A 130 kDa protein was also detected with an antiserum against Jak1, although at much lower levels than that seen with antiserum against Jak2. Bands were not detected that would be consistent with the presence of lyn, c-fes or tec when the blots were probed with the respective antisera. These results demonstrated that among the tyrosine kinases examined, Jak2 associated with the GST fusion protein containing the cytoplasmic domain of EpoR.

If the physical association of Jak2 and EpoR detected above was biologically relevant it might be predicted that mutations which affect the receptor's mitogenic activity would alter binding and, conversely, truncations of the receptor that do not affect biological activity would not affect binding. To explore this possibility, fusion proteins were constructed that contained the cytoplasmic portion of the truncated, but mitogenically active, H mutant as well as the mitogenically inactive PB and PM4 mutants. When cell extracts were incubated with GST alone bound to glutathione-sepharose and the blots were probed with an antiserum against Jak2, a 130 kDa protein was not detected. In contrast, when fusion proteins containing either the complete cytoplasmic domain or the carboxyl-truncated cytoplasmic domain of the H mutant were used, a 130 kDa protein was readily detectable. The 130 kDa protein was not detected when extracts were incubated with a fusion protein containing the PB mutant deletion. However, the 130 kDa protein was detected when a fusion protein containing the mitogenically inactive PM4 mutation was used. This may be due to the differences in the assays to detect functional verses physical interactions as discussed below. These results suggest that the membrane proximal domain that is required for mitogenesis also mediates the association of EpoR and Jak2.

Discussion

These studies are the first to identify a protein tyrosine kinase that associates with EpoR and which is tyrosine phosphorylated and activated in response to ligand binding. Previous studies have demonstrated that Epo binding rapidly induces tyrosine phosphorylation of cellular substrates, as well as EpoR, and that this ability is tightly coupled to the induction of mitogenesis (Miura et al., *Mol. Cell Biol.* 11:4895–4902 (1991); Miura et al., *Mol. Cell. Biol.* 13:1788–1795 (1993)). Therefore there has been considerable interest in identifying the kinase (or kinases) that couples Epo binding to the biological responses. Using PCR approaches (Wilks, A. F., *Proc. Natl. Acad. Sci. USA* 86:1603–1607 (1989); Wilks, A. F., *Meth. Enzymol.* 200:533–546 (1991); Partanen et al., *Proc. Natl. Acad. Sci. USA* 87:8913–8917 (1990); Mano et al., *Oncogene* 8:417–424 (1993)), attempts have been made to define the spectrum of protein tyrosine kinases that are present in myeloid cells and which might contribute to signal transduction.

Among the kinases expressed in IL-3/Epo dependent cells, there has been an interest in lyn, a member of the src gene family kinase, in signal transduction. This was based on the demonstration that IL-2 stimulation of T cells causes an increase in the kinase activity of the highly related lck kinase (Horak et al., *Proc. Natl. Acad. Sci. USA* 88:1996–2000 (1991)) and the demonstration of a physical association of lck with the cytoplasmic domain of the IL-2 receptor β chain (Hatakeyama et al., *Science* 252:1523–1528 (1991)). It should be noted however, that lck associates with a region of the IL-2 receptor β chain which is not required for mitogenesis (Hatakeyama et al., *Cell* 59:837–845 (1989); Hatakeyama et al., *Science* 252:1523–1528 (1991)). A role for lyn in IL-3 signal transduction was indicated by a report showing that IL-3 stimulation induces an increase in lyn kinase activity (Torigoe et al., *Blood* 80:617–624 (1992)). However, we have been unable to see a consistent effect of either IL-3 or Epo on lyn kinase activity in the hematopoietic growth factor dependent cells we have examined. As illustrated here, we have also been unable to detect any effect of Epo binding on the state of tyrosine phosphorylation of lyn nor have we been able to demonstrate association of lyn with EpoR.

We have also been unable to detect any changes in tec tyrosine phosphorylation, activation of kinase activity (data not shown) or association with EpoR. Tec is expressed in myeloid cells (Mano et al., *Oncogene* 8:417–424 (1993)) and its potential importance has been suggested by the identification of highly related kinases in T-cells, itk (IL-2 inducible T cell kinase) and in B-cells BPK/atk (B-cell progenitor kinase, agammaglobulinemia tyrosine kinase) (Silicano et al., *Proc. Natl. Acad. Sci. USA* 89:11194–11198 (1992); Tsukada et al., *Cell* (in press, 1993); Vetrie et al.,

*Nature* 361:226–233 (1993)). The BPK/atk gene is tightly linked to X-linked agammaglobulinemia (XLA) and kinase activity is reduced or absent in XLA pre-B and B-cell lines (Tsukada et al., *Cell* (in press, 1993)). Moreover, genetically acquired mutations that would be predicted to inactivate the kinase have been detected in BPK/atk in patients with XLA (Vetrie et al., *Nature* 361:226–233 (1993)). Therefore BPK/atk is likely to play a critical role in B-cell signalling. The possibility that tec is involved in a more specialized responses of myeloid cells is currently being examined.

We have also not observed evidence for a role for the c-fes gene in Epo signal transducing pathways that regulate cell proliferation. Recent studies have suggested that c-fes may be involved in the terminal differentiation of myeloid cells (Borellini et al., *J. Biol. Chem.* 266:15850–15854 (1991)) since the levels of c-fes expression increase with differentiation, introduction of an activated form of c-fes into myeloid cells promotes their differentiation (Borellini et al., *J. Biol. Chem.* 266:15850–15854 (1991)) and c-fes antisense constructs interfere with differentiation (Ferrari et al., *Cell Growth Differ.* 1:543–548 (1990)).

In contrast to the results obtained with lyn, tec or fes, the experiments with Jak2 readily demonstrated an effect on tyrosine phosphorylation, activation of kinase activity and the ability to associate with EpoR. Moreover, the results were quite striking in the specificity for Jak2 relative to Jak1. Jak1 and Jak2 are highly related and have considerable amino acid sequence identity in both the catalytic domains as well as the amino terminal region (Harpur et al., *Oncogene* 7:1347–1353 (1992); see also Example 1 herein). The amino acid sequence of Jak2 encodes a protein of 1129 amino acids with a calculated size of 130 kDa which has 45.5% identity with the murine Jak1 kinase.

Although there was a clear specificity for Jak2 in our studies, Jak1 was consistently detected in all assays at low levels. This was not due to cross-reactivity of the antisera since all the antisera used were against peptides from regions that do not contain extensive amino acid identity. In addition the lack of cross-reactivity of the antisera has been established by examining the reactivity with in vitro translated proteins (see Example 1). The difference in reactivity is also not due to differences in the levels of the expression of the two kinases, since both are expressed at comparable levels. Therefore, there appears to be sufficient similarity between Jak1 and Jak2 to allow Jak1 to associate with EpoR but with a much lower affinity.

Epo induction of Jak2 tyrosine phosphorylation was assessed by changes in reactivity with monoclonal antibodies against phosphotyrosine. Importantly, tyrosine phosphorylation was readily demonstrable with both the 4G10 and PY20 monoclonal antibodies by Western blotting techniques. In addition, Jak2 could be isolated from Epo stimulated cells, but not from unstimulated cells, by affinity purification with the 1G2 anti-phosphotyrosine monoclonal antibody coupled to sepharose. These approaches are commonly used to detect changes in protein tyrosine phosphorylation.

Our results demonstrate that Epo stimulation activates the in vitro kinase activity of Jak2 and that the primary substrate is Jak2. Previous studies have found it difficult to demonstrate the kinase activity of Jak1. In particular Wilks et al., *Mol. Cell. Biol.* 11:2057–2065 (1991) were unable to demonstrate protein tyrosine kinase activity in immunoprecipitates of Jak1 under a variety of conditions. However, they were able to demonstrate protein tyrosine phosphorylation in bacteria with an expression construct containing a fusion protein with the carboxyl kinase domain of Jak1. A comparable fusion protein containing the amino terminal kinase-like domain had no activity. Interestingly, relatively few bacterial proteins were phosphorylated, suggesting that Jak1 may have a restricted substrate specificity. Our results would suggest that the inability to detect in vitro Jak1 kinase activity is due to lack of appropriate activation in vivo since the ability to detect Jak2 kinase activity was absolutely dependent upon stimulation of the cells with Epo. In this regard, we have been unable to demonstrate Jak1 in vitro kinase activity although Jak1 appears to weakly associate with EpoR and is weakly tyrosine phosphorylated following Epo stimulation.

The primary substrate of tyrosine phosphorylation in the in vitro reactions was Jak2 and specifically no phosphorylation of the immunoglobulin heavy chain was detected. This suggests that Jak2 may have very specific substrate specificities. Regarding the mechanism of Jak2 activation, it is possible that ligand binding promotes Jak2 association such that intermolecular phosphorylations occur and result in the activation of kinase activity. Activated Jak2 then has the ability to continue such intermolecular phosphorylations in vitro in immunoprecipitates in a manner that is completely analogous to the receptor protein tyrosine kinases (Ohtsuka et al., *Mol. Cell Biol.* 10:1664–1671 (1990); Yarden and Schlessinger, *Biochemistry* 26:1434–1442 (1987)).

Epo stimulation results in the rapid tyrosine phosphorylation of the EpoR receptor with kinetics that are comparable to that of the tyrosine phosphorylation of Jak2. This indicates that Jak2 is the kinase that is responsible for the EpoR phosphorylation. Phosphorylation of EpoR occurs in the membrane distal carboxyl domain, a region that is not required for mitogenesis. This phosphorylation does not occur in mutants containing a 20 amino acid deletion in the membrane proximal region or with the $W^{282}$->R mutation in this region. Since both of these mutations also affect Jak2 phosphorylation and kinase activation and the amino acid deletion eliminates the ability of Jak2 to associate with EpoR in vitro, it is likely that Jak2 is the kinase responsible for EpoR phosphorylation. Alternatively, another kinase may associate with Jak2 and thereby be brought into the region of the receptor. If so this additional kinase may also be required for the phosphorylation of Jak2.

With the exception of Jak2 and EpoR, relatively little is known concerning the substrates of Epo induced tyrosine phosphorylation. Substrates of 92 kDa, 70 kDa and 55 kDa have been consistently detected in our studies (Miura et al., *Mol. Cell Biol.* 11:4895–4902 (1991)) and others have identified similar as well as additional substrates (Damen et al., *Blood* 80:1923–1932 (1992); Quelle and Wojchowski, *J. Biol. Chem.* 266:609–614 (1991); Quelle et al., *J. Biol. Chem.* 267:17055–17060 (1992); Linnekin et al., *Proc. Natl. Acad. Sci. USA* 89:6237–6241 (1992); Dusanter-Fourt et al., *J. Biol. Chem.* 267:10670–10675 (1992)). It is also important to note that there are readily detectable substrates of inducible tyrosine phosphorylation of 55 and 70 kDa that co-immunoprecipitate with Jak2. We have excluded a number of potentially interesting substrates including vav, rat, GAP and SHC. However, we have not examined the ISGF3α proteins of 113 and 91/84 kDa which may be substrates of the Jak family kinase Tyk2 and which are involved in the INFα response (Schindler et al., *Science* 257:809–813 (1992); Fu, X. Y., *Cell* 70:323–335 (1992)). Alternatively, related proteins may exist that interact with Jak2 which specifically mediate the transcriptional activation of the genes associated with the response to Epo.

Previous studies identified a 130 kDa phosphoprotein that associates with the EpoR (Yoshimura and Lodish, *Mol. Cell.*

*Biol.* 12:706–715 (1992)). By cross-linking, it was shown to be associated with EpoR suggesting the possibility that it was a subunit of a receptor complex comparable to the β chain of the IL-3 or GM-CSF receptor or the pp130 chain of the IL-6 receptor. However, unlike these proteins, the p130 was not N-glycosylated suggesting that it might be a cytosolic protein. The tyrosine phosphorylation of p130 was demonstrated by immunoprecipitation with an anti-phosphotyrosine antibody. However it was not possible to determine whether tyrosine phosphorylation was induced by Epo because of the procedures used to isolate the EpoR/p130 complex. Irrespective, the properties of the p130 are consistent with the hypothesis that it is Jak2.

Our results demonstrate that Jak2 tyrosine phosphorylation and receptor association requires a membrane proximal region that is essential for mitogenesis. This was most strikingly illustrated by the deletion mutant (PB) and by the $W^{282}$->R point mutant, both of which are mitogenically inactive and concomitantly fail to couple to Jak2 tyrosine phosphorylation or activation of kinase activity. However, only the mutant with the 20 amino acid deletion (PB) lost the ability to physically associate with Jak2. It is likely that the point mutation is sufficient to disrupt a functional interaction of EpoR and Jak2 in vivo, but does not sufficiently lower the affinity of the interaction to eliminate physical interaction in vitro at high protein concentrations.

Our results suggest that Jak2 association with EpoR is independent of ligand binding. Therefore it can be hypothesized that Jak2 phosphorylation occurs as a consequence of changes affecting the receptor/Jak2 complex. Considerable evidence supports the hypothesis that Epo binding induces dimer- and oligomerization of the receptor and that this is critical for receptor function (Watowich et al., *Proc. Natl. Acad. Sci. USA* 89:2140–2144 (1992)). This is supported by the existence of a mutant EpoR ($R^{199}$->C) which results in constitutive activation of the receptor (Yoshimura et al., *Nature* 348:647–649 (1990)). This mutation requires the cysteine conversion and results in the ability to form disulfide-linked oligomers in the absence of ligand (Watowich et al., *Proc. Natl. Acad. Sci. USA* 89:2140–2144 (1992)). In cells expressing this mutation, in the absence of Epo, Jak2 kinase is constitutively tyrosine phosphorylated and has in vitro kinase activity. Based on these data, we would further hypothesize that Epo binding causes oligomerization of the EpoR/Jak2 complexes, bringing the kinase molecules in sufficient proximity to result in intermolecular tyrosine phosphorylations. This model is identical to that proposed for several receptor protein tyrosine kinases (Ullrich and Schlessinger, *Cell* 61:203–212 (1990)).

Studies with the IFNα receptor have suggested that high affinity binding may require the association of Tyk2 (Firmbach-Kraft et al., *Oncogene* 5:1329–1336 (1990)). This possibility also exists for EpoR. In particular, since Jak2 is ubiquitously expressed, the binding affinities of the receptor have not been measured in the absence of Jak2.Moreover, as demonstrated here, EpoR can functionally associate with Jak2 in fibroblasts. Therefore it will be necessary to express the receptor in phylogenetically distant cells which do not contain a Jak kinase with sufficient homology to associate with the receptor. Under such conditions, it should be possible to address the role of Jak2 binding on the affinity of the receptor.

Jak family kinases are ubiquitously expressed (Wilks et al., *Mol. Cell. Biol.* 11:2057–2065 (1991); see also Example 1). Therefore it was important to determine whether, in fibroblasts, expression of the EpoR was sufficient to couple to activation of tyrosine phosphorylation. As demonstrated, tyrosine phosphorylation of both EpoR and Jak2 was detected following Epo stimulation. Due to the high background of protein tyrosine phosphorylation in the cells used, we were not able to determine whether Epo stimulation resulted in the tyrosine phosphorylation of other cellular substrates. However, Epo stimulation of serum starved cells, does not induce a mitogenic response suggesting that some components required for coupling ligand binding to cell proliferation are missing. Alternatively, insufficient receptors may be expressed. In contrast, a recent report (Watanabe et al., *Mol. Cell. Biol.* 13:1440–1448 (1993)) demonstrated that a reconstituted GM-CSF receptor complex in fibroblasts can transduce a growth-promoting signal.

The membrane proximal region of the Epo receptor with which Jak2 associates contains limited sequence similarity with other hematopoietic growth factor receptors (Murakami et al., *Proc. Natl. Acad. Sci. USA* 88:11349–11353 (1991)). In all cases examined, this region has been shown to be essential for mitogenesis. Thus it will be important to determine whether other members of the hematopoietic cytokine receptor superfamily associate with Jak2, or possibly another member of the Jak family of kinases. In this regard, we have found that IL-3, GM-CSF and G-CSF also induce the specific tyrosine phosphorylation of Jak2.It will be important to further explore the role of Jak family kinases in the responses to other cytokines including IL-2, IL-4 and IL-6.

The ubiquitous expression of the Jak kinases further indicates that they may couple ligand binding to mitogenesis with other non-hematopoietic members of the cytokine receptor superfamily. It has been recognized that there exists structural relationships in the extracellular domains of endocrine growth hormones, the hematopoietic cytokine receptors and a more distant possible relationship with the receptors for tissue factor and interferons (Bazan, J. F., Immunol. Today 10:350–354 (1991); Bazan, J. F., *Proc. Natl. Acad. Sci. USA* 87:6934–6938 (1990); De Vos et al., *Science* 255:306–312 (1992)). If these relationships reflect a divergent evolution of a class of signaling receptors, it is possible that they couple signal transduction in a similar manner through interactions with members of the Jak kinase family. Thus the INFα receptor couples through Tyk2 while the receptors for IL-3, GM-CSF, G-CSF and Epo couple through Jak2.Consistent with this we have found that IFNγ induces the tyrosine phosphorylation of Jak2 in a macrophage cell line. In addition recent studies have found that the growth hormone receptor binds to and activates Jak2.It will be of considerable interest to identify which of the Jak kinases other members of the cytokine receptor superfamily associate with and activate.

It will also be of interest to determine whether the Jak family of kinases utilize similar mechanisms to affect gene regulation. Considerable evidence suggests that Tyk2 couples INFα/β binding to tyrosine phosphorylation of the 113 kDa and 91/84 kDa proteins of the ISGF3α (interferon-stimulated gene factor 3) complex (Fu, X. Y., *Cell* 70:323–335 (1992)). Following phosphorylation this complex associates with the 48 kDa ISGF3γ protein and the complex migrates to the nucleus where it binds the interferon-stimulated response element and activates gene expression. Recent studies (Shuai et al., *Science* 259:1808–1812 (1992)) have demonstrated that IFNγ also induces tyrosine phosphorylation of the 91 kDa protein, but not of the 113 kDa protein, and that it migrates to the nucleus and binds a γ-activated site. As noted above, Jak2 is inducibly tyrosine phosphorylated following IFNγ binding and thus may be the kinase involved. If correct, stimulation of cells with Epo, IL-3, GM-CSF or G-CSF may result in the tyrosine phosphorylation of the 91 kDa ISGF3γ protein or a member of this gene family. In this regard it is important to note that one of the major substrates of tyrosine phosphorylation seen in response to Epo or IL-3 is a protein of approximately 92 kDa (Miura et al., *Mol. Cell Biol.* 11:4895–4902 (1991); Miura et al., *Mol. Cell. Biol.* 13:1788–1795 (1993)). From the above, it can by hypothesized that members of the cytokine receptor superfamily couple ligand binding to inducing gene expression, in part, by the activation of Jak family kinases by autophosphorylation following ligand binding which results in the phosphorylation of members of the ISGF3γ family which, in turn, associate with members of the ISGF3α family of DNA binding proteins, including ICSBP, IRF-1, IFR-2 and c-myb (Veals et al., *Mol. Cell. Biol.* 12:3315–3324 (1992)).

Experimental Procedures

Cell Lines and Culture Conditions

DA3(EpoR) cells expressing the wild type receptor and DA3 cells expressing various mutations were maintained on RPMI-1640 supplemented with 5 mM glutamine, 10% FCS 1 U/mi Epo and G418 as previously described (Miura et al., *Mol. Cell Biol.* 11:4895–4902 (1991)). Starvation of cells was done by washing cells with PBS three times and incubating in RPMI-1640 supplemented with 5 mM glutamine and 10% FCS in the absence of growth factor for 12 to 16 hr. Cells were stimulated with 10–30 U/ml Epo.

Reagents

The preparation and properties of rabbit polyclonal antisera against peptides from Jak1 and Jak2 is described in Example 1.The antiserum against c-fes was kindly provided by J. Downing (St. Jude Children's Research Hospital, Memphis) and its properties have been described (Haynes and Downing, *Mol. Cell. Biol.* 8:2419–2427 (1988)). The antiserum against lyn has also been described (Yi et al., *Mol. Cell. Biol.* 11:2391–2398 (1991)). The antiserum against murine Tec was prepared against GST-fusion proteins and specifically immunoprecipitates a 70 kDa protein from cells expressing Tec but not from control cells. Antiphosphotyrosine monoclonai antibodies included 4G10 (UBI), 1G2 (Oncogene Sciences) and PY20 (ICN) which were purchased from commercial sources. Human Epo was provided by Amgen.

Transfection of 3T3 cells with the pXM EpoR

The plasmid pXM-EpoR (D'Andrea et al., *Cell* 57:277–285 (1989b)) was transfected into 3T3 fibroblast by electroporation as previously described (Miura et al., *Mol. Cell Biol.* 11:4895–4902 (1991)). The cells were maintained in Delbecco's modified Eagles Media (DMEM) with 10% FCS. In the experiments the cells were starved of growth factors by culturing overnight in media containing 0.5% FCS. The cells were subsequently stimulated with Epo (3 U/ml) in the same medium.

Construction of Fusion Proteins

Bacterially expressed fusion proteins were prepared which contain an amino-terminal glutathione-S-transferase (GST) domain and a carboxyl portion of the murine EpoR cytoplasmic domain. Constructs containing the full length EpoR cytoplasmic domain (amino acids 257–483) were prepared by inserting a blunt-ended BglII-KpnI fragment of the EpoR cDNA into the SmaI site of pGEX-2T. Constructs containing the membrane proximal cytoplasmic domain of EpoR (amino acids 257–375) were obtained by inserting a blunt-ended BglII-HindIII fragment of the EpoR cDNA into the SmaI site of pGEX-2T. Identical constructs were prepared using EpoR cDNAs containing the PB and PM-4 mutations previously described (Miura et al., *Mol. Cell Biol.* 11:4895–4902 (1991)). Fusion proteins then were obtained from *E. coli* strain DH5-alpha transformed with the plasmid constructs and were affinity-purified on glutathione-sepharose (Pharmacia) as previously described (Smith and Johnson, *Gene* 67:31–40 (1988)).

Fusion Protein Binding Assays

Following growth factor stimulation, cells were lysed at $5 \times 10^7$ cells/ml in lysis buffer [1% Triton X-100, 50 mM NaCl, 30 mM $Na_4P_2O_7$, 50 mM NaF, 0.1 mM $Na_3VO_4$, 5 mM EDTA, 0.1% bovine serum albumin (BSA), 0.05 mg/ml phenylmethylsulphonyl fluoride (PMSF), 10 mM Tris pH 7.6]. Lysates were cleared of debris at 12,000×g for 10 min and were subsequently incubated with GST-EpoR fusion proteins immobilized on glutathione sepharose. Resins were extensively washed in lysis buffer without BSA and associated proteins then were eluted with sample buffer for SDS-PAGE. Eluted proteins were separated on 8% SDS-PAGE gels and immunoblotted with various antisera.

In Vitro Kinase Assays

Immunoprecipitated proteins on Protein A-Sepharose (Pharmacia) were washed with kinase buffer (50 mM NaCl, 5 mM $MgCl_2$, 5 mM $MnCl_2$, 0.1 mM $Na_3VO_4$, 10 mM HEPES pH 7.4) and subsequently were incubated for 30 min at room temperature with an equal volume of kinase buffer containing 0.25 mCi/ml $^{32}$P-γ-ATP. After extensive washing, proteins were eluted with sample buffer for SDS-PAGE and separated on 7% gels. $^{32}$P-containing proteins were visualized by autoradiography. In vitro phosphorylated Jak2 was isolated from gel slices and the phosphoamino acid content determined by published procedures (Cooper et al., *Methods Enzymol.* 99:387–402 (1983)).

Immunoprecipitation, SDS-PAGE and Western Blotting

Cells were harvested and lysed for 20 min in 1 ml of ice cold lysis buffer (50 mM) Tris-HCl (pH 7.5), 150 mM NaCl, 1% (vol/vol) Triton-X 100, 100 μM sodium vanadate, 1 mM phenylmethylsulfonylfluoride, and 1 mM EDTA. Lysates were pre-cleared by centrifugation for 30 min at 4° C. Supernatant was removed and incubated with preimmune serum and protein A-Sepharose (40 μl of 50% slurry) for 1 hr. The designated serum or monoclonal antibody were then added and incubated at 4° C. for 1–2 hr. Protein A-Sepharose (40 μl of 50% slurry) was added when required, the immunoprecipitates were washed three times in 1 ml of cold lysis buffer, resuspended in Lamelli's samples buffer 10% (vol/vol) glycerol, 1 mM DTT, 1% (wt/vol) SDS, 50 mM M Tris-HCl (pH 6.8) and 0.002% (wt/vol) bromophenol blue and subjected to 7.5% SDS-PAGE. Gels were then transferred electrophoretically to nitrocellulose. The filters were incubated for 2 hr in blotto (5% dehydrated milk in TBSS, 10 mM Tris-HCl pH 7.6 and 137 mM NaCl), then incubated in relevant primary antibody for 1 hr, rinsed in TBSS and incubated for 1 hr in horseradish peroxidase (Amersham) or alkaline phosphatase (Promega) conjugated anti-mouse or anti-rabbit. The filters were then washed and exposed to ECL™ (Amersham Life Science) or 5-bromo-4-chloro-3-indoyl phosphate/nitroblue tetrasodium detection. The ECL detection was subsequently recorded on Kodak XAR-5 film. Competition studies using synthetic peptides were done by incubating the antiserum with 100 μg/ml of peptide for 1 hr at 4° C. prior to adding the mixture to cell lysates or dilution in solutions for Western blotting.

Example 3

Identification of Jak2 as a growth hormone receptor-associated tyrosine kinase

Summary

Growth hormone receptor (GHR) forms a complex with a tyrosine kinase, suggesting involvement of a ligand-activated tyrosine kinase in intracellular signaling by growth hormone (GH). Here we identify Jak2, a nonreceptor tyrosine kinase, as a GHR-associated tyrosine kinase. Immunological approaches were used to establish GH-dependent complex formation between Jak2 and GHR, activation of Jak2 tyrosine kinase activity, and tyrosyl phosphorylation of both Jak2 and GHR. The Jak2-GHR and Jak2-erythropoietin receptor interactions described here and in the accompanying Example 2 provide a molecular basis for the role of tyrosyl phosphorylation in physiological responses to these ligands, thus evidencing shared signaling mechanism among members of the cytokine/hematopoietin receptor family.

Introduction

Although the ability of growth hormone (GH) to promote growth and regulate metabolism has been known for many years (Cheek, D. B. and Hill, D. E., "Effect of growth hormone on cell and somatic growth," in E. Knobli and W. H. Sawyer, eds., *Handbook of Physiology*, Vol. 4:159–185, Washington, D.C. (1974); Davidson, M. B., *Rev.* 8:115–131 (1987)), the molecular mechanism by which GH binding to its receptor elicits its diverse responses has remained an enigma. New insight into GH signaling mechanisms was recently provided by the demonstration that a tyrosine kinase activity is present in a complex with GH receptor (GHR) prepared from GH-treated fibroblasts (Carter-Su., C. et al., *J. Biol. Chem.* 264:18654–18661 (1989); Stred, S. E. et al., *Endocrinol.* 130:1626–1636 (1992); Wang, X. et al., *J. Biol. Chem.* 267:17390–17396 (1992)). Additional studies in 3T3-F442A cells showing rapid GH-dependent tyrosyl phosphorylation of multiple proteins, tyrosyl phosphorylation of microtubule-associated protein kinases, and stimulation of microtubule-associated protein kinase activity, as well as the inhibition of these actions by inhibitors of the GHR-associated tyrosine kinase (Campbell, G. S. et al., *J. Biol. Chem.* 268:7427–7434 (1993)), suggest a central role for a GHR-associated tyrosine kinase in signaling by GH. Recently, a nonreceptor tyrosyl phosphorylated 122 kd protein was identified in a kinase-active GH-GHR preparation (Wang, X. et al., *J. Biol. Chem.* 268:3573–3579 (1993)). Since autophosphorylation is often a manifestation of an activated kinase, it was hypothesized that this 121 kd phosphoprotein is the GHR-associated kinase.

In this study, we identify Jak2, a 130 kd tyrosine kinase (Harpur, A. G. et al., *Oncogene* 7:1347–1553 (1992)) as a GHR-associated kinase. Jak2 is a member of the recently described Janus family of tyrosine kinases including Jak1, Jak2, and Tyk2. In addition to having a kinase domain, these proteins are characterized by the presence of a second kinase-like domain and the absence of Src homology 2 (SH2), SH3, and membrane-spanning domains (Wilks, A. F. et al., *Mol. Cell. Biol.* 11:2057–2065 (1991); Firmbach-Kraft, L et al., *Oncogene* 5:1329–1336 (1990); Harpur, A. G. et al., *Oncogene* 7:1347–1553 (1992)).

Here we show that GH binding promotes association of Jak2 with GHR, activation of Jak2, and tyrosyl phosphorylation of both Jak2 and GHR. The identification of Jak2 as a signaling molecule early in the GHR signal transduction pathway provides important insight into signaling by GHR and into the function of Jak2. Work presented in the accompanying Example 2 indicates that Jak2 also associates with the receptor for erythropoietin (Epo), and other data indicate that at least four other members of the cytokine/hematopoietin receptor family (receptors for interleukin [IL]-3), granulocyte-macrophage colony-stimulating factor [GM-CSF], granulocyte colony-stimulating factor [G-CSF], and prolactin) and the more distantly related IFN-γ receptor activate Jak2 (see accompanying Examples). It therefore seems likely that the Jak2-GHR and Jak2-Epo receptor interactions shown herein serve as prototypes for signaling through many members of this large receptor superfamily.

Results

GH Stimulates Tyrosyl Phosphorylation of Jak2

On the basis of previous studies establishing the existence of a GHR-associated tyrosine kinase (Carter-Su., C. et al., *J. Biol. Chem.* 264:18654–18661 (1989); Stred, S. E. et al., *Endocrinol.* 130:1626–1636 (1992); Wang, X. et al., *J. Biol. Chem.* 268:3573–3579 (1993); Campbell, G. S. et al., *J. Biol. Chem.* 268:7427–7434 (1993)), the GHR-associated tyrosine kinase would be expected; first, to be a protein of 120 kd; second, to be tyrosyl phosphorylated in response to GH; third, to be present in a complex with GHR; and fourth, to exhibit increased activity in response to GH.

Jak2 is a tyrosine kinase of the correct size ($M_r$ of 130,000; see example 1) to be the GHR-associated kinase and was therefore tested for its ability to be phosphorylated in response to GH. Solubilized proteins from GH-treated 3T3-F442A fibroblasts were immunoprecipitated using antiserum to Jak2 (αJak2) and analyzed by anti-phosphotyrosine antibody (αPY) immunoblot. Cells were incubated with varying physiological concentrations of GH in ranging in 10-fold increments from 0.5 ng/ml to 500 ng/ml (the standard concentration used) for 0, 0.5, 5, 50, and 60 minutes.

GH-dependent tyrosyl phosphorylation of a protein with an $M_r$ (130,000) appropriate for Jak2 was clearly evident at times as early as 30 seconds and at physiological concentrations of GH as low as 5.0 ng/ml (230 pM). Phosphorylation was transient, being greatly diminished by 60 min after addition of GH. The 130 kd phosphoprotein was detected in αPY immunoblasts of αJak2 immunoprecipitates. The appearance of this 130 kd protein corresponded in time course and GH dose response with the appearance in whole-cell lysates of a tyrosyl-phosphorylated protein designated pp121 in previous work (Campbell, G. S. et al., *J. Biol. Chem.* 268:7427–7434 (1993); Wang, X. et al., *J. Biol. Chem.* 268:3573–3579 (1993)). The identity of these two proteins is suggested by their comigration in cell lysates of tyrosyl phosphorylated pp121 and Jak2 and depletion of tyrosyl-phosphorylated pp121 from cell lysates following immunoprecipitation with αJak2.

The 130 kd phosphoprotein was precipitated specifically by αJak2. Nonimmune serum, an unrelated immune serum (αG-LUT-1), and αJak2 preadsorbed with the peptide used to make the antibody failed to immunoprecipitate pp130. Preadsorption of αJak2 with the analogous peptide from murine Jak1 (see Example 1) did not interfere with precipitation of the 130 kd phosphoprotein by αJak2. In contrast with these results using αJak2, immunoprecipitation of 3T3-F442A and IM-9 cell lysates, respectively, with antibodies specific for Jak1 (αJak1) and Tyk2 (αTyk2) revealed little (αJak1) or no (αTyk2) GH-dependent tyrosyl phosphorylation of a 130 kd protein, despite the presence of these kinases in the respective cell types.

Tyrosyl phosphorylation of the 130 kd protein precipitated from 3T3-F442A cells by αJak2 was increased specifically by GH. Phosphorylation was not increased by platelet-derived growth factor, epidermal growth factor, or insulin-like growth factor 1. These growth factors stimulate tyrosine kinase activity intrinsic to their receptors (Ulrich, A. and Schlessinger, J., *Cell* 61:203–212 (1990)) and promote tyrosyl phosphorylation of multiple proteins in 3T3-F442A fibroblasts (Campbell, G. S. et al., *J. Biol. Chem.* 268:7427–7434 (1993)). The inability to stimulate Jak2 tyrosyl phosphorylation is consistent with the previously reported inability of these growth factors to stimulate tyrosyl phosphorylation of pp121 in whole-cell lysates (Campbell, G. S. et al., *J. Biol. Chem.* 268:7427–7434 (1993)).

Jak2 Associates with the GH Receptor

To determine whether Jak2 forms a complex with GHR, GH-GHR complexes and associated proteins were immunoprecipitated from solubilized, GH-treated 3T3-F442A fibroblasts using antibody to GH (αGH). The presence of Jak2 in αGH immunoprecipitates was assessed either by immunoblotting with αJak2 or by immunoprecipitating with αJak2 and immunoblotting with αPY. When material precipitated using αGH was analyzed, αJak2 was found to immunoblot a 130 kd protein and to immunoprecipitate a tyrosyl-phosphorylated 130 kd protein that comigrates with a protein recognized by αJak2, indicating that Jak2 associates with GH-GHR complexes. When instead of αGH, the initial immunoprecipitation was performed with antibody to either the cytoplasmic or extracellular domains of GHR (αGHR), αJak2 recognized a 130 kd protein only when cells had been incubated with GH. Consistent with the presence of Jak2 in the αGHR precipitate because of its association with GH-bound GHR, no signal was detected in αJak2 immunoblots of αGH immunoprecipitates when cells had not been incubated with GH nor when immunoprecipitation was performed using an unrelated immune serum (αGLUT-1). These results provide evidence that GH binding to its receptor is necessary to the formation of a complex between GHR and Jak2.

In addition to the 130 kd phosphoprotein believed to be Jak2, a diffusely migrating phosphoprotein of 120 kd identified by αPY immunoblot was precipitated by αGH, αGHR, and to a lesser extent by αJak2. Consistent with this diffuse band being GHR, its size corresponds to that previously reported for GHR in these cells (Schwartz, J. and Carter-Su, C., *Endocrinology* 122:2247–2256 (1988); Stred, S. E. et al., *Endocrinol.* 130:1626–1636 (1992)), and it comigrates with a similarly diffuse 120 kd band identified by αGHR in Western blots of αGH immunoprecipitates. The finding that tyrosyl residues are phosphorylated in the diffuse 120 kd protein present in αGHR immunoprecipitates only when the cells have been incubated with GH offers evidence that tyrosyl phosphorylation of GHR, like tyrosyl phosphorylation of Jak2, is GH dependent. Additional evidence that both Jak2 and GHR are tyrosyl phosphorylated in response to GH is provided by the finding that in a transfected Chinese hamster ovary cell line (CHO4) that expresses a smaller (84 kd) GHR (Eminer, M. et al., *Mol. Endocrinol.* 4:2014–2020 (1990); Wang, X. et al., *J. Biol. Chem.* 268:3573–3579 (1993)), tyrosyl phosphorylation of a 130 kd protein in αGH, αGHR, and αJak2 immunoprecipitates and a diffusely migrating 84 kd protein in αGH and αGHR immunoprecipitates is GH dependent.

Stimulation by GH of Jak Kinase Activity

Previous studies have established that when αGH precipitates are prepared from GH-treated CHO4 cells, the addition of ATP results in the tyrosyl phosphorylation of both a 130 kd and a 84 kd protein (Wang, X. et al., *J. Biol. Chem.* 268:3573–3579 (1993)). To determine whether the 130 kd and 84 kd proteins phosphorylated in this in vitro kinase assay are Jak2 and GHR, respectively, GH-GHR complexes and associated proteins were precipitated from GH-treated and control CHO4 cells using αGH, incubated with [γ-$^{32}$P]ATP, dissociated by boiling in buffer containing SDS, β-mercaptoethanol, and dithiothreitol (DTT), and reprecipitated using either αJak2 or αGHR. In this experiment αJak2 was able to precipitate a 130 kd $^{32}$P-labeled protein appropriate for Jak2, and αGHR was able to precipitate an 84 kd $^{32}$P-labeled protein appropriate for GHR, indicating that both Jak2 and GHR incorporate $^{32}$P in the in vitro kinase assay.

To verify that Jak2 functions as a GH-dependent tyrosine kinase, Jak2 was purified from GH-treated and control 3T3-F442A cells either by direct immunoprecipitation with αJak2 or, to permit a higher degree of purification, by sequential immunoprecipitation using αPY followed by αJak2. When the αJak2 immune complexes were incubated with [γ-$^{32}$P]ATP, $^{32}$P-labeled proteins migrating with a M$_r$ (130,000) appropriate for Jak2 were detected only when the cells had been incubated with GH, indicating an exquisite sensitivity of Jak2 to activation by GH. To verify that Jak2 incorporates phosphate into tyrosyl residues, phosphoamino acid analysis was performed on the $^{32}$P-labeled 130 kd protein isolated from GH-treated 3T3-F442A cells. $^{32}$P was found incorporated almost exclusively into tyrosyl residues, consistent with Jak2 being a GH-sensitive tyrosine kinase. However, the incorporation of a small amount of $^{32}$P (under 1%) into threonine residues in the αJak2 immunoprecipitate leaves open the possibility that Jak2 is a mixed function threonine/serine/tyrosine kinase.

Discussion

Identification of Jak2 As a Signaling Molecule for GHR

The identification of Jak2 as a GH-dependent, GHR-associated tyrosine kinase has important implications for signal transduction by both GHR and Jak2. With regard to GHR, Jak2 is identified as a signaling molecule that interacts with GHR and is activated in response to GH binding. Its sensitivity to GH and rapid onset following GH addition make tyrosyl phosphorylation of Jak2 among the most sensitive and rapid responses known for GH; activation of Jak2 is an initiating step for GH signal transduction.

Tyrosine kinases have been shown to elicit responses similar to those attributable to GH, including metabolic responses (e.g., insulin receptor) and differentiation (e.g., nerve growth factor receptor) (reviewed by Davidson, M. B., *Rev.* 8:115–131 (1987); Isaksson, O. G. P. et al., *Endocrinol. Rev.* 8:426–438 (1987); Levi-Montaicini, R., *Science* 237:1154–1162 (1987); Kaplan, D. R. et al., *Science* 252:554–558 (1991)). Therefore, Jak2 plays a vital role in eliciting the known responses to GH. Consistent with this, no biological functions, other than binding of GH, have been reported for GHR expressed in cells that have low levels of GHR-associated tyrosine kinase activity (e.g., COS-7 and mouse L cells; Leung, D. W. et al., *Nature* 330:537–543 (1987); Wang, X. et al., *J. Biol. Chem.* 267:17390–17396 (1992)). In contrast, a variety of biological functions (e.g., insulin synthesis in RIN5-AH cells and protein synthesis, microtubule-associated protein kinase activity, c-fos gene expression, and lipid synthesis in Chinese hamster ovary cells) can be activated by GH binding when the cloned liver GHR is expressed in cells that have reasonably high levels of GHR-associated kinase activity (Bitlestrup, N. et al., *Proc. Natl. Acad. Sci. USA* 87:7210–7214 (1990); Eminer, M. et al., *Mol. Endocrinol.* 4:2014–2020 (1990); Moller, C., in *Aspects of the Mechanism of Growth Hormone Action*, Ph.D. Thesis, Karolinska Institute, NO-VUM, Huddinge, Sweden (1992), pp. 1–9; Wang, X. et al., *J. Biol. Chem.* 267:17390–17396 (1992); Moller, C. et al., *J. Biol. Chem.* 267:23403–23408 (1992)).

Furthermore, in 3T3-F442A cells, multiple proteins exhibit GH-dependent increases in tyrosyl phosphorylation. Consistent with activation of Jak2 being required for these phosphorylations, tyrosyl phosphorylation of Jak2/pp121 is simultaneous with or precedes tyrosyl phosphorylation of all the proteins exhibiting GH-dependent tyrosyl phosphorylation, at all GH concentrations tested (this work and Campbell, G. S. et al., *J. Biol. Chem.* 268:7427–7434 (1993)).

Jak2 serves as a signaling molecule for GHR by phosphorylating other proteins. Two proteins have been identified as substrates of Jak2: Jak2 itself and GHR.

Studies using truncated GHR indicate that in the cytoplasmic domain of the GHR, at least 1 of the 4 tyrosyl residues most proximal to the membrane is phosphorylated in response to GH. Studies are underway to identify which of the 4 tyrosines are phosphorylated by Jak2, as well as to identify tyrosines in the C-terminal portion of GHR that might also be phosphorylated. It is important to determine the identity and number of tyrosines phosphorylated in Jak2 and GHR, because these sites are likely to be binding sites for SH2-containing proteins (e.g., phospholipase C-$\gamma$, p85 phosphatidylinositol-3 kinase, and GTPase-activating protein; Koch, A. A. et al., *Science* 252:668–674 (1991)) in intercellular signaling pathways. Signaling pathways involving SH2-containing proteins that bind to phosphorylated Jak2 would be expected to be shared by all ligands that activate Jak2, whereas SH2-containing proteins that bind to phosphorylated tyrosyl residues in GHR could provide specificity to a signaling mechanism that utilizes a kinase (i.e., Jak2) with the apparent capacity to service more than one receptor (see below).

Jak2 has also been shown to be activated following the binding of Epo to its receptor (Example 2). Other data indicate that IL-3, GM-CSF, G-CSF, IFN-$\gamma$, and prolactin also activate Jak2 (see Example 1). Thus, Jak2 serves as a kinase for multiple members of the cytokine/hematopoietin receptor family. Since each ligand elicits a separate constellation of responses, kinase activation alone cannot account for specificity. As mentioned above, a set of responses dependent upon phosphorylation of the receptor could provide the specificity. Additionally, specificity could be obtained by interaction between multiple signaling pathways or by the expression of only one receptor type in a particular cell type. This latter mechanism is suggested by the ability of GH, G-CSF, and Epo to stimulate proliferation of IL-3-dependent cells transfected with the cDNA from the appropriate receptor (Fukunaga, R. et al., *EMBO J.* 10:2855–2865 (1991); Ishizaka-Ikeda, E. et al., *Proc. Natl. Acad. Sci. USA* 90:123–127 (1993); Yoshimura, A. et al., *Proc. Natl. Acad. Sci. USA* 87:4139–4143 (1990)).

The commonality of Jak2 activation suggests that there will be shared pathways activated by the ligands that bind Jak2-coupled receptors. Of particular interest for gaining insight into regulation of gene transcription by GH is a pathway initiated by IFN-$\gamma$. In response to IFN-$\gamma$, the 91 kd protein of the ISGF-3 (IFN-stimulated gene factor 3) complex undergoes tyrosyl phosphorylation and then translocates to the nucleus, where it binds to DNA at the $\gamma$-activated site (Shuai, K. et al., *Science* 258:1808–1812 (1992)). Identification of the 90 kd protein phosphorylated in response to GH (Campbell, G. S. et al., *J. Biol. Chem.* 268:7427–7434 (1993)) as the 91 kd protein of the ISGF-3 complex or a family member would implicate one pathway by which GH might elicit some of the effects on gene transcription.

Activation of Jak2 by GH

The exact mechanism by which GH activates Jak2 is not yet known. Earlier studies using an exogenous substrate (poly Glu, Tyr) established that more tyrosine kinase activity is present in a complex with GHR when GHR is prepared from GH-treated cells than from control cells (Stred, S. E. et al., *Endocrinol.* 130:1626–1636 (1992)). The present study suggests that this GH-induced increase in kinase activity results from both an increase in affinity of GHR for Jak2 and an increase in Jak2 activity. Jak2 appears to bind directly to GHR, since only two proteins, migrating with sizes appropriate for Jak2 and GHR, are visualized when highly purified kinase-active GH-GHR complexes are isolated from GH-treated $^{35}$S-labeled 3T3-F442A fibroblasts by sequential immunoprecipitation using $\alpha$PY and then either $\alpha$GHR or $\alpha$GH (Stred, S. E. et al., *Endocrinol.* 130:1626–1636 (1992)). The mechanism by which GH promotes association of Jak2 with GHR and Jak2 activation is likely to require dimerization of GHR, since GH-induced tyrosyl phosphorylation of cellular proteins appears to require dimerization of GHR (Silva, C. M. et al., *Endocrinol.* 32:101–108 (1993)). An important role for receptor dimerization in signaling via Jak2 is further suggested by work relating Jak2 activation to Epo receptor dimerization discussed in Example 2.

The results reported herein provide evidence that binding of GH by GHR results in the formation of a ligand-bound GHR dimer capable of binding Jak2. Recruitment of Jak2 leads to the formation of a GH-GHR-Jak2 complex, stimulation of Jak2 tyrosine kinase activity, and tyrosyl phosphorylation of Jak2, GHR, and presumably other proteins. Whether activated Jak2 is present only in a complex with GHR or can dissociate from GHR and phosphorylate proteins that are physically distant from GHR is currently being investigated. Also under investigation is the possibility that GHR can form complexes with kinases other than, or in addition to, Jak2. Obvious candidate kinases include other members of the Jak family. In 3T3-F442A and IM-9 cells, respectively, Jak1 and Tyk2 do not appear to associate with GHR to the same extent as Jak2. However, they or other as yet unidentified Jak kinases may do so in other cell types or under different physiological conditions.

In summary, the experiments presented here, in combination with the similar findings for the Epo receptor presented in Example 2 and other receptors for IL-3, GM-CSF, G-CSF, prolactin, and IFN-$\gamma$ (see Example 1), indicate that the activation of Jak2 kinase activity by GH and Epo by a mechanism involving a Jak2-receptor complex is a prototype for signaling by many members of the cytokine/hematopoietin family receptors. The finding that GHR shares an important and early signaling molecule with other members of the cytokine/hematopoietin receptor family suggests that GH, IL-3, Epo, prolactin, GM-CSF, G-CSF and IFN-$\gamma$ are likely to share some signaling pathways. However, specificity could still be achieved, since phosphorylation of each receptor offers signaling capabilities unique to each ligand. The variable expression of individual receptors, the potential presence of only a subset of all possible signaling pathways in different cell types, and regulation of the signaling molecules in these pathways by other stimuli permits an additional level of specificity. This finding is likely to lead to the identification of new actions for GH as well as for these other cytokines.

Experimental Procedures

Materials

Stocks of 3T3-F442A and CH04 cells were kind gifts of H. Green (Harvard University, Cambridge, Mass.) and G. Norstedt (Karolinska Institute, Novum, Sweden), respectively. Recombinant human GH (hGH) was provided by Eli Lilly. Platelet-derived growth factor (recombinant human BB) and recombinant epidermal growth factor came from Collaborative Research. Recombinant insulin-like growth factor 1 was a gift of Kabi/Pharmacia. Triton X-100 (Surfact-Amps X-100) came from Pierce Chemical Company, aprotinin and leupeptin from Boehringer Mannheim, recombinant protein A-agarose from Repligan, [$\gamma$-$^{17}$P]ATP (6000 Ci/mmol) from New England Nuclear Corporation, and the enhanced chemiluminescence detection system from Amersham Corporation.

Antibodies

αGH (NIDDK-anti-hGH-1C3, lot C11981) came from the National Institute of Diabetes and Digestive and Kidney Diseases/National Hormone and Pituitary Program, University of Maryland and School of Medicine (Baltimore). αPY-Shafer was a gift of Dr. J. A. Shafer (Merck, Sharp, and Dohme Research Laboratory, West Point, Pa.; Pang, D. T. et al., Arch. Biochem. Biophys. 242:176–186 (1985)), and αPY-41G10 was purchased from UBL αJak2 was prepared in rabbits against a synthetic peptide corresponding to the hinge region between domains 1 and 2 of murine Jak2 (amino acids 758–776 (SEQ ID No.5); see Example 1). αJak1 was prepared against a synthetic peptide to a corresponding region in murine Jak1 (amino acids 786–804; see Example 1). One αGHR (αGHR-C1) was prepared in rabbits against a fusion protein composed of glutathione S-transferase fused to the cytoplasmic domain of the cloned mouse liver GHR and affinity purified using immobilized GHR cytoplasmic domain. A second αGHR (αGHBP-poly), kindly provided by Dr. W. R. Baumbach (American Cyanamid, Princeton, N.J.), was produced in rabbits using Recombinant rat GH-binding protein produced in *Escherichia coli* (Sadeghi, H. et al., *Mol. Endocrinol.* 4:1799–1805 (1990)). αTyk2 was a gift of Dr. J. J. Krolewski (Columbia University, New York). αGLUT-1 was prepared in rabbits using band 4.5 purified from human erythrocytes. It recognizes both human and rodent GLUT-1 (Tal, P. -K. et al., *J. Biol. Chem.* 265:21828–21834 (1990)).

Immunoprecipitation and Western Blotting

Cells were grown to confluence and deprived of serum overnight as described previously (Wang, X. et al., *J. Biol. Chem.* 268:3573–3579 (1993)). Cells were incubated for the indicated times with hormone or growth factor as indicated at 37° C. in 95% air, 5% $CO_2$, rinsed with three changes of ice-cold 10 mM sodium phosphate (pH 7.4), 137 mM NaCl, 1 mM $Na_3VO_4$, and scraped in lysis buffer (50 mM Tris (pH 7.5), 0.1% Triton X-100, 137 mM NaCl, 2 mM EGTA, 1 mM $Na_3VO_4$, 1 mM phenylmethylsulfonyl fluoride, 10 μg/ml aprotinin, and 10 μg/ml leupeptin) on ice. Cell lysates were centrifuged at 12,000×g for 10 min, and the resulting supernatants were incubated on ice 90 min with the indicated antibody. Immune complexes were collected on protein A-agarose during a 30–60 min. incubation at 8° C., washed three times with wash buffer (50 mM Tris (pH 7.5), 0.1% Triton X-100, 137 mM NaCl, 2 mM EGTA) and boiled for 5 min in a mixture (80:20) of lysis buffer and (250 mM Tris [pH 6.8], 10% SDS, 10% β-mercaptoethanol, 40% glycerol). Unfractionated lysates were brought to the same final concentrations of Tris, SDS, β-mercaptoethanol, and glycerol and boiled for 5 min. The immunoprecipitates and lysates were subjected to SDS-PAGE followed by Western blot analysis with the indicated antibody (1:1000 to 1:5000 dilution used) using the enhanced chemiluminescence detection system (Campbell, G. S. et al., *J. Biol. Chem.* 268:7427–7434 (1993)). In some experiments, the proteins were dissociated from the immune complexes and then reimmunoprecipitated before analysis by Western blot.

Dissociation and Reimmunoprecipitation of Immune Complexes

The immune complexes from the initial immunoprecipitation were washed once with 50 mM Tris, 137 mM NaCl (pH 7.5), brought to a final concentration of 0.75% SDS, 2% β-mercaptoethanol, 100 mM DTT, 100 μg/ml aprotinin, and 100 μg/ml leupeptin by addition of an equal volume of a 2× concentrated stock, and then boiled for 5 min.

The eluted proteins were diluted 10-fold with lysis buffer. A portion was removed, mixed (80:20) with SDS-PAGE sample buffer, and boiled for 5 min. The remaining sample was incubated with the second antiserum on ice for 60–90 min and with protein A-agarose at 8° C. for 1 hr. The immune complexes were washed three times with lysis buffer and boiled for 5 min in a mixture (80:20) of wash buffer and SDS-PAGE sample buffer.

Immunoprecipitation for Kinase Assays

Serum-deprived cells were incubated at 25° C. in the absence of presence of 30 ng/ml hGH for 60 min. The relatively long incubation period, low GH concentration, and low temperature were used to maximize the in vitro incorporation of $^{32}P$ into pp130 and GHR during the kinase assay. Cells were washed with phosphate-buffered saline, solubilized in 25 mM HEPES, 2 mM $Na_2CO_4$, 0.1% Triton X-100, 0.5 mM DTT, 1 mM phenylmethylsulfanyl fluoride, 10 μg/ml aprotinin, 10 μg/ml leupeptin (pH 7.4) (HVT), and centrifuged at 200,000×g for 1 hr at 4° C. Soluble proteins were incubated on ice for 1 hr with either αGH (1:10,000 dilution), αPY-Shafer (15 μg per plate of cells), or αJak2 (1:1,500 dilution) (Carter-Su., C. et al., *J. Biol. Chem.* 264:18654–18661 (1989)). Protein A-agarose was added for an additional 1 hr at 8° C. Immune complexes were washed three times with 50 mM HEPES, 150 mM NaCl, 0.1% Triton X-100, 0.5 mM DTT (pH 7.6) (NHT) and then once with 50 mM HEPES, 100 mM NaCl, 6.25 mM $MnCl_3$, 0.1% Triton X-100, 0.5 mM DTT (pH 7.6) (HNMT).

Sequential Immunoprecipitation With αPY and αJak2

Proteins immobilized on αPY-protein A-agarose complexes were transferred to a small plastic column and equilibrated for 5 min with 10 mM p-nitrophenyl phosphate, 20 μg/ml aprotinin, 20 μg/ml leupeptin in HNMT (eluting buffer). Phosphoproteins were then eluted with 180 μl of eluting buffer. αJak2 (1:200 dilution) was added, and the mixture was incubated on ice for 1 hr. Protein A-agarose and 0.7 ml of HNMT containing 20 μg/ml aprotinin, 20 μg/ml leupeptin (phosphorylation buffer) was added, and incubation continued at 6° C. for 1 hr. Immune complexes were washed three times with NHT and once with phosphorylation buffer.

In Vitro Kinase Assay and Phosphoamino Acid Analysis

Proteins immobilized on αJak2 or αGH were mixed with 95 μl of phosphorylation buffer. [$\gamma^{32}P$]ATP was then added to yield a final concentration of 10 μM ATP and 5 mM $MnCl_2$. After 10 min at 30° C., the reaction was stopped with the addition of 10 mM EDTA in NHT. The immune complexes were washed three times with NHT and once with phosphorylation buffer. $^{32}P$-labeled proteins were either subjected to a second immunoprecipitation or boiled for 5 min in SDS-PAGE sample buffer, resolved by SDS-PAGE, and visualized by autoradiography. The phosphoamino acid content of phosphorylated proteins was determined by limited acid hydrolysis using a modification of the procedure of Hunter and Selton (Hunter, T. and Selton, B. M., *Proc. Natl. Acad. Sci. USA* 77:1311–1315 (1980)) as described previously (Carter-Su., C. et al., *J. Biol. Chem.* 264:18654–18661 (1989); Stred, S. E., et al., *Endocrinol.* 127:2506–2516 (1990); Wang, X. et al., *J. Biol. Chem.* 267:17390–17396 (1992)).

SDS-PAGE and Densitometry

Proteins were separated by SDS-PAGE on 3%–10% gradient gels (30:0.05 acrylamide:bisacrylamide) as described previously (Carter-Su., C. et al., *J. Biol. Chem.* 264:18654–18661 (1989)). Densitometry was performed using a Bio-Med Instruments laser scanning densitometer attached to an Apple IIE computer (Bio-Med Instruments Videophoresis II data analysis computer program).

Example 4

Complementation of a Mutant Cell Line Defective in the Interferon-γ Signal Transduction Pathway by the Protein Tyrosine Kinase Jak2

Summary

The cell surface marker CD2 was placed under the control of the interferon-inducible 9–27 gene promoter and introduced into human HT1080 cells. A clone of cells showing a good response of CD2 to interferons-α, -β and -γ was selected and pools of mutagenized cells were screened for defective cell surface expression of CD2 and Class I HLAs in response to interferon-γ. Mutants in different complementation groups were isolated. Mutant γ-1 is deficient in the induction of all interferon-γ-inducible genes tested but retains a normal response to interferons-α and -β. Transfection of mutant γ-1 with protein tyrosine kinase Jak2 restored the wild-type phenotype. A role for Jak2 in the primary response to interferon-γ is indicated.

Introduction

The interferons (IFNs) confer an antiviral state on cells and can affect both cell growth and function (Pestka, S., et al., *Annu. Rev. Biochem.* 56:727–777 (1987)). There are three major antigenic types of human IFN: alpha (α), beta (β) and gamma (γ). Gene induction by IFNs-αβ and IFN-γ is through separate receptors. The existence of a minor IFN-β specific receptor cannot be excluded (Pellegrini, S., et al., *Mol. Cell. Biol.* 9:4605–4612 (1989)) and the multiplicity of IFN-α subtypes suggests that the interaction of these with the IFN-αβ receptor(s) is likely to be complex.

The isolation of mutants affecting both the IFN-αβ and the IFN-γ signal transduction pathways has indicated that common factors are involved (John, J., et al., *Mol. Cell. Biol.* 11:4189–4195 (1991); McKendry, R., et al., *Proc. Natl. Acad. Sci. USA* 88:11455–11459 (1991)). One such factor (p91, below and Example 4) has recently been identified (Schindler, C., et al., *Science* 258:1808–1812 (1992); Shuai, K., et al., *Science* 258:1808–1812 (1992)). IFN-binding components have been cloned for both major receptors (Aguet, M., et al., *Cell* 55:273–280 (1988); Uze, G., et al., *Cell* 60:225–234 (1990)). Signal transduction subunits have yet to be isolated, but the p48, p84, p91 and p113 polypeptide components of the primary transcription factor ISGF3, activated in response to IFNs-α and -β, have been cloned and characterized (Veals, S. A., et al., *Mol. Cell. Biol.* 12:3315–3324 (1992); Schindler, C., et al., *Proc. Natl. Acad. Sci. USA* 89:7836–7839 (1992); Schindler, C., et al., *Proc. Natl. Acad. Sci. USA* 89:7840–7843 (1992)). There is rapid phosphorylation on tyrosine of p91, p84 and p113 in response to IFN-α and of p91 and p84 in response to IFN-γ (Shuai, K., et al., *Science* 258:1808–1812 (1992)). In addition, complementation of mutant U1A (11.1) which was isolated from cells expressing a drug-selectable marker under the control of the predominantly IFN-αβ-responsive 6–16 gene promoter, has revealed a role for the protein tyrosine kinase Tyk2 in the IFN-αβ response pathway (Velazquez, L., et al., *Cell* 70:313–322 (1992)). Here, using an alternative selection technique, complementation of a mutant in the IFN-γ response by Jak2, another member of the same family of protein tyrosine kinases (Wilks, A. F., et al., *Mol. Cell. Biol.* 11:2057–2065 (1991); Harpur, A. G., et al., *Oncogene* 7:1347–1353 (1992); Firmbach-Kraft, I., et al., *Oncogene* 5:1329–1336 (1990); Example 1), is reported.

Results

The 9–27 gene promoter is inducible by IFN-γ as well as IFNs-α and -β (Reid, L. E., et al., *Proc. Natl. Acad. Sci. USA* 86:840–844 (1989)). Significant constitutive expression from this promoter precluded a drug selection protocol. Accordingly a clone of cells (2C4) expressing the simple cell-surface marker CD2 (normally expressed only on T-cells) under the control of the 9–27 promoter was derived and the fluorescence activated cell sorter (FACS) used to screen for loss or gain of IFN-γ inducibility. IFN-inducible expression of endogenous Class I and II HLAs was also monitored. In 2C4 cells good induction of all three antigens by IFN-γ and of CD2 and Class I by IFN-α was observed.

Mutant γ-1 was isolated by mutagenesis of 2C4 and several rounds of sorting. To enhance the isolation of trans rather than cis mutants and of mutants in the primary rather than secondary IFN-γ response pathways, the final two sorts were on both CD2 and Class I. Mutant γ-1 is defective in the response to IFN-γ but not to IFN-α or IFN-β. Transfection of this mutant with a murine Jak2 expression construction (Example 1), however, restored the IFN-γ response of all three cell surface markers in an enriched population and clones of transfectants. Transfection with murine Jak1, in the same construct, was without effect.

The expression of a spectrum of IFN-γ-inducible mRNAs was also monitored by RNase protection. For all eight IFN-inducible mRNAs tested the positive IFN-α response (minimal for IRF1 and GBP) was the same for 2C4, mutant γ-1 and the γ-1/Jak2 transfectants, whereas for IFN-γ the response observed in 2C4 was lost in γ-1 but restored in the γ-1/Jak2 transfectants. A gamma activation sequence (GAS) motif has recently been identified as mediating the primary IFN-γ response of the GBP and ITF1 genes through p91 (see Example 1; Decker, T., et al., *EMBO J.* 10:927–932 (1991); Kanno, Y., et al., *Mol. Cell. Biol.* 13:3951–3963 (1993)). The DNA elements and/or factors governing the primary IFN-γ response of the remainder of the genes tested have yet to be rigorously established. The fact, however, that all of the genes tested are affected is consistent with the defect in mutant γ-1 being in the primary IFN-γ response pathway.

In all cases the IFN-γ response was restored by Jak2 and the IFN-γ dose response curves for the wild-type 2C4 and γ-1/Jak2 transfectants were essentially identical: a clear response was seen at 10 IU/ml and an approaching maximal response at 100 IU/ml. No restoration of IFN-γ response was observed on transfection of γ-1 cells with a functional Tyk2 expression clone and, in an inverse experiment, Jak2 did not complement the defect in Tyk2 in a U1 mutant.

The defect in mutant γ-1 cells does not reflect the absence of Jak2 protein since levels comparable to wild-type were observed on western transfer as was the case for Jak1 and Tyk2. The anti-peptide antibody used to immunoprecipitate Jak2 and to probe the western transfer was designed to distinguish between Jak1 and Jak2 and has high specificity for Jak2 (see Examples 1–2). The mutation in γ-1 may, therefore, reflect point or other minor mutations affecting the function but not the production of Jak2. Alternatively, the mutation could be in an upstream component which, once mutated, fails to interact productively with normal levels of endogenous human Jak2, but is rescued by high levels (see Example 5) of the transfected murine Jak2.

It will require substantial additional work before one can be certain of the precise nature of the mutation involved. The defect in mutant γ-1 is, however, without any apparent major effect on the biding of IFN-γ to its receptor. Essentially identical binding was reproducibly observed with wild-type 2C4 and mutant γ-1 cells. This is in contrast to the situation with mutant U1A (originally coded 11.1) in which the defect in Tyk2 results in loss of high affinity receptor binding for IFN-α (Pellegrini, S., et al., *Mol. Cell. Biol.* 9:4605–4612 (1989)). It will be of interest to determine whether this difference reflects the absence of Tyk2 but not Jak2 protein in U1A and γ-1 respectively, or a more fundamental difference in the presumptive interaction of the two kinases with their respective receptor complexes. The Jak2 protein, like Tyk2, does not appear to be significantly induced in response to IFNs γ or -α in the wild-type cells.

Discussion

Here it is shown that a mutant human cell line, defective in the IFN-γ response of all genes tested, is complemented by murine Jak2.Example 5 shows: (1) direct evidence that the defect in mutant γ-1 is early in the primary response pathway; (2) that Jak2 is rapidly phosphorylated on tyrosine in response to IFN-γ; and (3) results consistent with the rapid activation and (auto)phosphorylation of Jak2 in response to IFN-γ in wild-type but not mutant cells.

Irrespective of the precise nature of the mutation in γ-1, these data indicate an essential role for Jak2 in the primary IFN-γ response. The availability of antibody to Jak2 and of mutants in additional complementation groups in the IFN-γ response pathway should prove invaluable in determining the number and nature of the components involved in this response.

Methods and Materials

Cell surface expression of transfected CD2 and endogenous Class I and II HLAs in response to IFNs-α or -γ on wild-type 2C4, mutant γ-1 cells and mutant γ-1 cells stably transfected with a murine Jak2 cDNA expression construct. Data was generated for an enriched population and a clone of γ-1/Jak2 transfectants using FACSCAN (Becton Dickinson) analyses (3000 data points, Consort 30). Cells were plated at $5 \times 10^5/10$ cm dish and treated the following day with $10^3$ IU/ml of a highly purified mixture of α-IFNs (Wellferon $1.5 \times 10^8$ IU/mg protein, kindly supplied by Wellcome Research Laboratories, Beckenham, UK) or recombinant human IFM-γ ($4 \times 10^7$ IU/mg protein, a generous gift from Dr. Gunter Adolf, Ernst Boehringer Institut fur Arzneimittelforschung, Vienna, Austria).

Cells ($10^6$) were stained for 30 min at 0° C. with R-phycoerythrin-conjugated murine monoclonal antibody to human CD2 (Dako-CD2 MT910, DAKO A/S Denmark) or HLA DRA (clone L243, Becton Dickinson), or FITC-conjugated murine monoclonal antibody to human HLA ABC (shared determinant, clone W6/32, Seralab, UK) and fixed in 1% paraformaldehyde. Clone 2C4 was derived by stable co-transfection of human HT1080 cells with pDW9-27CD2 and pTKNco and FACSCAN analysis of G418-resistant clones. pDW9-27D2 is a modification of PJ3omega (Morgaenstern, J. P. et al., *Nucl. Acids Res.* 18:1068 (1990)) in which the SV40 promoter was replaced by the 1.8 kb HindIII to BspMII promoter fragment of the 9–27 gene (Reid, L. E., et al., *Proc. Natl. Acad. Sci. USA* 86:840–844 (1989)) and which carries a full length CD2 cDNA (Sewel, W. A., et al., *Proc. Natl. Acad. Sci. USA* 83:8718–8722 (1986)) in the EcoRI site of the polylinker.

Mutagenesis (five rounds) with ICR191 was as previously described (McKendry, R., et al., *Proc. Natl. Acad. Sci. USA* 88:11455–11459 (1991)). Cells not responsive to IFN-γ were "selected" using a FACSTAR Plus cell sorter (Becton Dickinson). $5 \times 10^7$ mutagenized cells were treated with 500 IU/ml of recombinant human IFN-γ for 48 h, resuspended and stained with phycoerythrin-conjugated antibody to CD2 and (in the last two sorts) FITC-conjugated antibody to HLA Class I (above) and sorted immediately. The bottom 5% of fluorescing cells were collected.

After six rounds of sorting clone γ-1 was isolated by limiting dilution of the enriched population. It showed a novel IFN-γ$^-$ -α$^+$-β$^+$ phenotype distinct from other IFN-γ mutants previously described (Loh, J. E., et al., *EMBO J.* 11:1351–1363 (1992); Mao, C., et al., *Proc. Natl. Acad. Sci. USA* 90:2880–2884 (1993)). The phenotype was stable on continuous culture for at least three months.

Mutant γ-1 was complemented by transfection with a full length cDNA of murine Jak2 downstream of the CMV promoter in pRK5 in the presence of a puromycin-selectable marker plasmid. The puromycin-resistant population of stable transfectants were treated with recombinant IFN-γ, FACS sorted and the top 7% of responder cells were collected and analyzed. Clones of γ-1/Jak2 transfected cells, obtained by limiting dilution of the enriched population, were also analyzed, for which full restoration of the IFN-γ response was observed.

IFN-inducible gene expression in wild type 2C4, mutant γ-1 and mutant γ-1/Jak2 transfected cells: mRNA expression in response to IFNs-α or -γ was monitored by RNase protection using probes to detect the IFN-inducible mRNAs of: the 9–27, 6–16, 2–5A synthetase and ISGF3γ genes and the p91 and p84 alternatively spliced products of the p91/84 ISGF3α gene and the IRF1 and GBP genes. The protection of γ-actin mRNA served as an internal loading control. Cytoplasmic RNA was prepared from monolayer cells by NP40 lysis and phenol/chloroform extraction (Porter, A. C. G., et al., *EMBO J.* 7:85–92 (1988)). RNase protection was with RNA probes labeled with $^{32}$P UTP to $2-5 \times 10^8$ cpm/µg of input DNA (Melton, D. A., et al., *Nucl. Acids Res.* 12:7035–7056 (1984)). One to $3 \times 10^5$ cpm of each probe and 10 µg of RNA were used in each assay.

Expression of Jak2 in wild-type 2C4, mutant γ-1 cells and mutant γ-1 cells transfected with murine Jak2 (γ-1Jak2tr): Jak2 protein was immunoprecipitated from precleared whole cell extracts ($10^7$ cells) with antiserum to Jak2 (Example 1) and protein A Sepharose (Pharmacia; John, J., et al., *Mol. Cell. Biol.* 11:4189–4195 (1991)) and analyzed by SDS-PAGE and western transfer using the antibody to Jak2 and the ECL detection system (Amersham International, UK). For the mutant γ-1 cell extracts immunoprecipitation was carried out in the absence (no pept) or presence (30 ug/ml) of the Jak2 peptide to which the antiserum was raised (Jak2 pept) or, as a non-specific control, an unrelated Jak1 peptide (Jak1).

Binding of $^{125}$I-labeled IFN-γ to 2C4 and mutant γ-1 cells: $^{125}$I-IFN-γ (667 Ci/mMole, Amersham International, UK) treatment was of triplicate samples of $10^6$ cells for 90 min at 0° C. Non-specific binding was subtracted. It was determined in parallel in the presence of a 200 fold excess of unlabeled IFN-γ and represented approximately 40% of the total radioactivity bound. In a parallel antiviral assay versus EMC virus 1 fmole of $^{125}$I-IFN-γ was equivalent to 0.15 IU. Specific binding at the highest IFN-γ concentration here corresponded to about 6000 receptors per cell. On dilution of the IFN to a lower specific activity saturation binding was observed at approximately 10,000 receptors per cell.

Example 5

Activation of the Protein Tyrosine Kinase Jak2 in Response to Interferon-γ

Summary

Mutant γ-1 cells respond normally to interferons-α and -β but are defective in the response of all genes tested to interferon -γ. The mutants can be complemented by the protein tyrosine kinase Jak2 (Example 4). In wild-type cells the transcription factor p91, which plays a central role in the primary interferon-γ signal transduction pathway, is rapidly phosphorylated on tyrosine in response to interferon-γ. No such phosphorylation occurs in mutant γ-1 cells, but it is restored on complementation of γ-1 cells with Jak2.

Moreover, Jak2 is itself rapidly phosphorylated on tyrosine in response to interferon-γ in wild-type cells. Interferon-γ dependent phosphorylation of Jak2 is also observed in in vitro kinase assays of immunoprecipitates from human and mouse cells. No such phosphorylation is seen in mutant γ-1 cells or in response to interferon-α. These results indicate a role for Jak2 early in the primary interferon-γ signal transduction pathway.

Results

Interferons (IFNs) -α, -β and -γ induce overlapping sets of genes through distinct receptors (Pestka et al., Ann. Rev. Biochem. 56:727-777 (1987)). There has been rapid recent progress in the understanding of the signal transduction pathways involved. Central to this has been the realization that p91, a component of the complex IFN-αβ-inducible transcription factor ISGF3, plays a dual role in the IFN-αβ and -γ response pathways.

p91 is rapidly phosphorylated on tyrosine in response to either type of IFN (Schindler et al., Science 257:809-813 (1992); Shuai et al., Science 258:1808-1812 (1992)). Consistent with this, p91 is required for the IFN-γ response of a wide spectrum of genes. It appears to correspond to the gamma activation factor (GAF) which was first identified as being necessary for the activation of transcription of the GBP gene (Decker et al., EMBO J. 10:927-932 (1991)) and has since been implicated in the activation of a number of additional genes in response to IFN-γ through a common DNA motif (Shuai et al., Science 258:1808-1812 (1992); Pearse et al., Proc. Natl. Acad. Sci. USA 90:4314-4318 (1993); Kanno et al., Mol. Cell. Biol. 13:3951 (1993)). Mutant γ-1 was, therefore, assayed for phosphorylation of p91. Phosphorylation of p91, monitored by incorporation of $^{32}P_i$, occurs rapidly in wild-type 2C4 cells. No such phosphorylation was observed in mutant γ-1.

Phosphorylation of p91 did occur in γ-1 cells complemented by Jak2 as monitored by incorporation of $^{32}P_i$ or with antibodies to phosphotyrosine. Normal levels of p91 were present and, interestingly, phosphorylation of the p91 and p113 components of ISGF3α by IFN-α was normal in the mutant cells (Phosphorylation of the p84 component of ISGF3α in response to IFNs -α or γ is always lower and frequently difficult to detect (Schindler et al., Science 257:809-813 (1992); Shuai et al., Science 258:1808-1812 (1992)).

In addition, γ-1 cells are not complementable by a functional p91 expression construct. The defect in γ-1 cells is, therefore, upstream of p91.

Tyrosine phosphorylation of Jak2 was monitored by immunoprecipitation with specific antibody followed by western transfer analysis of the immune precipitates with antibody to phosphotyrosine. On this basis, Jak2 is rapidly phosphorylated on tyrosine in response to IFN-γ in wild-type but not in mutant γ-1 cells. No such phosphorylation of Jak2 was observed in response to IFN-α under conditions identical to those under which phosphorylation of Tyk2 by IFN-α is readily detected.

Tyrosine phosphorylation of p91 in response to IFN-α and of p91 and p113 in response to IFN-α were monitored in parallel as internal controls both for IFN activity and detection of phosphotyrosine using a mixture of Py-20 and 4G10 antiphosphotyrosine antibodies. On reprobing the same transfer with antibody to Jak2, comparable levels of Jak2 protein were detected in wild-type and γ-1 mutant cells. The defect in γ-1 is, therefore, in the phosphorylation/function rather than the production of Jak2 (see Example 4).

A priori the apparent phosphorylation of Jak2 could be of an immunologically cross-reacting protein. The antiserum used, however, was raised against a Jak2 peptide which is not conserved in Jak1 and has high specificity for Jak2 (see Examples 1 and 2). Consistent with this, phosphorylated protein was not recovered when the immune precipitation was carried out in the presence of the appropriate competing peptide.

In γ-1/Jak2 transfectants there is a high "background" level of tyrosine phosphorylation of the overexpressed exogenous murine Jak2 even in the absence of IFN-γ treatment. The basis for this is not known. Against this background a variable increase in total tyrosine phosphorylation of Jak2 is seen in response to IFN-γ in the complemented cells. Interestingly, however, even in experiments in which no obvious increase in Jak2 phosphorylation was observed in the γ-1/Jak2 transfectants when assayed, a substantial response to IFN-γ was consistently observed in parallel in vitro kinase assays (see below). Transfected Jak2 can, therefore, be phosphorylated in response to IFN-γ. It is reasonable to conclude that the phosphorylation observed in wild-type cells in response to IFN-γ is due to Jak2.

Activation of protein tyrosine kinases in response to growth factors classically results in kinase activity which can be detected in an immune precipitate of the activated enzyme. Jak2, activated in response to IL3 (Example 1) and erythropoietin (Example 2), shows similar apparent in vitro kinase activity. This is also the case for Jak2 in response to IFN-γ. IFN-γ-dependent kinase activity was observed upon assay of Jak2 immunoprecipitates from wild-type 2C4 or mutant γ-1/Jak2 transfected cells. No such activity was observed in response to IFN-α or when the immunoprecipitates were prepared from mutant γ-1 cells or from wild-type cells in the presence of competing Jak2 peptide. Phosphorylation of Jak2 is not restricted to human HT1080 derived cells, and is also seen in response to IFN-γ but not -α in other human and a variety of mouse cell lines, including mouse L-cells.

Discussion

The results presented here together with those in Example 4 indicate that Jak2 is activated in response to IFN-α and such activation plays a role early in the primary IFN-γ response pathway. Granted that p91 is phosphorylated at the same site (Tyr 701) in response to IFN-α and γ (Schindler et al., Science 257:809-813 (1992); Shuai et al., Science 258:1808-1812 (1992)), the normal phosphorylation of p91 in the γ-1 mutant in response to IFN-α is of interest in this regard. One can conclude either that Tyk2 or Jak2 can each carry out phosphorylation of the same tyrosine or, more intriguingly, that there is an additional kinase(s) involved.

Turning to the activation of Jak2, in the case of erythropoietin this appears to occur through direct interaction of Jak2 with the erythropoietin receptor (Example 2). It will obviously be of considerable interest if there is a similar interaction in the case of the IFN-γ pathway. The common activation of Jak2 by erythropoietin, IL3 and a number of other cytokines (see Examples 1-3) raises obvious questions. A major thrust of future work will be to identify the nature of the proteins interacting with Jak2 and the factors determining the specificity of the response.

Methods and Materials

Tyrosine phosphorylation of p91 in response to IFN-γ in normal and mutant γ-1 cells: Phosphorylation of p91 in response to IFN-γ in wild-type (2C4), mutant γ-1 and mutant γ-1 cells transfected with Jak2 (γ-Jak2tr) was monitored by incorporation of $^{32}P94_i$ or by western transfer with antibody to phosphotyrosine. p91 protein levels were monitored by western transfer as was tyrosine phosphorylation of the p91 and p113 components of ISGF3 in response to INF-α at $10^3$ IU/ml for 15–30 minutes. p91 was immunoprecipitated from precleaned whole cell extracts ($10^7$ cells) with antiserum to p91 and protein A Sepharose (Pharmacia) as described previously (Schindler et al., *Science* 257:809–813 (1992); Shuai et al., *Science* 258:1808–1812 (1992)) and analyzed by SDS-PAGE and western transfer using a mixture of PY20 (ICN) and 4G10 (UBI) antiphosphotyrosine antibodies and, after stripping in 0.1M TrisHI pH 8.0, antibody to p91.p91 and p113 (complexed in IFN-α-activated ISGFα) were co-immunoprecipitated with antibody to p113 (Schindler et al., *Science* 257:809–813 (1992)) and analyzed by SDS-PAGE and western transfer with antiphosphotyrosine antibodies as above. In the western transfers detection was by ECL (Amersham, UK) except for the p91 antibody screened transfer which was stained with diaminobenzidine (Amersham UK).

Tyrosine phosphorylation of Jak2 in response to IFN-γ but not -α in wild-type 2C4, mutant γ-1 and mutant γ-1/Jak2 transfected cells: Phosphorylation of Jak2, and of p91 and p113 as controls, were monitored by immunoprecipitation, SDS-PAGE and western transfer for phosphotyrosine using a mixture of Py-20 and 4G10 antiphosphotyrosine antibodies and detection by ECL (Amersham International). Extracts from INF-γ treated cells were immunoprecipitated with a mixture of antibodies to Jak2 and p113 (the latter co-precipitates 091 in IFN-α-activated ISGF3). The same blot was stripped (as described above) and reprobed with antibody to Jak2.Extracts from cells treated with INF-γ for 15 min were immunoprecipitated with antibody to Jak2 in the presence or absence, as indicated, of 0.1 mg/ml of the Jak2 peptide against which the antibody to Jak2 was raised (Example 1) or an unrelated Jak1 peptide. The immunoprecipitates were analyzed by SDS-PAGE and western transfer using antibodies to phosphotyrosine as above. Growth of the cells and treatment with $10^3$ IU/ml of highly purified IFN-γ or -α was as described above.

In vitro kinase assays: IFN-dependent phosphorylation of Jak2 was assayed in immunoprecipitates from (A) wild type (2C4) and mutant γ-1/Jak2 transfected cells, (B) wild type (2C4) and mutant γ-1 cells and (C) mouse L-cells. Treatment with IFN-γ or -α (500 IU/ml) as indicated was for 15 min. Immune precipitates on protein A Sepharose (Parmacia) were washed in 50 mM NaCl, 5 mM MgCl$_2$, 5 mM MnCl$_2$, 0.1 mM Na$_3$VO$_4$, 10 mM HEPES pH 7.4 and incubated in the same buffer containing 0.25 mCi/ml of $^{32}$P-γ-ATP for 30 min at room temperature (see Examples 1–2). After extensive washing proteins were eluted in sample buffer and analyzed by SDS-PAGE. Detection was by autoradiography or by western transfer for phosphotyrosine as described above. Growth and IFN treatment of human cells was as described above. Growth and IFN treatment of mouse L-cells was similar, but with recombinant murine IFN-γ (1–2×$10^7$ IU/mg protein, a generous gift from Dr. Gunter Adolf, Ernest Boehringer Institut fur Arzneimittelforschung, Vienna, Austria) or recombinant human IFN-α A/D (Bgl), a hybrid highly active on mouse cells (2×$10^8$ IU/mg protein kindly supplied by Dr. Sidney Pestka, Robert Wood Johnson Medical School, N.J., USA).

Example 6

An Inhibitor of Epo Activity (Genestein) Inhibits Jak2 Kinase Activity

The biochemical activity of Jak2 may be demonstrated by use of an in vitro kinase assay. In this assay, purified Jak2 is precipitated from cell lysates using Jak2-specific antisera bound to protein A-sepharose. The immunoprecipitated Jak2 is then washed with kinase buffer (50 mM NaCl, 5 mM MgCl$_2$, 5 mM MnCl$_2$, 0.1 mM Na$_3$VO$_4$, 10 mM HEPES pH 7.4) and subsequently incubated for 30 minutes at room temperature with an equal volume of kinase buffer containing 0.25 mCi/ml $^{32}$P-gamma-ATP. After extensive washing, proteins are eluted with sample buffer for SDS-PAGE and separated on 7% gels. $^{32}$P-containing proteins are then visualized by autoradiography.

Using this assay system, active Jak2 kinase has been demonstrated to be present only in mammalian cells which have been treated with an appropriate cytokine, such as erythropoietin (Epo) or interleukin-3 (IL-3). Thus, activation of the Jak2 catalytic activity is correlated with the biological activities of these cytokines.

This correlation is further supported by studies using the tyrosine kinase-specific inhibitor known as genestein. Genestein is known to inhibit the ability of Epo to stimulate cell growth.

Inclusion of genestein at 0.1 mM in the in vitro kinase assay described above results in a 2-fold reduction in the tyrosine kinase activity of Jak2. Thus, the inhibitory effect of genestein on Epo-induced cell proliferation can be explained by its inhibition of Jak2.

Example 7

Production of a Constitutively Active Jak2 Kinase From Insect Cells

Since the active form of Jak2 may be isolated from mammalian cells only after stimulation with an appropriate cytokine, we have developed a system for the expression of catalytically active Jak2 which does not require cytokine stimulation. Specifically, when expressed at high levels in insect cells Jak2 is constitutively in an active state. This expression was accomplished by insertion of the Jak2 cDNA between the NotI and SmaI sites of the baculovirus transfer vector pVL1392 (PharMingen, San Diego Calif.). This Jak2/vector construct then was cotransfected into insect cells with a defective baculovirus DNA (BaculoGold DNA, PharMingen, San Diego, Calif.).

Recombination events between the defective baculovirus DNA and the Jak2/vector DNA results in DNA encoding a viable baculovirus which will constitutively express Jak2.Infection of insect cells with this recombinant baculovirus results in the high level expression of active Jak2 which may be purified by immunoprecipitation with Jak2-specific antisera. This source of active Jak2 will be useful in the study of biochemical properties of this enzyme, and can also be used in assays for inhibitors of Jak2 kinase activity based upon the in vitro Jak kinase assay described herein.

While the invention has been described in connection with specific embodiments thereof, this application is intended to cover any variations, uses, or adaptions of the invention following the general principles of the invention and including such departures from the present disclosure as come within the known or customary practice within the art to which the invention pertains and as may be applied to the essential features set forth herein and as follows the scope of the appended claims.

What is claimed is:

1. An assay for identifying a composition capable of regulating the biological response of a eukaryotic cell to a cytokine whose activity on said cell is mediated by tyrosine phosphorylation by at least one Jak kinase, wherein said Jak kinase is selected from the group consisting of Jak1, Jak2 and Tyk2, said assay comprising (a) contacting said cytokine, other than erythropoietin (EPO) or interleukin-3 (IL-3), with a eukaryotic cell having said Jak kinase under conditions allowing said cell to undergo cytokine-induced activation;

(b) contacting said composition with said eukaryotic cell before or during cytokine induction;

(c) detecting changes, due to said composition, resulting from tyrosine phosphorylation by said Jak kinase that regulates said biological response in said cell, wherein said response is induced by binding of said cytokine to a cytokine receptor on said cell; and (d) identifying whether said composition is an inhibitor which blocks or significantly reduces, or an enhancer which increases, the in vitro kinase activity detected in the Jak kinase when extracts are prepared from the cells following cytokine-induced activation.

2. An assay according to claim 1, wherein said cytokine binds to a member of the cytokine receptor superfamily.

3. An assay according to claim 1, wherein said detecting is selected from (i) measuring tyrosine phosphorylation activity of a Jak kinase in said cell following cytokine-induced activation; or (ii) determining the state of tyrosine phosphorylation of a Jak kinase in said cell following cytokine-induced activation.

4. An assay according to claim 1 wherein said detecting step comprises (a) preparing a first extract from a first population of said eukaryotic cell after cytokine-induced activation, said extract comprising said Jak kinase and a substrate for said Jak kinase;

(b) preparing a second extract from a second population of said eukaryotic cell after cytokine-induced activation, said extract comprising said Jak kinase and a substrate for said Jak kinase, wherein said composition is provided to said second population before or during said activation;

(c) preparing a first reaction mixture comprising said first extract combined with adenosine triphosphate (ATP) with a delectably labeled phosphorus at the γ position in a kinase buffer;

(d) preparing a second reaction mixture comprising said second extract combined with adenosine triphosphate (ATP) with a detectably labeled phosphorus at the γ position in a kinase buffer; and (e) detecting said substrate containing said detectably labeled phosphorus in said first and said second reaction mixture;

wherein said composition is identified as capable of regulating the biological response of a eukaryotic cell to a cytokine whose activity is mediated by tyrosine phosphorylation of said Jak kinase, if said second reaction mixture contains significantly different amounts of said substrate containing said detectably labeled phosphorus from said first reaction mixture.

* * * * *

UNITED STATES PATENT AND TRADEMARK OFFICE
CERTIFICATE OF CORRECTION

PATENT NO. : 5,728,536

DATED : March 17, 1998

INVENTORS : Ihle *et al.*

It is certified that an error appears in the above-identified patent and that said Letters Patent is hereby corrected as shown below.

On the title page, item [22] ("Filed"), after "Jul. 29," please delete "1994" and insert therein --1993--.

Signed and Sealed this

Eleventh Day of May, 1999

Attest:

Q. TODD DICKINSON

*Attesting Officer*  *Acting Commissioner of Patents and Trademarks*

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
      ( A ) LENGTH: 5 amino acids
      ( B ) TYPE: amino acid
      ( D ) TOPOLOGY: linear ( x i ) SEQUENCE DESCRIPTION: SEQ ID NO:1:

```
Trp Ser Xaa Trp Ser
1               5
```

( 2 ) INFORMATION FOR SEQ ID NO:2:

( i ) SEQUENCE CHARACTERISTICS:
      ( A ) LENGTH: 15 amino acids
      ( B ) TYPE: amino acid
      ( D ) TOPOLOGY: linear ( x i ) SEQUENCE DESCRIPTION: SEQ ID NO:2:

```
Val Leu Pro Gln Asp Lys Glu Tyr Tyr Lys Val Lys Glu Pro Gly
1               5                   10                  15
```

( 2 ) INFORMATION FOR SEQ ID NO:3:

( i ) SEQUENCE CHARACTERISTICS:
      ( A ) LENGTH: 15 amino acids
      ( B ) TYPE: amino acid
      ( D ) TOPOLOGY: linear ( x i ) SEQUENCE DESCRIPTION: SEQ ID NO:3:

```
Ala Ile Glu Thr Asp Lys Glu Tyr Tyr Thr Val Lys Asp Asp Arg
1               5                   10                  15
```

( 2 ) INFORMATION FOR SEQ ID NO:4:

( i ) SEQUENCE CHARACTERISTICS:
      ( A ) LENGTH: 15 amino acids
      ( B ) TYPE: amino acid
      ( D ) TOPOLOGY: linear ( x i ) SEQUENCE DESCRIPTION: SEQ ID NO:4:

```
Ala Val Pro Glu Gly His Glu Tyr Tyr Arg Val Arg Glu Asp Gly
1               5                   10                  15
```

( 2 ) INFORMATION FOR SEQ ID NO:5:

( i ) SEQUENCE CHARACTERISTICS:
      ( A ) LENGTH: 19 amino acids
      ( B ) TYPE: amino acid
      ( D ) TOPOLOGY: linear ( x i ) SEQUENCE DESCRIPTION: SEQ ID NO:5:

```
Asp Ser Gln Arg Lys Leu Gln Phe Tyr Glu Asp Lys His Gln Leu Pro
1               5                   10                  15

Ala Pro Lys
```

( 2 ) INFORMATION FOR SEQ ID NO:6:

( i ) SEQUENCE CHARACTERISTICS:
      ( A ) LENGTH: 19 amino acids
      ( B ) TYPE: amino acid ( D ) TOPOLOGY: linear ( x i ) SEQUENCE DESCRIPTION: SEQ ID NO:6:

| Thr | Leu | Ile | Glu | Lys | Glu | Arg | Phe | Tyr | Glu | Ser | Arg | Cys | Arg | Pro | Val |
|---|---|---|---|---|---|---|---|---|---|---|---|---|---|---|---|
| 1 |  |  |  | 5 |  |  |  |  | 10 |  |  |  |  | 15 |  |

Thr Pro Ser ( 2 ) INFORMATION FOR SEQ ID NO:7:

( i ) SEQUENCE CHARACTERISTICS:
        ( A ) LENGTH: 19 amino acids
        ( B ) TYPE: amino acid
        ( D ) TOPOLOGY: linear ( x i ) SEQUENCE DESCRIPTION: SEQ ID NO:7:

| Ser | Pro | Ser | Glu | Lys | Glu | His | Phe | Tyr | Gln | Arg | Gln | His | Arg | Leu | Pro |
|---|---|---|---|---|---|---|---|---|---|---|---|---|---|---|---|
| 1 |  |  |  | 5 |  |  |  |  | 10 |  |  |  |  | 15 |  |

Glu Pro Ser ( 2 ) INFORMATION FOR SEQ ID NO:8:

( i ) SEQUENCE CHARACTERISTICS:
        ( A ) LENGTH: 3629 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 94..3480

( x i ) SEQUENCE DESCRIPTION: SEQ ID NO:8:

```
CGGGGGAACA AGATGTGAAC TGTTTTCCCT CCCCAGAAGA GAGGCCCTT  TTTTTCCCTC        60

CCGCGAAGGC CAATGTTCTG AAAAAAGCTC TAG ATG GGA ATG GCC TGC CTT ACA        114
                                    Met Gly Met Ala Cys Leu Thr
                                     1               5

ATG ACA GAA ATG GAG GCA ACC TCC ACA TCT CCT GTA CAT CAG AAT GGT         162
Met Thr Glu Met Glu Ala Thr Ser Thr Ser Pro Val His Gln Asn Gly
        10              15                  20

GAT ATT CCT GGA AGT GCT AAT TCT GTG AAG CAG ATA GAG CCA GTC CTT         210
Asp Ile Pro Gly Ser Ala Asn Ser Val Lys Gln Ile Glu Pro Val Leu
        25              30                  35

CAA GTG TAT CTG TAC CAT TCT CTT GGG CAA GCT GAA GGA GAG TAT CTG         258
Gln Val Tyr Leu Tyr His Ser Leu Gly Gln Ala Glu Gly Glu Tyr Leu
 40              45                  50                      55

AAG TTT CCA AGT GGA GAG TAT GTT GCA GAA GAA ATT TGT GTG GCT GCT         306
Lys Phe Pro Ser Gly Glu Tyr Val Ala Glu Glu Ile Cys Val Ala Ala
                 60                  65                  70

TCT AAA GCT TGT GGT ATT ACG CCT GTG TAT CAT AAT ATG TTT GCG TTA         354
Ser Lys Ala Cys Gly Ile Thr Pro Val Tyr His Asn Met Phe Ala Leu
             75                  80                  85

ATG AGT GAA ACC GAA AGG ATC TGG TAC CCA CCC AAT CAT GTC TTC CAC         402
Met Ser Glu Thr Glu Arg Ile Trp Tyr Pro Pro Asn His Val Phe His
         90                  95                  100

ATA GAC GAG TCA ACC AGG CAT GAC ATA CTC TAC AGG ATA AGG TTC TAC         450
Ile Asp Glu Ser Thr Arg His Asp Ile Leu Tyr Arg Ile Arg Phe Tyr
     105                 110                 115

TTC CCT CAT TGG TAC TGT AGT GGC AGC AGC AGA ACC TAC AGA TAC GGA         498
Phe Pro His Trp Tyr Cys Ser Gly Ser Ser Arg Thr Tyr Arg Tyr Gly
120             125                 130                     135

GTG TCC CGT GGG GCT GAA GCT CCT CTG CTT GAT GAC TTT GTC ATG TCT         546
Val Ser Arg Gly Ala Glu Ala Pro Leu Leu Asp Asp Phe Val Met Ser
                140                 145                 150
```

```
TAC CTT TTT GCT CAG TGG CGG CAT GAT TTT GTT CAC GGA TGG ATA AAA    594
Tyr Leu Phe Ala Gln Trp Arg His Asp Phe Val His Gly Trp Ile Lys
            155                 160                 165

GTA CCT GTG ACT CAT GAA ACT CAG GAA GAG TGT CTT GGG ATG GCG GTG    642
Val Pro Val Thr His Glu Thr Gln Glu Glu Cys Leu Gly Met Ala Val
            170                 175                 180

TTA GAC ATG ATG AGA ATA GCT AAG GAG AAA GAC CAG ACT CCA CTG GCT    690
Leu Asp Met Met Arg Ile Ala Lys Glu Lys Asp Gln Thr Pro Leu Ala
    185                 190                 195

GTC TAT AAC TCT GTC AGC TAC AAG ACA TTC TTA CCA AAG TGC GTT CGA    738
Val Tyr Asn Ser Val Ser Tyr Lys Thr Phe Leu Pro Lys Cys Val Arg
200                 205                 210                 215

GCG AAG ATC CAA GAC TAT CAC ATT TTA ACC CGG AAG CGA ATC AGG TAC    786
Ala Lys Ile Gln Asp Tyr His Ile Leu Thr Arg Lys Arg Ile Arg Tyr
                220                 225                 230

AGA TTT CGC AGA TTC ATT CAG CAA TTC AGT CAA TGT AAA GCC ACT GCC    834
Arg Phe Arg Arg Phe Ile Gln Gln Phe Ser Gln Cys Lys Ala Thr Ala
            235                 240                 245

AGG AAC CTA AAA CTT AAG TAT CTT ATA AAC CTG GAA ACC CTG CAG TCT    882
Arg Asn Leu Lys Leu Lys Tyr Leu Ile Asn Leu Glu Thr Leu Gln Ser
            250                 255                 260

GCC TTC TAC ACA GAA CAG TTT GAA GTA AAA GAA TCT GCA AGA GGT CCT    930
Ala Phe Tyr Thr Glu Gln Phe Glu Val Lys Glu Ser Ala Arg Gly Pro
    265                 270                 275

TCA GGT GAG GAG ATT TTT GCA ACC ATT ATA ATA ACT GGA AAC GGT GGA    978
Ser Gly Glu Glu Ile Phe Ala Thr Ile Ile Ile Thr Gly Asn Gly Gly
280                 285                 290                 295

ATT CAG TGG TCA AGA GGG AAA CAT AAG GAA AGT GAG ACA CTG ACA GAA    1026
Ile Gln Trp Ser Arg Gly Lys His Lys Glu Ser Glu Thr Leu Thr Glu
                300                 305                 310

CAG GAC GTA CAG TTA TAT TGT GAT TTC CCT GAT ATT ATT GAT GTC AGT    1074
Gln Asp Val Gln Leu Tyr Cys Asp Phe Pro Asp Ile Ile Asp Val Ser
            315                 320                 325

ATT AAG CAA GCA AAC CAG GAA TGC TCA AAT GAA AGT AGA ATT GTA ACT    1122
Ile Lys Gln Ala Asn Gln Glu Cys Ser Asn Glu Ser Arg Ile Val Thr
            330                 335                 340

GTC CAT AAA CAA GAT GGT AAA GTT TTG GAG ATA GAA CTT AGC TCA TTA    1170
Val His Lys Gln Asp Gly Lys Val Leu Glu Ile Glu Leu Ser Ser Leu
    345                 350                 355

AAA GAA GCC TTG TCA TTC GTG TCA TTA ATT GAC GGG TAT TAC AGA CTA    1218
Lys Glu Ala Leu Ser Phe Val Ser Leu Ile Asp Gly Tyr Tyr Arg Leu
360                 365                 370                 375

ACT GCG GAT GCG CAC CAT TAC CTC TGC AAA GAG GTG GCT CCC CCA GCT    1266
Thr Ala Asp Ala His His Tyr Leu Cys Lys Glu Val Ala Pro Pro Ala
                380                 385                 390

GTG CTC GAG AAC ATA CAC AGC AAC TGC CAC GGC CCA ATA TCA ATG GAT    1314
Val Leu Glu Asn Ile His Ser Asn Cys His Gly Pro Ile Ser Met Asp
            395                 400                 405

TTT GCC ATT AGC AAA CTA AAG AAG GCG GGT AAC CAG ACT GGA CTA TAT    1362
Phe Ala Ile Ser Lys Leu Lys Lys Ala Gly Asn Gln Thr Gly Leu Tyr
            410                 415                 420

GTG CTA CGA TGC AGC CCT AAG GAC TTC AAC AAA TAC TTT CTG ACC TTT    1410
Val Leu Arg Cys Ser Pro Lys Asp Phe Asn Lys Tyr Phe Leu Thr Phe
    425                 430                 435

GCT GTT GAG CGA GAA AAT GTC ATT GAA TAT AAA CAC TGT TTG ATT ACG    1458
Ala Val Glu Arg Glu Asn Val Ile Glu Tyr Lys His Cys Leu Ile Thr
440                 445                 450                 455

AAG AAT GAG AAT GGA GAA TAC AAC CTC AGC GGG ACT AAG AGG AAC TTC    1506
Lys Asn Glu Asn Gly Glu Tyr Asn Leu Ser Gly Thr Lys Arg Asn Phe
                460                 465                 470
```

```
AGT  AAC  CTT  AAG  GAC  CTT  TTG  AAT  TGC  TAC  CAG  ATG  GAA  ACT  GTG  CGC        1554
Ser  Asn  Leu  Lys  Asp  Leu  Leu  Asn  Cys  Tyr  Gln  Met  Glu  Thr  Val  Arg
               475                      480                       485

TCA  GAC  AGT  ATC  ATC  TTC  CAG  TTT  ACC  AAA  TGC  TGC  CCC  CCA  AAG  CCA        1602
Ser  Asp  Ser  Ile  Ile  Phe  Gln  Phe  Thr  Lys  Cys  Cys  Pro  Pro  Lys  Pro
               490                      495                       500

AAA  GAT  AAA  TCA  AAC  CTT  CTC  GTC  TTC  AGA  ACA  AAT  GGT  ATT  TCT  GAT        1650
Lys  Asp  Lys  Ser  Asn  Leu  Leu  Val  Phe  Arg  Thr  Asn  Gly  Ile  Ser  Asp
          505                      510                       515

GTT  CAG  ATC  TCA  CCA  ACA  TTA  CAG  AGG  CAT  AAT  AAT  GTG  AAT  CAA  ATG        1698
Val  Gln  Ile  Ser  Pro  Thr  Leu  Gln  Arg  His  Asn  Asn  Val  Asn  Gln  Met
520                           525                      530                      535

GTG  TTT  CAC  AAA  ATC  AGG  AAT  GAA  GAT  TTA  ATA  TTT  AAT  GAA  AGT  CTT        1746
Val  Phe  His  Lys  Ile  Arg  Asn  Glu  Asp  Leu  Ile  Phe  Asn  Glu  Ser  Leu
                    540                      545                      550

GGC  CAA  GGT  ACT  TTT  ACA  AAA  ATT  TTT  AAA  GGT  GTA  AGA  AGA  GAA  GTT        1794
Gly  Gln  Gly  Thr  Phe  Thr  Lys  Ile  Phe  Lys  Gly  Val  Arg  Arg  Glu  Val
               555                      560                      565

GGA  GAT  TAT  GGT  CAA  CTG  CAC  AAA  ACG  GAA  GTT  CTT  TTG  AAA  GTC  CTA        1842
Gly  Asp  Tyr  Gly  Gln  Leu  His  Lys  Thr  Glu  Val  Leu  Leu  Lys  Val  Leu
          570                      575                      580

GAT  AAA  GCA  CAT  AGG  AAC  TAT  TCA  GAG  TCT  TTC  TTC  GAA  GCA  GCA  AGC        1890
Asp  Lys  Ala  His  Arg  Asn  Tyr  Ser  Glu  Ser  Phe  Phe  Glu  Ala  Ala  Ser
          585                      590                      595

ATG  ATG  AGT  CAG  CTT  TCT  CAC  AAG  CAT  TTG  GTT  TTG  AAT  TAT  GGT  GTC        1938
Met  Met  Ser  Gln  Leu  Ser  His  Lys  His  Leu  Val  Leu  Asn  Tyr  Gly  Val
600                           605                      610                      615

TGT  GTC  TGT  GGA  GAG  GAG  AAC  ATT  CTG  GTT  CAA  GAA  TTT  GTA  AAA  TTT        1986
Cys  Val  Cys  Gly  Glu  Glu  Asn  Ile  Leu  Val  Gln  Glu  Phe  Val  Lys  Phe
               620                      625                      630

GGA  TCA  CTG  GAT  ACA  TAC  CTG  AAG  AAG  AAC  AAA  AAT  TCC  ATA  AAT  ATA        2034
Gly  Ser  Leu  Asp  Thr  Tyr  Leu  Lys  Lys  Asn  Lys  Asn  Ser  Ile  Asn  Ile
               635                      640                      645

TTA  TGG  AAA  CTT  GGA  GTG  GCT  AAG  CAG  TTG  GCA  TGG  GCC  ATG  CAT  TTT        2082
Leu  Trp  Lys  Leu  Gly  Val  Ala  Lys  Gln  Leu  Ala  Trp  Ala  Met  His  Phe
          650                      655                      660

CTA  GAA  GAA  AAA  TCC  CTT  ATT  CAT  GGG  AAT  GTG  TGT  GCT  AAA  AAT  ATC        2130
Leu  Glu  Glu  Lys  Ser  Leu  Ile  His  Gly  Asn  Val  Cys  Ala  Lys  Asn  Ile
     665                      670                      675

CTG  CTT  ATC  AGA  GAA  GAA  GAC  AGG  AGA  ACG  GGG  AAC  CCA  CCT  TTC  ATC        2178
Leu  Leu  Ile  Arg  Glu  Glu  Asp  Arg  Arg  Thr  Gly  Asn  Pro  Pro  Phe  Ile
680                           685                      690                      695

AAA  CTT  AGT  GAT  CCT  GGC  ATT  AGC  ATT  ACA  GTT  CTA  CCG  AAG  GAC  ATT        2226
Lys  Leu  Ser  Asp  Pro  Gly  Ile  Ser  Ile  Thr  Val  Leu  Pro  Lys  Asp  Ile
               700                      705                      710

CTT  CAG  GAG  AGA  ATA  CCA  TGG  GTA  CCT  CCT  GAA  TGC  ATT  GAG  AAT  CCT        2274
Leu  Gln  Glu  Arg  Ile  Pro  Trp  Val  Pro  Pro  Glu  Cys  Ile  Glu  Asn  Pro
               715                      720                      725

AAA  AAT  CTC  AAT  CTG  GCA  ACA  GAC  AAG  TGG  AGC  TTC  GGG  ACC  ACT  CTG        2322
Lys  Asn  Leu  Asn  Leu  Ala  Thr  Asp  Lys  Trp  Ser  Phe  Gly  Thr  Thr  Leu
               730                      735                      740

TGG  GAG  ATC  TGC  AGT  GGA  GGA  GAT  AAG  CCC  CTG  AGT  GCT  CTG  GAT  TCT        2370
Trp  Glu  Ile  Cys  Ser  Gly  Gly  Asp  Lys  Pro  Leu  Ser  Ala  Leu  Asp  Ser
     745                      750                      755

CAA  AGA  AAG  CTG  CAG  TTC  TAT  GAA  GAT  AAG  CAT  CAG  CTT  CCT  GCA  CCC        2418
Gln  Arg  Lys  Leu  Gln  Phe  Tyr  Glu  Asp  Lys  His  Gln  Leu  Pro  Ala  Pro
760                           765                      770                      775

AAG  TGG  ACA  GAG  TTA  GCA  AAC  CTT  ATA  AAT  AAT  TGC  ATG  GAC  TAT  GAG        2466
Lys  Trp  Thr  Glu  Leu  Ala  Asn  Leu  Ile  Asn  Asn  Cys  Met  Asp  Tyr  Glu
                    780                      785                      790
```

```
CCA GAT TTC AGG CCT GCT TTC AGA GCT GTC ATC CGT GAT CTT AAC AGC    2514
Pro Asp Phe Arg Pro Ala Phe Arg Ala Val Ile Arg Asp Leu Asn Ser
            795             800                 805

CTG TTT ACT CCA GAT TAT GAA CTA CTA ACA GAA AAT GAC ATG CTA CCA    2562
Leu Phe Thr Pro Asp Tyr Glu Leu Leu Thr Glu Asn Asp Met Leu Pro
        810                 815                 820

AAC ATG AGA ATA GGT GCC CTA GGG TTT TCT GGT GCT TTT GAA GAC AGG    2610
Asn Met Arg Ile Gly Ala Leu Gly Phe Ser Gly Ala Phe Glu Asp Arg
        825                 830                 835

GAC CCT ACA CAG TTT GAA GAG AGA CAC TTG AAG TTT CTA CAG CAG CTT    2658
Asp Pro Thr Gln Phe Glu Glu Arg His Leu Lys Phe Leu Gln Gln Leu
840                 845                 850                 855

GGC AAA GGT AAC TTC GGG AGT GTG GAG ATG TGC CGC TAT GAC CCG CTG    2706
Gly Lys Gly Asn Phe Gly Ser Val Glu Met Cys Arg Tyr Asp Pro Leu
                860                 865                 870

CAG GAC AAC ACT GGC GAG GTG GTC GCT GTG AAG AAA CTC CAG CAC AGC    2754
Gln Asp Asn Thr Gly Glu Val Val Ala Val Lys Lys Leu Gln His Ser
        875                 880                 885

ACT GAA GAG CAC CTC CGA GAC TTT GAG AGG GAG ATC GAG ATC CTG AAA    2802
Thr Glu Glu His Leu Arg Asp Phe Glu Arg Glu Ile Glu Ile Leu Lys
        890                 895                 900

TCC TTG CAG CAT GAC AAC ATC GTC AAG TAC AAG GGA GTG TGC TAC AGT    2850
Ser Leu Gln His Asp Asn Ile Val Lys Tyr Lys Gly Val Cys Tyr Ser
905                 910                 915

GCG GGT CGG CGC AAC CTA AGA TTA ATT ATG GAA TAT TTA CCA TAT GGA    2898
Ala Gly Arg Arg Asn Leu Arg Leu Ile Met Glu Tyr Leu Pro Tyr Gly
920                 925                 930                 935

AGT TTA CGA GAC TAT CTC CAA AAA CAT AAA GAA CGG ATA GAT CAC AAA    2946
Ser Leu Arg Asp Tyr Leu Gln Lys His Lys Glu Arg Ile Asp His Lys
                940                 945                 950

AAA CTT CTT CAA TAC ACA TCT CAG ATA TGC AAG GGC ATG GAA TAT CTT    2994
Lys Leu Leu Gln Tyr Thr Ser Gln Ile Cys Lys Gly Met Glu Tyr Leu
        955                 960                 965

GGT ACA AAA AGG TAT ATC CAC AGG GAC CTG GCA ACA AGG AAC ATA TTG    3042
Gly Thr Lys Arg Tyr Ile His Arg Asp Leu Ala Thr Arg Asn Ile Leu
        970                 975                 980

GTG GAA AAT GAG AAC AGG GTT AAA ATA GGA GAC TTC GGA TTA ACC AAA    3090
Val Glu Asn Glu Asn Arg Val Lys Ile Gly Asp Phe Gly Leu Thr Lys
985                 990                 995

GTC TTG CCG CAG GAC AAA GAA TAC TAC AAA GTA AAG GAG CCA GGG GAA    3138
Val Leu Pro Gln Asp Lys Glu Tyr Tyr Lys Val Lys Glu Pro Gly Glu
1000                1005                1010                1015

AGC CCC ATA TTC TGG TAC GCA CCT GAA TCC TTG ACG GAG AGC AAG TTT    3186
Ser Pro Ile Phe Trp Tyr Ala Pro Glu Ser Leu Thr Glu Ser Lys Phe
                1020                1025                1030

TCT GTG GCC TCA GAT GTG TGG AGC TTT GGA GTG GTT CTA TAC GAA CTT    3234
Ser Val Ala Ser Asp Val Trp Ser Phe Gly Val Val Leu Tyr Glu Leu
        1035                1040                1045

TTC ACA TAC ATC GAG AAG AGT AAA AGT CCA CCC GTG GAA TTT ATG CGA    3282
Phe Thr Tyr Ile Glu Lys Ser Lys Ser Pro Pro Val Glu Phe Met Arg
        1050                1055                1060

ATG ATT GGC AAT GAT AAA CAA GGG CAA ATG ATT GTG TTC CAT TTG ATA    3330
Met Ile Gly Asn Asp Lys Gln Gly Gln Met Ile Val Phe His Leu Ile
1065                1070                1075

GAG CTA CTG AAG AGC AAC GGA AGA TTG CCA AGG CCA GAA GGA TGC CCA    3378
Glu Leu Leu Lys Ser Asn Gly Arg Leu Pro Arg Pro Glu Gly Cys Pro
1080                1085                1090                1095

GAT GAG ATT TAT GTG ATC ATG ACA GAG TGC TGG AAC AAC AAT GTG AGC    3426
Asp Glu Ile Tyr Val Ile Met Thr Glu Cys Trp Asn Asn Asn Val Ser
                1100                1105                1110
```

```
CAG CGT CCC TCC TTC AGG GAC CTT TCG TTC GGG TGG ATC AAA TCC GGG    3474
Gln Arg Pro Ser Phe Arg Asp Leu Ser Phe Gly Trp Ile Lys Ser Gly
        1115                1120                1125

ACA GTA TAGCTGCGTG AAAGAGATGG CCTTCACTCA GAGACCAAGC AGACTTCCAG    3530
Thr Val

AACCAGAACA AAGCTCTGTA GCCTTGTGTC TACACATCCT TATCATGATG CTAGCTAGGC  3590

AGAAGAAACT GTGACGCCGT CTGCTCAAAG CTTTGCTTC                        3629
```

( 2 ) INFORMATION FOR SEQ ID NO:9:

( i ) SEQUENCE CHARACTERISTICS:
        ( A ) LENGTH: 1129 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Met Gly Met Ala Cys Leu Thr Met Thr Glu Met Glu Ala Thr Ser Thr
 1               5                  10                  15

Ser Pro Val His Gln Asn Gly Asp Ile Pro Gly Ser Ala Asn Ser Val
                20                  25                  30

Lys Gln Ile Glu Pro Val Leu Gln Val Tyr Leu Tyr His Ser Leu Gly
            35                  40                  45

Gln Ala Glu Gly Glu Tyr Leu Lys Phe Pro Ser Gly Glu Tyr Val Ala
        50                  55                  60

Glu Glu Ile Cys Val Ala Ala Ser Lys Ala Cys Gly Ile Thr Pro Val
 65                 70                  75                  80

Tyr His Asn Met Phe Ala Leu Met Ser Glu Thr Glu Arg Ile Trp Tyr
                85                  90                  95

Pro Pro Asn His Val Phe His Ile Asp Glu Ser Thr Arg His Asp Ile
                100                 105                 110

Leu Tyr Arg Ile Arg Phe Tyr Phe Pro His Trp Tyr Cys Ser Gly Ser
            115                 120                 125

Ser Arg Thr Tyr Arg Tyr Gly Val Ser Arg Gly Ala Glu Ala Pro Leu
        130                 135                 140

Leu Asp Asp Phe Val Met Ser Tyr Leu Phe Ala Gln Trp Arg His Asp
145                 150                 155                 160

Phe Val His Gly Trp Ile Lys Val Pro Val Thr His Glu Thr Gln Glu
                165                 170                 175

Glu Cys Leu Gly Met Ala Val Leu Asp Met Met Arg Ile Ala Lys Glu
            180                 185                 190

Lys Asp Gln Thr Pro Leu Ala Val Tyr Asn Ser Val Ser Tyr Lys Thr
        195                 200                 205

Phe Leu Pro Lys Cys Val Arg Ala Lys Ile Gln Asp Tyr His Ile Leu
210                 215                 220

Thr Arg Lys Arg Ile Arg Tyr Arg Phe Arg Arg Phe Ile Gln Gln Phe
225                 230                 235                 240

Ser Gln Cys Lys Ala Thr Ala Arg Asn Leu Lys Leu Lys Tyr Leu Ile
                245                 250                 255

Asn Leu Glu Thr Leu Gln Ser Ala Phe Tyr Thr Glu Gln Phe Glu Val
            260                 265                 270

Lys Glu Ser Ala Arg Gly Pro Ser Gly Glu Glu Ile Phe Ala Thr Ile
        275                 280                 285

Ile Ile Thr Gly Asn Gly Gly Ile Gln Trp Ser Arg Gly Lys His Lys
290                 295                 300
```

```
Glu  Ser  Glu  Thr  Leu  Thr  Glu  Gln  Asp  Val  Gln  Leu  Tyr  Cys  Asp  Phe
305                      310                      315                      320

Pro  Asp  Ile  Ile  Asp  Val  Ser  Ile  Lys  Gln  Ala  Asn  Gln  Glu  Cys  Ser
                    325                      330                      335

Asn  Glu  Ser  Arg  Ile  Val  Thr  Val  His  Lys  Gln  Asp  Gly  Lys  Val  Leu
               340                      345                      350

Glu  Ile  Glu  Leu  Ser  Ser  Leu  Lys  Glu  Ala  Leu  Ser  Phe  Val  Ser  Leu
               355                      360                      365

Ile  Asp  Gly  Tyr  Tyr  Arg  Leu  Thr  Ala  Asp  Ala  His  His  Tyr  Leu  Cys
     370                      375                      380

Lys  Glu  Val  Ala  Pro  Pro  Ala  Val  Leu  Glu  Asn  Ile  His  Ser  Asn  Cys
385                      390                      395                      400

His  Gly  Pro  Ile  Ser  Met  Asp  Phe  Ala  Ile  Ser  Lys  Leu  Lys  Lys  Ala
                    405                      410                      415

Gly  Asn  Gln  Thr  Gly  Leu  Tyr  Val  Leu  Arg  Cys  Ser  Pro  Lys  Asp  Phe
               420                      425                      430

Asn  Lys  Tyr  Phe  Leu  Thr  Phe  Ala  Val  Glu  Arg  Glu  Asn  Val  Ile  Glu
          435                      440                      445

Tyr  Lys  His  Cys  Leu  Ile  Thr  Lys  Asn  Glu  Asn  Gly  Glu  Tyr  Asn  Leu
450                      455                      460

Ser  Gly  Thr  Lys  Arg  Asn  Phe  Ser  Asn  Leu  Lys  Asp  Leu  Leu  Asn  Cys
465                      470                      475                      480

Tyr  Gln  Met  Glu  Thr  Val  Arg  Ser  Asp  Ser  Ile  Ile  Phe  Gln  Phe  Thr
                    485                      490                      495

Lys  Cys  Cys  Pro  Pro  Lys  Pro  Lys  Asp  Lys  Ser  Asn  Leu  Leu  Val  Phe
               500                      505                      510

Arg  Thr  Asn  Gly  Ile  Ser  Asp  Val  Gln  Ile  Ser  Pro  Thr  Leu  Gln  Arg
          515                      520                      525

His  Asn  Asn  Val  Asn  Gln  Met  Val  Phe  His  Lys  Ile  Arg  Asn  Glu  Asp
     530                      535                      540

Leu  Ile  Phe  Asn  Glu  Ser  Leu  Gly  Gln  Gly  Thr  Phe  Thr  Lys  Ile  Phe
545                      550                      555                      560

Lys  Gly  Val  Arg  Arg  Glu  Val  Gly  Asp  Tyr  Gly  Gln  Leu  His  Lys  Thr
                    565                      570                      575

Glu  Val  Leu  Leu  Lys  Val  Leu  Asp  Lys  Ala  His  Arg  Asn  Tyr  Ser  Glu
               580                      585                      590

Ser  Phe  Phe  Glu  Ala  Ala  Ser  Met  Met  Ser  Gln  Leu  Ser  His  Lys  His
          595                      600                      605

Leu  Val  Leu  Asn  Tyr  Gly  Val  Cys  Val  Cys  Gly  Glu  Glu  Asn  Ile  Leu
     610                      615                      620

Val  Gln  Glu  Phe  Val  Lys  Phe  Gly  Ser  Leu  Asp  Thr  Tyr  Leu  Lys  Lys
625                      630                      635                      640

Asn  Lys  Asn  Ser  Ile  Asn  Ile  Leu  Trp  Lys  Leu  Gly  Val  Ala  Lys  Gln
                    645                      650                      655

Leu  Ala  Trp  Ala  Met  His  Phe  Leu  Glu  Glu  Lys  Ser  Leu  Ile  His  Gly
               660                      665                      670

Asn  Val  Cys  Ala  Lys  Asn  Ile  Leu  Leu  Ile  Arg  Glu  Glu  Asp  Arg  Arg
          675                      680                      685

Thr  Gly  Asn  Pro  Pro  Phe  Ile  Lys  Leu  Ser  Asp  Pro  Gly  Ile  Ser  Ile
     690                      695                      700

Thr  Val  Leu  Pro  Lys  Asp  Ile  Leu  Gln  Glu  Arg  Ile  Pro  Trp  Val  Pro
705                      710                      715                      720

Pro  Glu  Cys  Ile  Glu  Asn  Pro  Lys  Asn  Leu  Asn  Leu  Ala  Thr  Asp  Lys
```

|       |       |       |       |       | 725   |       |       |       | 730   |       |       |       | 735   |       |
|-------|-------|-------|-------|-------|-------|-------|-------|-------|-------|-------|-------|-------|-------|-------|
| Trp | Ser | Phe | Gly | Thr | Thr | Leu | Trp | Glu | Ile | Cys | Ser | Gly | Gly | Asp | Lys |

Trp Ser Phe Gly Thr Thr Leu Trp Glu Ile Cys Ser Gly Gly Asp Lys
                         740                 745             750

Pro Leu Ser Ala Leu Asp Ser Gln Arg Lys Leu Gln Phe Tyr Glu Asp
            755                 760             765

Lys His Gln Leu Pro Ala Pro Lys Trp Thr Glu Leu Ala Asn Leu Ile
    770             775                 780

Asn Asn Cys Met Asp Tyr Glu Pro Asp Phe Arg Pro Ala Phe Arg Ala
785             790                 795                     800

Val Ile Arg Asp Leu Asn Ser Leu Phe Thr Pro Asp Tyr Glu Leu Leu
            805                 810             815

Thr Glu Asn Asp Met Leu Pro Asn Met Arg Ile Gly Ala Leu Gly Phe
            820                 825             830

Ser Gly Ala Phe Glu Asp Arg Asp Pro Thr Gln Phe Glu Glu Arg His
        835             840                 845

Leu Lys Phe Leu Gln Gln Leu Gly Lys Gly Asn Phe Gly Ser Val Glu
    850                 855                 860

Met Cys Arg Tyr Asp Pro Leu Gln Asp Asn Thr Gly Glu Val Val Ala
865             870                 875                     880

Val Lys Lys Leu Gln His Ser Thr Glu Glu His Leu Arg Asp Phe Glu
                885                 890                 895

Arg Glu Ile Glu Ile Leu Lys Ser Leu Gln His Asp Asn Ile Val Lys
            900                 905                 910

Tyr Lys Gly Val Cys Tyr Ser Ala Gly Arg Arg Asn Leu Arg Leu Ile
        915                 920                 925

Met Glu Tyr Leu Pro Tyr Gly Ser Leu Arg Asp Tyr Leu Gln Lys His
    930                 935                 940

Lys Glu Arg Ile Asp His Lys Lys Leu Leu Gln Tyr Thr Ser Gln Ile
945                 950                 955                 960

Cys Lys Gly Met Glu Tyr Leu Gly Thr Lys Arg Tyr Ile His Arg Asp
                965                 970                 975

Leu Ala Thr Arg Asn Ile Leu Val Glu Asn Glu Asn Arg Val Lys Ile
            980                 985                 990

Gly Asp Phe Gly Leu Thr Lys Val Leu Pro Gln Asp Lys Glu Tyr Tyr
        995                 1000                1005

Lys Val Lys Glu Pro Gly Glu Ser Pro Ile Phe Trp Tyr Ala Pro Glu
    1010                1015                1020

Ser Leu Thr Glu Ser Lys Phe Ser Val Ala Ser Asp Val Trp Ser Phe
1025                1030                1035                1040

Gly Val Val Leu Tyr Glu Leu Phe Thr Tyr Ile Glu Lys Ser Lys Ser
                1045                1050                1055

Pro Pro Val Glu Phe Met Arg Met Ile Gly Asn Asp Lys Gln Gly Gln
            1060                1065                1070

Met Ile Val Phe His Leu Ile Glu Leu Leu Lys Ser Asn Gly Arg Leu
        1075                1080                1085

Pro Arg Pro Glu Gly Cys Pro Asp Glu Ile Tyr Val Ile Met Thr Glu
    1090                1095                1100

Cys Trp Asn Asn Asn Val Ser Gln Arg Pro Ser Phe Arg Asp Leu Ser
1105                1110                1115                1120

Phe Gly Trp Ile Lys Ser Gly Thr Val
                1125

( 2 ) INFORMATION FOR SEQ ID NO:10:

( i ) SEQUENCE CHARACTERISTICS:
   ( A ) LENGTH: 3429 base pairs
   ( B ) TYPE: nucleic acid
   ( C ) STRANDEDNESS: single
   ( D ) TOPOLOGY: linear ( i x ) FEATURE:
   ( A ) NAME/KEY: CDS
   ( B ) LOCATION: 1..3426

( x i ) SEQUENCE DESCRIPTION: SEQ ID NO:10:

| | | | | | | | | | | | | | | | | |
|---|---|---|---|---|---|---|---|---|---|---|---|---|---|---|---|---|
| ATG | GCT | TTC | TGT | GCT | AAA | ATG | AGG | AGC | TCC | AAG | AAG | ACT | GAG | GTG | AAC | 48 |
| Met | Ala | Phe | Cys | Ala | Lys | Met | Arg | Ser | Ser | Lys | Lys | Thr | Glu | Val | Asn | |
| 1 | | | | 5 | | | | | 10 | | | | | 15 | | |
| CTG | GAG | GCC | CCT | GAG | CCA | GGG | GTG | GAA | GTG | ATC | TTC | TAT | CTG | TCG | GAC | 96 |
| Leu | Glu | Ala | Pro | Glu | Pro | Gly | Val | Glu | Val | Ile | Phe | Tyr | Leu | Ser | Asp | |
| | | | 20 | | | | | 25 | | | | | 30 | | | |
| AGG | GAG | CCC | CTC | CGG | CTG | GGC | AGT | GGA | GAG | TAC | ACA | GCA | GAG | GAA | CTG | 144 |
| Arg | Glu | Pro | Leu | Arg | Leu | Gly | Ser | Gly | Glu | Tyr | Thr | Ala | Glu | Glu | Leu | |
| | | 35 | | | | | 40 | | | | | 45 | | | | |
| TGC | ATC | AGG | GCT | GCA | CAG | GCA | TGC | CGT | ATC | TCT | CCT | CTT | TGT | CAC | AAC | 192 |
| Cys | Ile | Arg | Ala | Ala | Gln | Ala | Cys | Arg | Ile | Ser | Pro | Leu | Cys | His | Asn | |
| | 50 | | | | | 55 | | | | | 60 | | | | | |
| CTC | TTT | GCC | CTG | TAT | GAC | GAG | AAC | ACC | AAG | CTC | TGG | TAT | GCT | CCA | AAT | 240 |
| Leu | Phe | Ala | Leu | Tyr | Asp | Glu | Asn | Thr | Lys | Leu | Trp | Tyr | Ala | Pro | Asn | |
| 65 | | | | | 70 | | | | | 75 | | | | | 80 | |
| CGC | ACC | ATC | ACC | GTT | GAT | GAC | AAG | ATG | TCC | CTC | CGG | CTC | CAC | TAC | CGG | 288 |
| Arg | Thr | Ile | Thr | Val | Asp | Asp | Lys | Met | Ser | Leu | Arg | Leu | His | Tyr | Arg | |
| | | | | 85 | | | | | 90 | | | | | 95 | | |
| ATG | AGG | TTC | TAT | TTC | ACC | AAT | TGG | CAT | GGA | ACC | AAC | GAC | AAT | GAG | CAG | 336 |
| Met | Arg | Phe | Tyr | Phe | Thr | Asn | Trp | His | Gly | Thr | Asn | Asp | Asn | Glu | Gln | |
| | | | 100 | | | | | 105 | | | | | 110 | | | |
| TCA | GTG | TGG | CGT | CAT | TCT | CCA | AAG | AAG | CAG | AAA | AAT | GGC | TAC | GAG | AAA | 384 |
| Ser | Val | Trp | Arg | His | Ser | Pro | Lys | Lys | Gln | Lys | Asn | Gly | Tyr | Glu | Lys | |
| | | 115 | | | | | 120 | | | | | 125 | | | | |
| AAA | AAG | ATT | CCA | GAT | GCA | ACC | CCT | CTC | CTT | GAT | GCC | AGC | TCA | CTG | GAG | 432 |
| Lys | Lys | Ile | Pro | Asp | Ala | Thr | Pro | Leu | Leu | Asp | Ala | Ser | Ser | Leu | Glu | |
| | 130 | | | | | 135 | | | | | 140 | | | | | |
| TAT | CTG | TTT | GCT | CAG | GGA | CAG | TAT | GAT | TTG | GTG | AAA | TGC | CTG | GCT | CCT | 480 |
| Tyr | Leu | Phe | Ala | Gln | Gly | Gln | Tyr | Asp | Leu | Val | Lys | Cys | Leu | Ala | Pro | |
| 145 | | | | | 150 | | | | | 155 | | | | | 160 | |
| ATT | CGA | GAC | CCC | AAG | ACC | GAG | CAG | GAT | GGA | CAT | GAT | ATT | GAG | AAC | GAG | 528 |
| Ile | Arg | Asp | Pro | Lys | Thr | Glu | Gln | Asp | Gly | His | Asp | Ile | Glu | Asn | Glu | |
| | | | | 165 | | | | | 170 | | | | | 175 | | |
| TGT | CTA | GGG | ATG | GCT | GTC | CTG | GCC | ATC | TCA | CAC | TAT | GCC | ATG | ATG | AAG | 576 |
| Cys | Leu | Gly | Met | Ala | Val | Leu | Ala | Ile | Ser | His | Tyr | Ala | Met | Met | Lys | |
| | | | 180 | | | | | 185 | | | | | 190 | | | |
| AAG | ATG | CAG | TTG | CCA | GAA | CTG | CCC | AAG | GAC | ATC | AGC | TAC | AAG | CGA | TAT | 624 |
| Lys | Met | Gln | Leu | Pro | Glu | Leu | Pro | Lys | Asp | Ile | Ser | Tyr | Lys | Arg | Tyr | |
| | | 195 | | | | | 200 | | | | | 205 | | | | |
| ATT | CCA | GAA | ACA | TTG | AAT | AAG | TCC | ATC | AGA | CAG | AGG | AAC | CTT | CTC | ACC | 672 |
| Ile | Pro | Glu | Thr | Leu | Asn | Lys | Ser | Ile | Arg | Gln | Arg | Asn | Leu | Leu | Thr | |
| | 210 | | | | | 215 | | | | | 220 | | | | | |
| AGG | ATG | CGG | ATA | AAT | AAT | GTT | TTC | AAG | GAT | TTC | CTA | AAG | GAA | TTT | AAC | 720 |
| Arg | Met | Arg | Ile | Asn | Asn | Val | Phe | Lys | Asp | Phe | Leu | Lys | Glu | Phe | Asn | |
| 225 | | | | | 230 | | | | | 235 | | | | | 240 | |
| AAC | AAG | ACC | ATT | TGT | GAC | AGC | AGC | GTG | TCC | ACG | CAT | GAC | CTG | AAG | GTG | 768 |
| Asn | Lys | Thr | Ile | Cys | Asp | Ser | Ser | Val | Ser | Thr | His | Asp | Leu | Lys | Val | |
| | | | | 245 | | | | | 250 | | | | | 255 | | |
| AAA | TAC | TTG | GCT | ACC | TTG | GAA | ACT | TTG | ACA | AAA | CAT | TAC | GGT | GCT | GAA | 816 |
| Lys | Tyr | Leu | Ala | Thr | Leu | Glu | Thr | Leu | Thr | Lys | His | Tyr | Gly | Ala | Glu | |
| | | | | | 260 | | | | | 265 | | | | | 270 | |

| | | | | | | | | | | | | | | | | |
|---|---|---|---|---|---|---|---|---|---|---|---|---|---|---|---|---|
| ATA | TTT | GAG | ACT | TCC | ATG | TTA | CTG | ATT | TCA | TCA | GAA | AAT | GAG | ATG | AAT | 864 |
| Ile | Phe | Glu | Thr | Ser | Met | Leu | Leu | Ile | Ser | Ser | Glu | Asn | Glu | Met | Asn | |
| | | 275 | | | | 280 | | | | | 285 | | | | | |
| TGG | TTT | CAT | TCG | AAT | GAC | GGT | GGA | AAC | GTT | CTC | TAC | TAC | GAA | GTG | ATG | 912 |
| Trp | Phe | His | Ser | Asn | Asp | Gly | Gly | Asn | Val | Leu | Tyr | Tyr | Glu | Val | Met | |
| | | 290 | | | | 295 | | | | 300 | | | | | | |
| GTG | ACT | GGG | AAT | CTT | GGA | ATC | CAG | TGG | AGG | CAT | AAA | CCA | AAT | GTT | GTT | 960 |
| Val | Thr | Gly | Asn | Leu | Gly | Ile | Gln | Trp | Arg | His | Lys | Pro | Asn | Val | Val | |
| | 305 | | | | 310 | | | | | 315 | | | | | 320 | |
| TCT | GTT | GAA | AAG | GAA | AAA | AAT | AAA | CTG | AAG | CGG | AAA | AAA | CTG | GAA | AAT | 1008 |
| Ser | Val | Glu | Lys | Glu | Lys | Asn | Lys | Leu | Lys | Arg | Lys | Lys | Leu | Glu | Asn | |
| | | | | 325 | | | | | 330 | | | | | 335 | | |
| AAA | GAC | AAG | AAG | GAT | GAG | GAG | AAA | AAC | AAG | ATC | CGG | GAA | GAG | TGG | AAC | 1056 |
| Lys | Asp | Lys | Lys | Asp | Glu | Glu | Lys | Asn | Lys | Ile | Arg | Glu | Glu | Trp | Asn | |
| | | | 340 | | | | | 345 | | | | | 350 | | | |
| AAT | TTT | TCA | TTC | TTC | CCT | GAA | ATC | ACT | CAC | ATT | GTA | ATA | AAG | GAG | TCT | 1104 |
| Asn | Phe | Ser | Phe | Phe | Pro | Glu | Ile | Thr | His | Ile | Val | Ile | Lys | Glu | Ser | |
| | | 355 | | | | | 360 | | | | | 365 | | | | |
| GTG | GTC | AGC | ATT | AAC | AAG | CAG | GAC | AAC | AAG | AAA | ATG | GAA | CTG | AAG | CTC | 1152 |
| Val | Val | Ser | Ile | Asn | Lys | Gln | Asp | Asn | Lys | Lys | Met | Glu | Leu | Lys | Leu | |
| | | 370 | | | | 375 | | | | | 380 | | | | | |
| TCT | TCC | CAC | GAG | GAG | GCC | TTG | TCC | TTT | GTG | TCC | CTG | GTA | GAT | GGC | TAC | 1200 |
| Ser | Ser | His | Glu | Glu | Ala | Leu | Ser | Phe | Val | Ser | Leu | Val | Asp | Gly | Tyr | |
| 385 | | | | | 390 | | | | | 395 | | | | | 400 | |
| TTC | CGG | CTC | ACA | GCA | GAT | GCC | CAT | CAT | TAC | CTC | TGC | ACC | GAC | GTG | GCC | 1248 |
| Phe | Arg | Leu | Thr | Ala | Asp | Ala | His | His | Tyr | Leu | Cys | Thr | Asp | Val | Ala | |
| | | | | 405 | | | | | 410 | | | | | 415 | | |
| CCC | CCG | TTG | ATC | GTC | CAC | AAC | ATA | CAG | AAT | GGC | TGT | CAT | GGT | CCA | ATC | 1296 |
| Pro | Pro | Leu | Ile | Val | His | Asn | Ile | Gln | Asn | Gly | Cys | His | Gly | Pro | Ile | |
| | | | 420 | | | | | 425 | | | | | 430 | | | |
| TGT | ACA | GAA | TAC | GCC | ATC | AAT | AAA | TTG | CGG | CAA | GAA | GGA | AGC | GAG | GAG | 1344 |
| Cys | Thr | Glu | Tyr | Ala | Ile | Asn | Lys | Leu | Arg | Gln | Glu | Gly | Ser | Glu | Glu | |
| | | 435 | | | | | 440 | | | | | 445 | | | | |
| GGG | ATG | TAC | GTG | CTG | AGG | TGG | AGC | TGC | ACC | GAC | TTT | GAC | AAC | ATC | CTC | 1392 |
| Gly | Met | Tyr | Val | Leu | Arg | Trp | Ser | Cys | Thr | Asp | Phe | Asp | Asn | Ile | Leu | |
| | 450 | | | | | 455 | | | | | 460 | | | | | |
| ATG | ACC | GTC | ACC | TGC | TTT | GAG | AAG | TCT | GAG | CAG | GTG | CAG | GGT | GCC | CAG | 1440 |
| Met | Thr | Val | Thr | Cys | Phe | Glu | Lys | Ser | Glu | Gln | Val | Gln | Gly | Ala | Gln | |
| 465 | | | | | 470 | | | | | 475 | | | | | 480 | |
| AAG | CAG | TTC | AAG | AAC | TTT | CAG | ATC | GAG | GTG | CAG | AAG | GGC | CGC | TAC | AGT | 1488 |
| Lys | Gln | Phe | Lys | Asn | Phe | Gln | Ile | Glu | Val | Gln | Lys | Gly | Arg | Tyr | Ser | |
| | | | | 485 | | | | | 490 | | | | | 495 | | |
| CTG | CAC | GGT | TCG | GAC | CGC | AGC | TTC | CCC | AGC | TTG | GGA | GAC | CTC | ATG | AGC | 1536 |
| Leu | His | Gly | Ser | Asp | Arg | Ser | Phe | Pro | Ser | Leu | Gly | Asp | Leu | Met | Ser | |
| | | | 500 | | | | | 505 | | | | | 510 | | | |
| CAC | CTC | AAG | AAG | CAG | ATC | CTG | CGC | ACG | GAT | AAC | ATC | AGC | TTC | ATG | CTA | 1584 |
| His | Leu | Lys | Lys | Gln | Ile | Leu | Arg | Thr | Asp | Asn | Ile | Ser | Phe | Met | Leu | |
| | | 515 | | | | | 520 | | | | | 525 | | | | |
| AAA | CGC | TGC | TGC | CAG | CCC | AAG | CCC | CGA | GAA | ATC | TCC | AAC | CTG | CTG | GTG | 1632 |
| Lys | Arg | Cys | Cys | Gln | Pro | Lys | Pro | Arg | Glu | Ile | Ser | Asn | Leu | Leu | Val | |
| | 530 | | | | | 535 | | | | | 540 | | | | | |
| GCT | ACT | AAG | AAA | GCC | CAG | GAG | TGG | CAG | CCC | GTC | TAC | CCC | ATG | AGC | CAG | 1680 |
| Ala | Thr | Lys | Lys | Ala | Gln | Glu | Trp | Gln | Pro | Val | Tyr | Pro | Met | Ser | Gln | |
| 545 | | | | | 550 | | | | | 555 | | | | | 560 | |
| CTG | AGT | TTC | GAT | CGG | ATC | CTC | AAG | AAG | GAT | CTG | GTG | CAG | GGC | GAG | CAC | 1728 |
| Leu | Ser | Phe | Asp | Arg | Ile | Leu | Lys | Lys | Asp | Leu | Val | Gln | Gly | Glu | His | |
| | | | | 565 | | | | | 570 | | | | | 575 | | |
| CTT | GGG | AGA | GGC | ACG | AGA | ACA | CAC | ATC | TAT | TCT | GGG | ACC | CTG | ATG | GAT | 1776 |
| Leu | Gly | Arg | Gly | Thr | Arg | Thr | His | Ile | Tyr | Ser | Gly | Thr | Leu | Met | Asp | |
| | | | 580 | | | | | 585 | | | | | 590 | | | |

| | | | | | | | | | | | | | | | | |
|---|---|---|---|---|---|---|---|---|---|---|---|---|---|---|---|---|
| TAC | AAG | GAT | GAC | GAA | GGA | ACT | TCT | GAA | GAG | AAG | AAG | ATA | AAA | GTG | ATC | 1824 |
| Tyr | Lys | Asp | Asp | Glu | Gly | Thr | Ser | Glu | Glu | Lys | Lys | Ile | Lys | Val | Ile | |
| | | 595 | | | | | 600 | | | | | 605 | | | | |
| CTC | AAA | GTC | TTA | GAC | CCC | AGC | CAC | AGG | GAT | ATT | TCC | CTG | GCC | TTC | TTC | 1872 |
| Leu | Lys | Val | Leu | Asp | Pro | Ser | His | Arg | Asp | Ile | Ser | Leu | Ala | Phe | Phe | |
| | 610 | | | | | 615 | | | | | 620 | | | | | |
| GAG | GCA | GCC | AGC | ATG | ATG | AGA | CAG | GTC | TCC | CAC | AAA | CAC | ATC | GTG | TAC | 1920 |
| Glu | Ala | Ala | Ser | Met | Met | Arg | Gln | Val | Ser | His | Lys | His | Ile | Val | Tyr | |
| 625 | | | | | 630 | | | | | 635 | | | | | 640 | |
| CTC | TAT | GGC | GTC | TGT | GTC | CGC | GAC | GTG | GAG | AAT | ATC | ATG | GTG | GAA | GAG | 1968 |
| Leu | Tyr | Gly | Val | Cys | Val | Arg | Asp | Val | Glu | Asn | Ile | Met | Val | Glu | Glu | |
| | | | | 645 | | | | | 650 | | | | | 655 | | |
| TTT | GTG | GAA | GGG | GGT | CCT | CTG | GAT | CTC | TTC | ATG | CAC | CGG | AAA | AGT | GAT | 2016 |
| Phe | Val | Glu | Gly | Gly | Pro | Leu | Asp | Leu | Phe | Met | His | Arg | Lys | Ser | Asp | |
| | | | 660 | | | | | 665 | | | | | 670 | | | |
| GTC | CTT | ACC | ACA | CCA | TGG | AAA | TTC | AAA | GTT | GCC | AAA | CAG | CTG | GCC | AGT | 2064 |
| Val | Leu | Thr | Thr | Pro | Trp | Lys | Phe | Lys | Val | Ala | Lys | Gln | Leu | Ala | Ser | |
| | | 675 | | | | | 680 | | | | | 685 | | | | |
| GCC | CTG | AGC | TAC | TTG | GAG | GAT | AAA | GAC | CTG | GTC | CAT | GGA | AAT | GTG | TGT | 2112 |
| Ala | Leu | Ser | Tyr | Leu | Glu | Asp | Lys | Asp | Leu | Val | His | Gly | Asn | Val | Cys | |
| | 690 | | | | | 695 | | | | | 700 | | | | | |
| ACT | AAA | AAC | CTC | CTC | CTG | GCC | CGT | GAG | GGA | ATC | GAC | AGT | GAG | TGT | GGC | 2160 |
| Thr | Lys | Asn | Leu | Leu | Leu | Ala | Arg | Glu | Gly | Ile | Asp | Ser | Glu | Cys | Gly | |
| 705 | | | | | 710 | | | | | 715 | | | | | 720 | |
| CCA | TTC | ATC | AAG | CTC | AGT | GAC | CCC | GGC | ATC | CCC | ATT | ACG | GTG | CTG | TCT | 2208 |
| Pro | Phe | Ile | Lys | Leu | Ser | Asp | Pro | Gly | Ile | Pro | Ile | Thr | Val | Leu | Ser | |
| | | | | 725 | | | | | 730 | | | | | 735 | | |
| AGG | CAA | GAA | TGC | ATT | GAA | CGA | ATC | CCA | TGG | ATT | GCT | CCT | GAG | TGT | GTT | 2256 |
| Arg | Gln | Glu | Cys | Ile | Glu | Arg | Ile | Pro | Trp | Ile | Ala | Pro | Glu | Cys | Val | |
| | | | 740 | | | | | 745 | | | | | 750 | | | |
| GAG | GAC | TCC | AAG | AAC | CTG | AGT | GTG | GCT | GCT | GAC | AAG | TGG | AGC | TTT | GGA | 2304 |
| Glu | Asp | Ser | Lys | Asn | Leu | Ser | Val | Ala | Ala | Asp | Lys | Trp | Ser | Phe | Gly | |
| | | 755 | | | | | 760 | | | | | 765 | | | | |
| ACC | ACG | CTC | TGG | GAA | ATC | TGC | TAC | AAT | GGC | GAG | ATC | CCC | TTG | AAA | GAC | 2352 |
| Thr | Thr | Leu | Trp | Glu | Ile | Cys | Tyr | Asn | Gly | Glu | Ile | Pro | Leu | Lys | Asp | |
| | 770 | | | | | 775 | | | | | 780 | | | | | |
| AAG | ACG | CTG | ATT | GAG | AAA | GAG | AGA | TTC | TAT | GAA | AGC | CGG | TGC | AGG | CCA | 2400 |
| Lys | Thr | Leu | Ile | Glu | Lys | Glu | Arg | Phe | Tyr | Glu | Ser | Arg | Cys | Arg | Pro | |
| 785 | | | | | 790 | | | | | 795 | | | | | 800 | |
| GTG | ACA | CCA | TCA | TGT | AAG | GAG | CTG | GCT | GAC | CTC | ATG | ACC | CGC | TGC | ATG | 2448 |
| Val | Thr | Pro | Ser | Cys | Lys | Glu | Leu | Ala | Asp | Leu | Met | Thr | Arg | Cys | Met | |
| | | | | 805 | | | | | 810 | | | | | 815 | | |
| AAC | TAT | GAC | CCC | AAT | CAG | AGG | CCT | TTC | TTC | CGA | GCC | ATC | ATG | AGA | GAC | 2496 |
| Asn | Tyr | Asp | Pro | Asn | Gln | Arg | Pro | Phe | Phe | Arg | Ala | Ile | Met | Arg | Asp | |
| | | | 820 | | | | | 825 | | | | | 830 | | | |
| ATT | AAT | AAG | CTT | GAA | GAG | CAG | AAT | CCA | GAT | ATT | GTT | TCC | AGA | AAA | AAA | 2544 |
| Ile | Asn | Lys | Leu | Glu | Glu | Gln | Asn | Pro | Asp | Ile | Val | Ser | Arg | Lys | Lys | |
| | | 835 | | | | | 840 | | | | | 845 | | | | |
| AAC | CAG | CCA | ACT | GAA | GTG | GAC | CCC | ACA | CAT | TTT | GAG | AAG | CGC | TTC | CTA | 2592 |
| Asn | Gln | Pro | Thr | Glu | Val | Asp | Pro | Thr | His | Phe | Glu | Lys | Arg | Phe | Leu | |
| | 850 | | | | | 855 | | | | | 860 | | | | | |
| AAG | AGG | ATC | CGT | GAC | TTG | GGA | GAG | GGC | CAC | TTT | GGG | AAG | GTT | GAG | CTC | 2640 |
| Lys | Arg | Ile | Arg | Asp | Leu | Gly | Glu | Gly | His | Phe | Gly | Lys | Val | Glu | Leu | |
| 865 | | | | | 870 | | | | | 875 | | | | | 880 | |
| TGC | AGG | TAT | GAC | CCC | GAA | GAC | AAT | ACA | GGG | GAG | CAG | GTG | GCT | GTT | AAA | 2688 |
| Cys | Arg | Tyr | Asp | Pro | Glu | Asp | Asn | Thr | Gly | Glu | Gln | Val | Ala | Val | Lys | |
| | | | | 885 | | | | | 890 | | | | | 895 | | |
| TCT | CTG | AAG | CCT | GAG | AGT | GGA | GGT | AAC | CAC | ATA | GCT | GAT | CTG | AAA | AAG | 2736 |
| Ser | Leu | Lys | Pro | Glu | Ser | Gly | Gly | Asn | His | Ile | Ala | Asp | Leu | Lys | Lys | |
| | | | | 900 | | | | | 905 | | | | | 910 | | |

| | | | | | | | | | | | | | | | | |
|---|---|---|---|---|---|---|---|---|---|---|---|---|---|---|---|---|
| GAA | ATC | GAG | ATC | TTA | AGG | AAC | CTC | TAT | CAT | GAG | AAC | ATT | GTG | AAG | TAC | 2784 |
| Glu | Ile | Glu | Ile | Leu | Arg | Asn | Leu | Tyr | His | Glu | Asn | Ile | Val | Lys | Tyr | |
| | | 915 | | | | | 920 | | | | | 925 | | | | |
| AAA | GGA | ATC | TGC | ACA | GAA | GAC | GGA | GGA | AAT | GGT | ATT | AAG | CTC | ATC | ATG | 2832 |
| Lys | Gly | Ile | Cys | Thr | Glu | Asp | Gly | Gly | Asn | Gly | Ile | Lys | Leu | Ile | Met | |
| | | 930 | | | | 935 | | | | | 940 | | | | | |
| GAA | TTT | CTG | CCT | TCG | GGA | AGC | CTT | AAG | GAA | TAT | CTT | CCA | AAG | AAT | AAG | 2880 |
| Glu | Phe | Leu | Pro | Ser | Gly | Ser | Leu | Lys | Glu | Tyr | Leu | Pro | Lys | Asn | Lys | |
| 945 | | | | | 950 | | | | | 955 | | | | | 960 | |
| AAC | AAA | ATA | AAC | CTC | AAA | CAG | CAG | CTA | AAA | TAT | GCC | GTT | CAG | ATT | TGT | 2928 |
| Asn | Lys | Ile | Asn | Leu | Lys | Gln | Gln | Leu | Lys | Tyr | Ala | Val | Gln | Ile | Cys | |
| | | | | 965 | | | | | 970 | | | | | 975 | | |
| AAG | GGG | ATG | GAC | TAT | TTG | GGT | TCT | CGG | CAA | TAC | GTT | CAC | CGG | GAC | TTG | 2976 |
| Lys | Gly | Met | Asp | Tyr | Leu | Gly | Ser | Arg | Gln | Tyr | Val | His | Arg | Asp | Leu | |
| | | | 980 | | | | | 985 | | | | | 990 | | | |
| GCA | GCA | AGA | AAT | GTC | CTT | GTT | GAG | AGT | GAA | CAC | CAA | GTG | AAA | ATT | GGA | 3024 |
| Ala | Ala | Arg | Asn | Val | Leu | Val | Glu | Ser | Glu | His | Gln | Val | Lys | Ile | Gly | |
| | | 995 | | | | | 1000 | | | | | 1005 | | | | |
| GAC | TTC | GGT | TTA | ACC | AAA | GCA | ATT | GAA | ACC | GAT | AAG | GAG | TAT | TAC | ACC | 3072 |
| Asp | Phe | Gly | Leu | Thr | Lys | Ala | Ile | Glu | Thr | Asp | Lys | Glu | Tyr | Tyr | Thr | |
| | | 1010 | | | | 1015 | | | | | 1020 | | | | | |
| GTC | AAG | GAT | GAC | CGG | GAC | AGC | CCT | GTG | TTT | TGG | TAT | GCT | CCA | GAA | TGT | 3120 |
| Val | Lys | Asp | Asp | Arg | Asp | Ser | Pro | Val | Phe | Trp | Tyr | Ala | Pro | Glu | Cys | |
| 1025 | | | | | 1030 | | | | | 1035 | | | | | 1040 | |
| TTA | ATG | CAA | TCT | AAA | TTT | TAT | ATT | GCC | TCT | GAC | GTC | TGG | TCT | TTT | GGA | 3168 |
| Leu | Met | Gln | Ser | Lys | Phe | Tyr | Ile | Ala | Ser | Asp | Val | Trp | Ser | Phe | Gly | |
| | | | | 1045 | | | | | 1050 | | | | | 1055 | | |
| GTC | ACT | CTG | CAT | GAG | CTG | CTG | ACT | TAC | TGT | GAT | TCA | GAT | TCT | AGT | CCC | 3216 |
| Val | Thr | Leu | His | Glu | Leu | Leu | Thr | Tyr | Cys | Asp | Ser | Asp | Ser | Ser | Pro | |
| | | | 1060 | | | | | 1065 | | | | | 1070 | | | |
| ATG | GCT | TTG | TTC | CTG | AAA | ATG | ATA | GGC | CCA | ACC | CAT | GGC | CAG | ATG | ACA | 3264 |
| Met | Ala | Leu | Phe | Leu | Lys | Met | Ile | Gly | Pro | Thr | His | Gly | Gln | Met | Thr | |
| | | | | 1075 | | | | 1080 | | | | | 1085 | | | |
| GTC | ACA | AGA | CTT | GTG | AAT | ACG | TTA | AAA | GAA | GGA | AAA | CGC | CTG | CCG | TGC | 3312 |
| Val | Thr | Arg | Leu | Val | Asn | Thr | Leu | Lys | Glu | Gly | Lys | Arg | Leu | Pro | Cys | |
| | | 1090 | | | | | 1095 | | | | | 1100 | | | | |
| CCA | CCT | AAC | TGT | CCA | GAT | GAG | GTT | TAT | CAG | CTT | ATG | AGA | AAA | TGC | TGG | 3360 |
| Pro | Pro | Asn | Cys | Pro | Asp | Glu | Val | Tyr | Gln | Leu | Met | Arg | Lys | Cys | Trp | |
| 1105 | | | | | 1110 | | | | | 1115 | | | | | 1120 | |
| GAA | TTC | CAA | CCA | TCC | AAT | CGG | ACA | AGC | TTT | CAG | AAC | CTT | ATT | GAA | GGA | 3408 |
| Glu | Phe | Gln | Pro | Ser | Asn | Arg | Thr | Ser | Phe | Gln | Asn | Leu | Ile | Glu | Gly | |
| | | | | 1125 | | | | | 1130 | | | | | 1135 | | |
| TTT | GAA | GCA | CTT | TTA | AAA | TAA | | | | | | | | | | 3429 |
| Phe | Glu | Ala | Leu | Leu | Lys | | | | | | | | | | | |
| | | | 1140 | | | | | | | | | | | | | |

( 2 ) INFORMATION FOR SEQ ID NO:11:

( i ) SEQUENCE CHARACTERISTICS:
( A ) LENGTH: 1142 amino acids
( B ) TYPE: amino acid
( D ) TOPOLOGY: linear ( i i ) MOLECULE TYPE: protein ( x i ) SEQUENCE DESCRIPTION: SEQ ID NO:11:

| | | | | | | | | | | | | | | |
|---|---|---|---|---|---|---|---|---|---|---|---|---|---|---|
| Met | Ala | Phe | Cys | Ala | Lys | Met | Arg | Ser | Ser | Lys | Lys | Thr | Glu | Val | Asn |
| 1 | | | | 5 | | | | | 10 | | | | | 15 | |
| Leu | Glu | Ala | Pro | Glu | Pro | Gly | Val | Glu | Val | Ile | Phe | Tyr | Leu | Ser | Asp |
| | | | 20 | | | | | 25 | | | | | 30 | | |
| Arg | Glu | Pro | Leu | Arg | Leu | Gly | Ser | Gly | Glu | Tyr | Thr | Ala | Glu | Glu | Leu |
| | | 35 | | | | | 40 | | | | | 45 | | | |

```
Cys Ile Arg Ala Ala Gln Ala Cys Arg Ile Ser Pro Leu Cys His Asn
     50                  55                  60

Leu Phe Ala Leu Tyr Asp Glu Asn Thr Lys Leu Trp Tyr Ala Pro Asn
65                  70                  75                  80

Arg Thr Ile Thr Val Asp Asp Lys Met Ser Leu Arg Leu His Tyr Arg
             85                  90                  95

Met Arg Phe Tyr Phe Thr Asn Trp His Gly Thr Asn Asp Asn Glu Gln
             100                 105                 110

Ser Val Trp Arg His Ser Pro Lys Lys Gln Lys Asn Gly Tyr Glu Lys
         115                 120                 125

Lys Lys Ile Pro Asp Ala Thr Pro Leu Leu Asp Ala Ser Ser Leu Glu
     130                 135                 140

Tyr Leu Phe Ala Gln Gly Gln Tyr Asp Leu Val Lys Cys Leu Ala Pro
145                 150                 155                 160

Ile Arg Asp Pro Lys Thr Glu Gln Asp Gly His Asp Ile Glu Asn Glu
             165                 170                 175

Cys Leu Gly Met Ala Val Leu Ala Ile Ser His Tyr Ala Met Met Lys
             180                 185                 190

Lys Met Gln Leu Pro Glu Leu Pro Lys Asp Ile Ser Tyr Lys Arg Tyr
         195                 200                 205

Ile Pro Glu Thr Leu Asn Lys Ser Ile Arg Gln Arg Asn Leu Leu Thr
     210                 215                 220

Arg Met Arg Ile Asn Asn Val Phe Lys Asp Phe Leu Lys Glu Phe Asn
225                 230                 235                 240

Asn Lys Thr Ile Cys Asp Ser Ser Val Ser Thr His Asp Leu Lys Val
             245                 250                 255

Lys Tyr Leu Ala Thr Leu Glu Thr Leu Thr Lys His Tyr Gly Ala Glu
         260                 265                 270

Ile Phe Glu Thr Ser Met Leu Leu Ile Ser Ser Glu Asn Glu Met Asn
     275                 280                 285

Trp Phe His Ser Asn Asp Gly Gly Asn Val Leu Tyr Tyr Glu Val Met
     290                 295                 300

Val Thr Gly Asn Leu Gly Ile Gln Trp Arg His Lys Pro Asn Val Val
305                 310                 315                 320

Ser Val Glu Lys Glu Lys Asn Lys Leu Lys Arg Lys Lys Leu Glu Asn
             325                 330                 335

Lys Asp Lys Lys Asp Glu Glu Lys Asn Lys Ile Arg Glu Glu Trp Asn
         340                 345                 350

Asn Phe Ser Phe Phe Pro Glu Ile Thr His Ile Val Ile Lys Glu Ser
     355                 360                 365

Val Val Ser Ile Asn Lys Gln Asp Asn Lys Lys Met Glu Leu Lys Leu
370                 375                 380

Ser Ser His Glu Glu Ala Leu Ser Phe Val Ser Leu Val Asp Gly Tyr
385                 390                 395                 400

Phe Arg Leu Thr Ala Asp Ala His His Tyr Leu Cys Thr Asp Val Ala
             405                 410                 415

Pro Pro Leu Ile Val His Asn Ile Gln Asn Gly Cys His Gly Pro Ile
             420                 425                 430

Cys Thr Glu Tyr Ala Ile Asn Lys Leu Arg Gln Glu Gly Ser Glu Glu
         435                 440                 445

Gly Met Tyr Val Leu Arg Trp Ser Cys Thr Asp Phe Asp Asn Ile Leu
     450                 455                 460

Met Thr Val Thr Cys Phe Glu Lys Ser Glu Gln Val Gln Gly Ala Gln
```

-continued

```
465                    470                      475                    480
Lys Gln Phe Lys Asn Phe Gln Ile Glu Val Gln Lys Gly Arg Tyr Ser
                485                      490                    495
Leu His Gly Ser Asp Arg Ser Phe Pro Ser Leu Gly Asp Leu Met Ser
                500                      505                    510
His Leu Lys Lys Gln Ile Leu Arg Thr Asp Asn Ile Ser Phe Met Leu
            515                      520                    525
Lys Arg Cys Cys Gln Pro Lys Pro Arg Glu Ile Ser Asn Leu Leu Val
        530                      535                    540
Ala Thr Lys Lys Ala Gln Glu Trp Gln Pro Val Tyr Pro Met Ser Gln
545                      550                      555                    560
Leu Ser Phe Asp Arg Ile Leu Lys Lys Asp Leu Val Gln Gly Glu His
                565                      570                    575
Leu Gly Arg Gly Thr Arg Thr His Ile Tyr Ser Gly Thr Leu Met Asp
                580                      585                    590
Tyr Lys Asp Asp Glu Gly Thr Ser Glu Glu Lys Lys Ile Lys Val Ile
            595                      600                    605
Leu Lys Val Leu Asp Pro Ser His Arg Asp Ile Ser Leu Ala Phe Phe
        610                      615                    620
Glu Ala Ala Ser Met Met Arg Gln Val Ser His Lys His Ile Val Tyr
625                      630                      635                    640
Leu Tyr Gly Val Cys Val Arg Asp Val Glu Asn Ile Met Val Glu Glu
                645                      650                    655
Phe Val Glu Gly Gly Pro Leu Asp Leu Phe Met His Arg Lys Ser Asp
            660                      665                    670
Val Leu Thr Thr Pro Trp Lys Phe Lys Val Ala Lys Gln Leu Ala Ser
            675                      680                    685
Ala Leu Ser Tyr Leu Glu Asp Lys Asp Leu Val His Gly Asn Val Cys
            690                      695                    700
Thr Lys Asn Leu Leu Leu Ala Arg Glu Gly Ile Asp Ser Glu Cys Gly
705                      710                      715                    720
Pro Phe Ile Lys Leu Ser Asp Pro Gly Ile Pro Ile Thr Val Leu Ser
                725                      730                    735
Arg Gln Glu Cys Ile Glu Arg Ile Pro Trp Ile Ala Pro Glu Cys Val
            740                      745                    750
Glu Asp Ser Lys Asn Leu Ser Val Ala Ala Asp Lys Trp Ser Phe Gly
            755                      760                    765
Thr Thr Leu Trp Glu Ile Cys Tyr Asn Gly Glu Ile Pro Leu Lys Asp
770                      775                      780
Lys Thr Leu Ile Glu Lys Glu Arg Phe Tyr Glu Ser Arg Cys Arg Pro
785                      790                      795                    800
Val Thr Pro Ser Cys Lys Glu Leu Ala Asp Leu Met Thr Arg Cys Met
                805                      810                    815
Asn Tyr Asp Pro Asn Gln Arg Pro Phe Phe Arg Ala Ile Met Arg Asp
            820                      825                    830
Ile Asn Lys Leu Glu Glu Gln Asn Pro Asp Ile Val Ser Arg Lys Lys
        835                      840                    845
Asn Gln Pro Thr Glu Val Asp Pro Thr His Phe Glu Lys Arg Phe Leu
850                      855                      860
Lys Arg Ile Arg Asp Leu Gly Glu Gly His Phe Gly Lys Val Glu Leu
865                      870                      875                    880
Cys Arg Tyr Asp Pro Glu Asp Asn Thr Gly Glu Gln Val Ala Val Lys
                885                      890                    895
```

| | | | | | | | | | | | | | | | |
|---|---|---|---|---|---|---|---|---|---|---|---|---|---|---|---|
|Ser|Leu|Lys|Pro<br>900|Glu|Ser|Gly|Gly|Asn<br>905|His|Ile|Ala|Asp|Leu<br>910|Lys|Lys|
|Glu|Ile|Glu<br>915|Ile|Leu|Arg|Asn|Leu<br>920|Tyr|His|Glu|Asn|Ile<br>925|Val|Lys|Tyr|
|Lys|Gly<br>930|Ile|Cys|Thr|Glu|Asp<br>935|Gly|Gly|Asn|Gly|Ile<br>940|Lys|Leu|Ile|Met|
|Glu<br>945|Phe|Leu|Pro|Ser|Gly<br>950|Ser|Leu|Lys|Glu|Tyr<br>955|Leu|Pro|Lys|Asn|Lys<br>960|
|Asn|Lys|Ile|Asn|Leu<br>965|Lys|Gln|Gln|Leu|Lys<br>970|Tyr|Ala|Val|Gln|Ile<br>975|Cys|
|Lys|Gly|Met|Asp<br>980|Tyr|Leu|Gly|Ser|Arg<br>985|Gln|Tyr|Val|His|Arg<br>990|Asp|Leu|
|Ala|Ala|Arg<br>995|Asn|Val|Leu|Val|Glu<br>1000|Ser|Glu|His|Gln|Val<br>1005|Lys|Ile|Gly|
|Asp|Phe<br>1010|Gly|Leu|Thr|Lys|Ala<br>1015|Ile|Glu|Thr|Asp|Lys<br>1020|Glu|Tyr|Tyr|Thr|
|Val<br>1025|Lys|Asp|Asp|Arg|Asp<br>1030|Ser|Pro|Val|Phe|Trp<br>1035|Tyr|Ala|Pro|Glu|Cys<br>1040|
|Leu|Met|Gln|Ser|Lys<br>1045|Phe|Tyr|Ile|Ala|Ser<br>1050|Asp|Val|Trp|Ser|Phe<br>1055|Gly|
|Val|Thr|Leu|His<br>1060|Glu|Leu|Leu|Thr|Tyr<br>1065|Cys|Asp|Ser|Asp|Ser<br>1070|Ser|Pro|
|Met|Ala|Leu|Phe<br>1075|Leu|Lys|Met|Ile|Gly<br>1080|Pro|Thr|His|Gly|Gln<br>1085|Met|Thr|
|Val|Thr|Arg<br>1090|Leu|Val|Asn|Thr|Leu<br>1095|Lys|Glu|Gly|Lys|Arg<br>1100|Leu|Pro|Cys|
|Pro<br>1105|Pro|Asn|Cys|Pro|Asp<br>1110|Glu|Val|Tyr|Gln|Leu<br>1115|Met|Arg|Lys|Cys|Trp<br>1120|
|Glu|Phe|Gln|Pro|Ser<br>1125|Asn|Arg|Thr|Ser|Phe<br>1130|Gln|Asn|Leu|Ile|Glu<br>1135|Gly|
|Phe|Glu|Ala|Leu<br>1140|Leu|Lys| | | | | | | | | | |

( 2 ) INFORMATION FOR SEQ ID NO:12:

( i ) SEQUENCE CHARACTERISTICS:
        ( A ) LENGTH: 3561 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..3561

( x i ) SEQUENCE DESCRIPTION: SEQ ID NO:12:

| | | | | | | | | | | | | | | | |
|---|---|---|---|---|---|---|---|---|---|---|---|---|---|---|---|
|ATG<br>Met<br>1|CCT<br>Pro|CTG<br>Leu|CGC<br>Arg|CAC<br>His<br>5|TGG<br>Trp|GGG<br>Gly|ATG<br>Met|GCC<br>Ala|AGG<br>Arg<br>10|GGC<br>Gly|AGT<br>Ser|AAG<br>Lys|CCC<br>Pro|GTT<br>Val<br>15|GGG<br>Gly|48|
|GAT<br>Asp|GGA<br>Gly|GCC<br>Ala|CAG<br>Gln<br>20|CCC<br>Pro|ATG<br>Met|GCT<br>Ala|GCC<br>Ala|ATG<br>Met<br>25|GGA<br>Gly|GGC<br>Gly|CTG<br>Leu|AAG<br>Lys|GTG<br>Val<br>30|CTT<br>Leu|CTG<br>Leu|96|
|CAC<br>His|TGG<br>Trp|GCT<br>Ala<br>35|GGT<br>Gly|CCA<br>Pro|GGC<br>Gly|GGC<br>Gly|GGG<br>Gly<br>40|GAG<br>Glu|CCC<br>Pro|TGG<br>Trp|GTC<br>Val|ACT<br>Thr<br>45|TTC<br>Phe|AGT<br>Ser|GAG<br>Glu|144|
|TCA<br>Ser|TCG<br>Ser<br>50|CTG<br>Leu|ACA<br>Thr|GCT<br>Ala|GAG<br>Glu|GAA<br>Glu<br>55|GTC<br>Val|TGC<br>Cys|ATC<br>Ile|CAC<br>His|ATT<br>Ile<br>60|GCA<br>Ala|CAT<br>His|AAA<br>Lys|GTT<br>Val|192|
|GGT<br>Gly|ATC<br>Ile|ACT<br>Thr|CCT<br>Pro|CCT<br>Pro|TGC<br>Cys|TTC<br>Phe|AAT<br>Asn|CTC<br>Leu|TTT<br>Phe|GCC<br>Ala|CTC<br>Leu|TTC<br>Phe|GAT<br>Asp|GCT<br>Ala|CAG<br>Gln|240|

```
Gly Ile Thr Pro Pro Cys Phe Asn Leu Phe Ala Leu Phe Asp Ala Gln
 65              70                  75                  80

GCC CAA GTC TGG TTG CCC CCA AAC CAC ATC CTA GAG ATC CCC AGA GAT      288
Ala Gln Val Trp Leu Pro Pro Asn His Ile Leu Glu Ile Pro Arg Asp
             85                  90                  95

GCA AGC CTG ATG CTA TAT TTC CGC ATA AGG TTT TAT TTC CGG AAC TGG      336
Ala Ser Leu Met Leu Tyr Phe Arg Ile Arg Phe Tyr Phe Arg Asn Trp
            100                 105                 110

CAT GGC ATG AAT CCT CGG GAA CCG GCT GTG TAC CGT TGT GGG CCC CCA      384
His Gly Met Asn Pro Arg Glu Pro Ala Val Tyr Arg Cys Gly Pro Pro
            115                 120                 125

GGA ACC GAG GCA TCC TCA GAT CAG ACA GCA CAG GGG ATG CAA CTC CTG      432
Gly Thr Glu Ala Ser Ser Asp Gln Thr Ala Gln Gly Met Gln Leu Leu
        130                 135                 140

GAC CCA GCC TCA TTT GAG TAC CTC TTT GAG CAG GGC AAG CAT GAG TTT      480
Asp Pro Ala Ser Phe Glu Tyr Leu Phe Glu Gln Gly Lys His Glu Phe
145                 150                 155                 160

GTG AAT GAC GTG GCA TCA CTG TGG GAG CTG TCG ACC GAG GAG GAG ATC      528
Val Asn Asp Val Ala Ser Leu Trp Glu Leu Ser Thr Glu Glu Glu Ile
                165                 170                 175

CAC CAC TTT AAG AAT GAG AGC CTG GGC ATG GCC TTT CTG CAC CTC TGT      576
His His Phe Lys Asn Glu Ser Leu Gly Met Ala Phe Leu His Leu Cys
            180                 185                 190

CAC CTC GCT CTC CGC CAT GGC ATC CCC CTG GAG GAG GTG GCC AAG AAG      624
His Leu Ala Leu Arg His Gly Ile Pro Leu Glu Glu Val Ala Lys Lys
            195                 200                 205

ACC AGC TTC AAG GAC TGC ATC CCG CGC TCC TTC CGC CGG CAT ATC CGG      672
Thr Ser Phe Lys Asp Cys Ile Pro Arg Ser Phe Arg Arg His Ile Arg
        210                 215                 220

CAG CAC AGC GCC CTG ACC CGG CTG CGC CTT CGG AAC GTC TTC CGC AGG      720
Gln His Ser Ala Leu Thr Arg Leu Arg Leu Arg Asn Val Phe Arg Arg
225                 230                 235                 240

TTC CTG CGG GAC TTC CAG CCG GGC CGA CTC TCC CAG CAG ATG GTC ATG      768
Phe Leu Arg Asp Phe Gln Pro Gly Arg Leu Ser Gln Gln Met Val Met
                245                 250                 255

GTC AAA TAC CTA GCC ACA CTC GAG CGG CTG GCA CCC CGC TTC GGC ACA      816
Val Lys Tyr Leu Ala Thr Leu Glu Arg Leu Ala Pro Arg Phe Gly Thr
            260                 265                 270

GAG CGT GTG CCC GTG TGC CAC CTG AGG CTG CTG GCC CAG GCC GAG GGG      864
Glu Arg Val Pro Val Cys His Leu Arg Leu Leu Ala Gln Ala Glu Gly
            275                 280                 285

GAG CCC TGC TAC ATC CGG GAC AGT GGG GTG GCC CCT ACA GAC CCT GGC      912
Glu Pro Cys Tyr Ile Arg Asp Ser Gly Val Ala Pro Thr Asp Pro Gly
        290                 295                 300

CCT GAG TCT GCT GCT GGG CCC CCA ACC CAC GAG GTG CTG GTG ACA GGC      960
Pro Glu Ser Ala Ala Gly Pro Pro Thr His Glu Val Leu Val Thr Gly
305                 310                 315                 320

ACT GGT GGC ATC CAG TGG TGG CCA GTA GAG GAG GAG GTG AAC AAG GAG     1008
Thr Gly Gly Ile Gln Trp Trp Pro Val Glu Glu Glu Val Asn Lys Glu
                325                 330                 335

GAG GGT TCT AGT GGC AGC AGT GGC AGG AAC CCC CAA GCC AGC CTG TTT     1056
Glu Gly Ser Ser Gly Ser Ser Gly Arg Asn Pro Gln Ala Ser Leu Phe
            340                 345                 350

GGG AAG AAG GCC AAG GCT CAC AAG GCA TTC GGC CAG CCG GCA GAC AGG     1104
Gly Lys Lys Ala Lys Ala His Lys Ala Phe Gly Gln Pro Ala Asp Arg
        355                 360                 365

CCG CGG GAG CCA CTG TGG GCC TAC TTC TGT GAC TTC CGG GAC ATC ACC     1152
Pro Arg Glu Pro Leu Trp Ala Tyr Phe Cys Asp Phe Arg Asp Ile Thr
370                 375                 380

CAC GTG GTG CTG AAA GAG CAC TGT GTC AGC ATC CAC CGG CAG GAC AAC     1200
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| His | Val | Val | Leu | Lys | Glu | His | Cys | Val | Ser | Ile | His | Arg | Gln | Asp | Asn |      |
| 385 |     |     |     |     | 390 |     |     |     |     | 395 |     |     |     |     | 400 |      |
| AAG | TGC | CTG | GAG | CTG | AGC | TTG | CCT | TCC | CGG | GCT | GCG | GCG | CTG | TCC | TTC | 1248 |
| Lys | Cys | Leu | Glu | Leu | Ser | Leu | Pro | Ser | Arg | Ala | Ala | Ala | Leu | Ser | Phe |      |
|     |     |     |     | 405 |     |     |     |     | 410 |     |     |     |     | 415 |     |      |
| GTG | TCG | CTG | GTG | GAC | GGC | TAT | TTC | CGC | CTG | ACG | GCC | GAC | TCC | AGC | CAC | 1296 |
| Val | Ser | Leu | Val | Asp | Gly | Tyr | Phe | Arg | Leu | Thr | Ala | Asp | Ser | Ser | His |      |
|     |     |     | 420 |     |     |     |     | 425 |     |     |     |     | 430 |     |     |      |
| TAC | CTG | TGC | CAC | GAG | GTG | GCT | CCC | CCA | CGG | CTG | GTG | ATG | AGC | ATC | CGG | 1344 |
| Tyr | Leu | Cys | His | Glu | Val | Ala | Pro | Pro | Arg | Leu | Val | Met | Ser | Ile | Arg |      |
|     |     | 435 |     |     |     |     | 440 |     |     |     |     | 445 |     |     |     |      |
| GAT | GGG | ATC | CAC | GGA | CCC | CTG | CTG | GAG | CCA | TTT | GTG | CAG | GCC | AAG | CTG | 1392 |
| Asp | Gly | Ile | His | Gly | Pro | Leu | Leu | Glu | Pro | Phe | Val | Gln | Ala | Lys | Leu |      |
| 450 |     |     |     |     | 455 |     |     |     |     | 460 |     |     |     |     |     |      |
| CGG | CCC | GAG | GAC | GGC | CTG | TAC | CTC | ATT | CAC | TGG | AGC | ACC | AGC | CAC | CCC | 1440 |
| Arg | Pro | Glu | Asp | Gly | Leu | Tyr | Leu | Ile | His | Trp | Ser | Thr | Ser | His | Pro |      |
| 465 |     |     |     |     | 470 |     |     |     |     | 475 |     |     |     |     | 480 |      |
| TAC | CGC | CTG | ATC | CTC | ACA | GTG | GCC | CAG | CGT | AGC | CAG | GCA | CCA | GAC | GGC | 1488 |
| Tyr | Arg | Leu | Ile | Leu | Thr | Val | Ala | Gln | Arg | Ser | Gln | Ala | Pro | Asp | Gly |      |
|     |     |     |     | 485 |     |     |     |     | 490 |     |     |     |     | 495 |     |      |
| ATG | CAG | AGC | TTG | CGG | CTC | CGA | AAG | TTC | CCC | ATT | GAG | CAG | CAG | GAC | GGG | 1536 |
| Met | Gln | Ser | Leu | Arg | Leu | Arg | Lys | Phe | Pro | Ile | Glu | Gln | Gln | Asp | Gly |      |
|     |     |     | 500 |     |     |     |     | 505 |     |     |     |     | 510 |     |     |      |
| GCC | TTC | GTG | CTG | GAG | GGC | TGG | GGC | CGG | TCC | TTC | CCC | AGC | GTT | CGG | GAA | 1584 |
| Ala | Phe | Val | Leu | Glu | Gly | Trp | Gly | Arg | Ser | Phe | Pro | Ser | Val | Arg | Glu |      |
|     |     | 515 |     |     |     |     | 520 |     |     |     |     | 525 |     |     |     |      |
| CTT | GGG | GCT | GCC | TTG | CAG | GGC | TGC | TTG | CTG | AGG | GCC | GGG | GAT | GAC | TGC | 1632 |
| Leu | Gly | Ala | Ala | Leu | Gln | Gly | Cys | Leu | Leu | Arg | Ala | Gly | Asp | Asp | Cys |      |
|     | 530 |     |     |     |     | 535 |     |     |     |     | 540 |     |     |     |     |      |
| TTC | TCT | CTG | CGT | CGC | TGT | TGC | CTG | CCC | CAA | CCA | GGA | GAA | ACC | TCC | AAT | 1680 |
| Phe | Ser | Leu | Arg | Arg | Cys | Cys | Leu | Pro | Gln | Pro | Gly | Glu | Thr | Ser | Asn |      |
| 545 |     |     |     |     | 550 |     |     |     |     | 555 |     |     |     |     | 560 |      |
| CTC | ATC | ATC | ATG | CGG | GGG | GCT | CGG | GCC | AGC | CCC | AGG | ACA | CTC | AAC | CTC | 1728 |
| Leu | Ile | Ile | Met | Arg | Gly | Ala | Arg | Ala | Ser | Pro | Arg | Thr | Leu | Asn | Leu |      |
|     |     |     |     | 565 |     |     |     |     | 570 |     |     |     |     | 575 |     |      |
| AGC | CAG | CTC | AGC | TTC | CAC | CGG | GTT | GAC | CAG | AAG | GAG | ATC | ACC | CAG | CTG | 1776 |
| Ser | Gln | Leu | Ser | Phe | His | Arg | Val | Asp | Gln | Lys | Glu | Ile | Thr | Gln | Leu |      |
|     |     |     | 580 |     |     |     |     | 585 |     |     |     |     | 590 |     |     |      |
| TCC | CAC | TTG | GGC | CAG | GGC | ACA | AGG | ACC | AAC | GTG | TAT | GAG | GGC | CGC | CTG | 1824 |
| Ser | His | Leu | Gly | Gln | Gly | Thr | Arg | Thr | Asn | Val | Tyr | Glu | Gly | Arg | Leu |      |
|     |     | 595 |     |     |     |     | 600 |     |     |     |     | 605 |     |     |     |      |
| CGA | GTG | GAG | GGC | AGC | GGG | GAC | CCT | GAG | GAG | GGC | AAG | ATG | GAT | GAC | GAG | 1872 |
| Arg | Val | Glu | Gly | Ser | Gly | Asp | Pro | Glu | Glu | Gly | Lys | Met | Asp | Asp | Glu |      |
|     | 610 |     |     |     |     | 615 |     |     |     |     | 620 |     |     |     |     |      |
| GAC | CCC | CTC | GTG | CCT | GGC | AGG | GAC | CGT | GGG | CAG | GAG | CTA | CGA | GTG | GTG | 1920 |
| Asp | Pro | Leu | Val | Pro | Gly | Arg | Asp | Arg | Gly | Gln | Glu | Leu | Arg | Val | Val |      |
| 625 |     |     |     |     | 630 |     |     |     |     | 635 |     |     |     |     | 640 |      |
| CTC | AAA | GTG | CTG | GAC | CCT | AGT | CAC | CAT | GAC | ATC | GCC | CTG | GCC | TTC | TAC | 1968 |
| Leu | Lys | Val | Leu | Asp | Pro | Ser | His | His | Asp | Ile | Ala | Leu | Ala | Phe | Tyr |      |
|     |     |     |     | 645 |     |     |     |     | 650 |     |     |     |     | 655 |     |      |
| GAG | ACA | GCC | AGC | CTC | ATG | AGC | CAG | GTC | TCC | CAC | ACG | CAC | CTG | GCC | TTC | 2016 |
| Glu | Thr | Ala | Ser | Leu | Met | Ser | Gln | Val | Ser | His | Thr | His | Leu | Ala | Phe |      |
|     |     |     | 660 |     |     |     |     | 665 |     |     |     |     | 670 |     |     |      |
| GTG | CAT | GGC | GTC | TGT | GTG | CGC | GGC | CCT | GAA | AAT | AGC | ATG | GTG | ACA | GAG | 2064 |
| Val | His | Gly | Val | Cys | Val | Arg | Gly | Pro | Glu | Asn | Ser | Met | Val | Thr | Glu |      |
|     |     | 675 |     |     |     |     | 680 |     |     |     |     | 685 |     |     |     |      |
| TAC | GTG | GAG | CAC | GGA | CCC | CTG | GAT | GTG | TGG | CTG | CGG | AGG | GAG | CGG | GGC | 2112 |
| Tyr | Val | Glu | His | Gly | Pro | Leu | Asp | Val | Trp | Leu | Arg | Arg | Glu | Arg | Gly |      |
|     | 690 |     |     |     |     | 695 |     |     |     |     | 700 |     |     |     |     |      |
| CAT | GTG | CCC | ATG | GCT | TGG | AAG | ATG | GTG | GTG | GCC | CAG | CAG | CTG | GCC | AGC | 2160 |

|   |   |   |   |   |   |   |   |   |   |   |   |   |   |   |   |   |
|---|---|---|---|---|---|---|---|---|---|---|---|---|---|---|---|---|
| His | Val | Pro | Met | Ala | Trp | Lys | Met | Val | Val | Ala | Gln | Gln | Leu | Ala | Ser | |
| 705 | | | | | 710 | | | | | 715 | | | | | 720 | |
| GCC | CTC | AGC | TAC | CTG | GAG | AAC | AAG | AAC | CTG | GTT | CAT | GGT | AAT | GTG | TGT | 2208 |
| Ala | Leu | Ser | Tyr | Leu | Glu | Asn | Lys | Asn | Leu | Val | His | Gly | Asn | Val | Cys | |
| | | | | 725 | | | | | 730 | | | | | 735 | | |
| GGC | CGG | AAC | ATC | CTG | CTG | GCC | CGG | CTG | GGG | TTG | GCA | GAG | GGC | ACC | AGC | 2256 |
| Gly | Arg | Asn | Ile | Leu | Leu | Ala | Arg | Leu | Gly | Leu | Ala | Glu | Gly | Thr | Ser | |
| | | | 740 | | | | | 745 | | | | | | 750 | | |
| CCC | TTC | ATC | AAG | CTG | AGT | GAT | CCT | GGC | GTG | GGC | CTG | GGC | GCC | CTC | TCC | 2304 |
| Pro | Phe | Ile | Lys | Leu | Ser | Asp | Pro | Gly | Val | Gly | Leu | Gly | Ala | Leu | Ser | |
| | | 755 | | | | | 760 | | | | | 765 | | | | |
| AGG | GAG | GAG | CGG | GTG | GAG | AGG | ATC | CCC | TGG | CTG | GCC | CCC | GAA | TGC | CTA | 2352 |
| Arg | Glu | Glu | Arg | Val | Glu | Arg | Ile | Pro | Trp | Leu | Ala | Pro | Glu | Cys | Leu | |
| | 770 | | | | | 775 | | | | | 780 | | | | | |
| CCA | GGT | GGG | GCC | AAC | AGC | CTA | AGC | ACC | GCC | ATG | GAC | AAG | TGG | GGG | TTT | 2400 |
| Pro | Gly | Gly | Ala | Asn | Ser | Leu | Ser | Thr | Ala | Met | Asp | Lys | Trp | Gly | Phe | |
| 785 | | | | | 790 | | | | | 795 | | | | | 800 | |
| GGC | GCC | ACC | CTC | CTG | GAG | ATC | TGC | TTT | GAC | GGA | GAG | GCC | CCT | CTG | CAG | 2448 |
| Gly | Ala | Thr | Leu | Leu | Glu | Ile | Cys | Phe | Asp | Gly | Glu | Ala | Pro | Leu | Gln | |
| | | | | 805 | | | | | 810 | | | | | 815 | | |
| AGC | CGC | AGT | CCC | TCC | GAG | AAG | GAG | CAT | TTC | TAC | CAG | AGG | CAG | CAC | CGG | 2496 |
| Ser | Arg | Ser | Pro | Ser | Glu | Lys | Glu | His | Phe | Tyr | Gln | Arg | Gln | His | Arg | |
| | | | 820 | | | | | 825 | | | | | 830 | | | |
| CTG | CCC | GAG | CCC | TCC | TGC | CCA | CAG | CTG | GCC | ACA | CTC | ACC | AGC | CAG | TGT | 2544 |
| Leu | Pro | Glu | Pro | Ser | Cys | Pro | Gln | Leu | Ala | Thr | Leu | Thr | Ser | Gln | Cys | |
| | | 835 | | | | | 840 | | | | | 845 | | | | |
| CTG | ACC | TAT | GAG | CCA | ACC | CAG | AGG | CCA | TCA | TTC | CGC | ACC | ATC | CTG | CGT | 2592 |
| Leu | Thr | Tyr | Glu | Pro | Thr | Gln | Arg | Pro | Ser | Phe | Arg | Thr | Ile | Leu | Arg | |
| | 850 | | | | | 855 | | | | | 860 | | | | | |
| GAC | CTC | ACC | CGC | GTG | CAG | CCC | CAC | AAT | CTT | GCT | GAC | GTC | TTG | ACT | GTG | 2640 |
| Asp | Leu | Thr | Arg | Val | Gln | Pro | His | Asn | Leu | Ala | Asp | Val | Leu | Thr | Val | |
| 865 | | | | | 870 | | | | | 875 | | | | | 880 | |
| AAC | CGG | GAC | TCA | CCG | GCC | GTC | GGA | CCT | ACT | ACT | TTC | CAC | AAG | CGC | TAT | 2688 |
| Asn | Arg | Asp | Ser | Pro | Ala | Val | Gly | Pro | Thr | Thr | Phe | His | Lys | Arg | Tyr | |
| | | | | 885 | | | | | 890 | | | | | 895 | | |
| TTG | AAA | AAG | ATC | CGA | GAT | CTG | GGC | GAG | GGT | CAC | TTC | GGC | AAG | GTC | AGC | 2736 |
| Leu | Lys | Lys | Ile | Arg | Asp | Leu | Gly | Glu | Gly | His | Phe | Gly | Lys | Val | Ser | |
| | | | 900 | | | | | 905 | | | | | 910 | | | |
| TTG | TAC | TGC | TAC | GAT | CCG | ACC | AAC | GAC | GGC | ACT | GGC | GAG | ATG | GTG | GCG | 2784 |
| Leu | Tyr | Cys | Tyr | Asp | Pro | Thr | Asn | Asp | Gly | Thr | Gly | Glu | Met | Val | Ala | |
| | | 915 | | | | | 920 | | | | | 925 | | | | |
| GTG | AAA | GCC | CTC | AAG | GCA | GAC | TGC | GGC | CCC | CAG | CAC | CGC | TCG | GGC | TGG | 2832 |
| Val | Lys | Ala | Leu | Lys | Ala | Asp | Cys | Gly | Pro | Gln | His | Arg | Ser | Gly | Trp | |
| | 930 | | | | | 935 | | | | | 940 | | | | | |
| AAG | CAG | GAG | ATT | GAC | ATT | CTG | CGC | ACG | CTC | TAC | CAC | GAG | CAC | ATC | ATC | 2880 |
| Lys | Gln | Glu | Ile | Asp | Ile | Leu | Arg | Thr | Leu | Tyr | His | Glu | His | Ile | Ile | |
| 945 | | | | | 950 | | | | | 955 | | | | | 960 | |
| AAG | TAC | AAG | GGC | TGC | TGC | GAG | GAC | CAA | GGC | GAG | AAG | TCG | CTG | CAG | CTG | 2928 |
| Lys | Tyr | Lys | Gly | Cys | Cys | Glu | Asp | Gln | Gly | Glu | Lys | Ser | Leu | Gln | Leu | |
| | | | | 965 | | | | | 970 | | | | | 975 | | |
| GTC | ATG | GAG | TAC | GTG | CCC | CTG | GGC | AGC | CTC | CGA | GAC | TAC | CTG | CCC | CGG | 2976 |
| Val | Met | Glu | Tyr | Val | Pro | Leu | Gly | Ser | Leu | Arg | Asp | Tyr | Leu | Pro | Arg | |
| | | 980 | | | | | 985 | | | | | 990 | | | | |
| CAC | AGC | ATC | GGG | CTG | GCC | CAG | CTG | CTG | CTC | TTC | GCC | CAG | CAG | ATC | TGC | 3024 |
| His | Ser | Ile | Gly | Leu | Ala | Gln | Leu | Leu | Leu | Phe | Ala | Gln | Gln | Ile | Cys | |
| | | 995 | | | | | 1000 | | | | | 1005 | | | | |
| GAG | GGC | ATG | GCC | TAT | CTG | CAC | GCG | CAC | GAC | TAC | ATC | CAC | CGA | GAC | CTA | 3072 |
| Glu | Gly | Met | Ala | Tyr | Leu | His | Ala | His | Asp | Tyr | Ile | His | Arg | Asp | Leu | |
| | | 1010 | | | | | 1015 | | | | | 1020 | | | | |
| GCC | GCG | CGC | AAC | GTG | CTG | CTG | GAC | AAC | GAC | AGG | CTG | GTC | AAG | ATC | GGG | 3120 |

| | | | | | | | | | | | | | | | | |
|---|---|---|---|---|---|---|---|---|---|---|---|---|---|---|---|---|
|Ala|Ala|Arg|Asn|Val|Leu|Leu|Asp|Asn|Asp|Arg|Leu|Val|Lys|Ile|Gly| |
|1025| | | |1030| | | | |1035| | | | |1040| | |

```
GAC  TTT  GGC  CTA  GCC  AAG  GCC  GTG  CCC  GAA  GGC  CAC  GAG  TAC  TAC  CGC      3168
Asp  Phe  Gly  Leu  Ala  Lys  Ala  Val  Pro  Glu  Gly  His  Glu  Tyr  Tyr  Arg
               1045                         1050                    1055

GTG  CGC  GAG  GAT  GGG  GAC  AGC  CCC  GTG  TTC  TGG  TAT  GCC  CCA  GAG  TGC      3216
Val  Arg  Glu  Asp  Gly  Asp  Ser  Pro  Val  Phe  Trp  Tyr  Ala  Pro  Glu  Cys
                    1060                    1065                    1070

CTG  AAG  GAG  TAT  AAG  TTC  TAC  TAT  GCG  TCA  GAT  GTC  TGG  TCC  TTC  GGG      3264
Leu  Lys  Glu  Tyr  Lys  Phe  Tyr  Tyr  Ala  Ser  Asp  Val  Trp  Ser  Phe  Gly
          1075                    1080                    1085

GTG  ACC  CTG  TAT  GAG  CTG  CTG  ACG  CAC  TGT  GAC  TCC  AGC  CAG  AGC  CCC      3312
Val  Thr  Leu  Tyr  Glu  Leu  Leu  Thr  His  Cys  Asp  Ser  Ser  Gln  Ser  Pro
     1090                     1095                    1100

CCC  ACG  AAA  TTC  CTT  GAG  CTC  ATA  GGC  ATT  GCT  CAG  GGT  CAG  ATG  ACA      3360
Pro  Thr  Lys  Phe  Leu  Glu  Leu  Ile  Gly  Ile  Ala  Gln  Gly  Gln  Met  Thr
1105                     1110                    1115                    1120

GTT  CTG  AGA  CTC  ACT  GAG  TTG  CTG  GAA  CGA  GGG  GAG  AGG  CTG  CCA  CGG      3408
Val  Leu  Arg  Leu  Thr  Glu  Leu  Leu  Glu  Arg  Gly  Glu  Arg  Leu  Pro  Arg
                    1125                    1130                    1135

CCC  GAC  AAA  TGT  CCC  TGT  GAG  GTC  TAT  CAT  CTC  ATG  AAG  AAC  TGC  TGG      3456
Pro  Asp  Lys  Cys  Pro  Cys  Glu  Val  Tyr  His  Leu  Met  Lys  Asn  Cys  Trp
               1140                    1145                    1150

GAG  ACA  GAG  GCG  TCC  TTT  CGC  CCA  ACC  TTC  GAG  AAC  CTC  ATA  CCC  ATT      3504
Glu  Thr  Glu  Ala  Ser  Phe  Arg  Pro  Thr  Phe  Glu  Asn  Leu  Ile  Pro  Ile
          1155                    1160                    1165

CTG  AAG  ACA  GTC  CAT  GAG  AAG  TAC  CAA  GGC  CAG  GCC  CCT  TCA  GTG  TTC      3552
Leu  Lys  Thr  Val  His  Glu  Lys  Tyr  Gln  Gly  Gln  Ala  Pro  Ser  Val  Phe
     1170                    1175                    1180

AGC  GTG  TGC                                                                        3561
Ser  Val  Cys
1185
```

( 2 ) INFORMATION FOR SEQ ID NO:13:

( i ) SEQUENCE CHARACTERISTICS:
( A ) LENGTH: 1187 amino acids
( B ) TYPE: amino acid
( D ) TOPOLOGY: linear ( i i ) MOLECULE TYPE: protein ( x i ) SEQUENCE DESCRIPTION: SEQ ID NO:13:

```
Met  Pro  Leu  Arg  His  Trp  Gly  Met  Ala  Arg  Gly  Ser  Lys  Pro  Val  Gly
  1             5                    10                      15

Asp  Gly  Ala  Gln  Pro  Met  Ala  Ala  Met  Gly  Gly  Leu  Lys  Val  Leu  Leu
               20                   25                      30

His  Trp  Ala  Gly  Pro  Gly  Gly  Gly  Glu  Pro  Trp  Val  Thr  Phe  Ser  Glu
               35                   40                      45

Ser  Ser  Leu  Thr  Ala  Glu  Glu  Val  Cys  Ile  His  Ile  Ala  His  Lys  Val
     50                        55                    60

Gly  Ile  Thr  Pro  Pro  Cys  Phe  Asn  Leu  Phe  Ala  Leu  Phe  Asp  Ala  Gln
 65                      70                        75                        80

Ala  Gln  Val  Trp  Leu  Pro  Pro  Asn  His  Ile  Leu  Glu  Ile  Pro  Arg  Asp
                    85                        90                        95

Ala  Ser  Leu  Met  Leu  Tyr  Phe  Arg  Ile  Arg  Phe  Tyr  Phe  Arg  Asn  Trp
                100                      105                     110

His  Gly  Met  Asn  Pro  Arg  Glu  Pro  Ala  Val  Tyr  Arg  Cys  Gly  Pro  Pro
          115                    120                     125

Gly  Thr  Glu  Ala  Ser  Ser  Asp  Gln  Thr  Ala  Gln  Gly  Met  Gln  Leu  Leu
```

```
            130                      135                      140
Asp Pro Ala Ser Phe Glu Tyr Leu Phe Glu Gln Gly Lys His Glu Phe
145                 150                 155                 160

Val Asn Asp Val Ala Ser Leu Trp Glu Leu Ser Thr Glu Glu Glu Ile
                165                 170                 175

His His Phe Lys Asn Glu Ser Leu Gly Met Ala Phe Leu His Leu Cys
            180                 185                 190

His Leu Ala Leu Arg His Gly Ile Pro Leu Glu Glu Val Ala Lys Lys
        195                 200                 205

Thr Ser Phe Lys Asp Cys Ile Pro Arg Ser Phe Arg Arg His Ile Arg
    210                 215                 220

Gln His Ser Ala Leu Thr Arg Leu Arg Leu Arg Asn Val Phe Arg Arg
225                 230                 235                 240

Phe Leu Arg Asp Phe Gln Pro Gly Arg Leu Ser Gln Gln Met Val Met
                245                 250                 255

Val Lys Tyr Leu Ala Thr Leu Glu Arg Leu Ala Pro Arg Phe Gly Thr
                260                 265                 270

Glu Arg Val Pro Val Cys His Leu Arg Leu Leu Ala Gln Ala Glu Gly
            275                 280                 285

Glu Pro Cys Tyr Ile Arg Asp Ser Gly Val Ala Pro Thr Asp Pro Gly
290                 295                 300

Pro Glu Ser Ala Ala Gly Pro Pro Thr His Glu Val Leu Val Thr Gly
305                 310                 315                 320

Thr Gly Gly Ile Gln Trp Trp Pro Val Glu Glu Val Asn Lys Glu
                325                 330                 335

Glu Gly Ser Ser Gly Ser Ser Gly Arg Asn Pro Gln Ala Ser Leu Phe
            340                 345                 350

Gly Lys Lys Ala Lys Ala His Lys Ala Phe Gly Gln Pro Ala Asp Arg
        355                 360                 365

Pro Arg Glu Pro Leu Trp Ala Tyr Phe Cys Asp Phe Arg Asp Ile Thr
    370                 375                 380

His Val Val Leu Lys Glu His Cys Val Ser Ile His Arg Gln Asp Asn
385                 390                 395                 400

Lys Cys Leu Glu Leu Ser Leu Pro Ser Arg Ala Ala Ala Leu Ser Phe
                405                 410                 415

Val Ser Leu Val Asp Gly Tyr Phe Arg Leu Thr Ala Asp Ser Ser His
                420                 425                 430

Tyr Leu Cys His Glu Val Ala Pro Arg Leu Val Met Ser Ile Arg
            435                 440                 445

Asp Gly Ile His Gly Pro Leu Leu Glu Pro Phe Val Gln Ala Lys Leu
    450                 455                 460

Arg Pro Glu Asp Gly Leu Tyr Leu Ile His Trp Ser Thr Ser His Pro
465                 470                 475                 480

Tyr Arg Leu Ile Leu Thr Val Ala Gln Arg Ser Gln Ala Pro Asp Gly
                485                 490                 495

Met Gln Ser Leu Arg Leu Arg Lys Phe Pro Ile Glu Gln Gln Asp Gly
            500                 505                 510

Ala Phe Val Leu Glu Gly Trp Gly Arg Ser Phe Pro Ser Val Arg Glu
        515                 520                 525

Leu Gly Ala Ala Leu Gln Gly Cys Leu Leu Arg Ala Gly Asp Asp Cys
    530                 535                 540

Phe Ser Leu Arg Arg Cys Cys Leu Pro Gln Pro Gly Glu Thr Ser Asn
545                 550                 555                 560
```

```
Leu Ile Ile Met Arg Gly Ala Arg Ala Ser Pro Arg Thr Leu Asn Leu
            565             570             575

Ser Gln Leu Ser Phe His Arg Val Asp Gln Lys Glu Ile Thr Gln Leu
        580             585             590

Ser His Leu Gly Gln Gly Thr Arg Thr Asn Val Tyr Glu Gly Arg Leu
        595             600             605

Arg Val Glu Gly Ser Gly Asp Pro Glu Glu Gly Lys Met Asp Asp Glu
    610             615             620

Asp Pro Leu Val Pro Gly Arg Asp Arg Gly Gln Glu Leu Arg Val Val
625             630             635             640

Leu Lys Val Leu Asp Pro Ser His His Asp Ile Ala Leu Ala Phe Tyr
                645             650             655

Glu Thr Ala Ser Leu Met Ser Gln Val Ser His Thr His Leu Ala Phe
            660             665             670

Val His Gly Val Cys Val Arg Gly Pro Glu Asn Ser Met Val Thr Glu
    675             680             685

Tyr Val Glu His Gly Pro Leu Asp Val Trp Leu Arg Arg Glu Arg Gly
    690             695             700

His Val Pro Met Ala Trp Lys Met Val Val Ala Gln Gln Leu Ala Ser
705             710             715             720

Ala Leu Ser Tyr Leu Glu Asn Lys Asn Leu Val His Gly Asn Val Cys
                725             730             735

Gly Arg Asn Ile Leu Leu Ala Arg Leu Gly Leu Ala Glu Gly Thr Ser
            740             745             750

Pro Phe Ile Lys Leu Ser Asp Pro Gly Val Gly Leu Gly Ala Leu Ser
        755             760             765

Arg Glu Glu Arg Val Glu Arg Ile Pro Trp Leu Ala Pro Glu Cys Leu
    770             775             780

Pro Gly Gly Ala Asn Ser Leu Ser Thr Ala Met Asp Lys Trp Gly Phe
785             790             795             800

Gly Ala Thr Leu Leu Glu Ile Cys Phe Asp Gly Glu Ala Pro Leu Gln
                805             810             815

Ser Arg Ser Pro Ser Glu Lys Glu His Phe Tyr Gln Arg Gln His Arg
            820             825             830

Leu Pro Glu Pro Ser Cys Pro Gln Leu Ala Thr Leu Thr Ser Gln Cys
        835             840             845

Leu Thr Tyr Glu Pro Thr Gln Arg Pro Ser Phe Arg Thr Ile Leu Arg
    850             855             860

Asp Leu Thr Arg Val Gln Pro His Asn Leu Ala Asp Val Leu Thr Val
865             870             875             880

Asn Arg Asp Ser Pro Ala Val Gly Pro Thr Thr Phe His Lys Arg Tyr
                885             890             895

Leu Lys Lys Ile Arg Asp Leu Gly Glu Gly His Phe Gly Lys Val Ser
            900             905             910

Leu Tyr Cys Tyr Asp Pro Thr Asn Asp Gly Thr Gly Glu Met Val Ala
        915             920             925

Val Lys Ala Leu Lys Ala Asp Cys Gly Pro Gln His Arg Ser Gly Trp
    930             935             940

Lys Gln Glu Ile Asp Ile Leu Arg Thr Leu Tyr His Glu His Ile Ile
945             950             955             960

Lys Tyr Lys Gly Cys Cys Glu Asp Gln Gly Glu Lys Ser Leu Gln Leu
                965             970             975

Val Met Glu Tyr Val Pro Leu Gly Ser Leu Arg Asp Tyr Leu Pro Arg
            980             985             990
```

His Ser Ile Gly Leu Ala Gln Leu Leu Leu Phe Ala Gln Gln Ile Cys
        995                 1000                1005

Glu Gly Met Ala Tyr Leu His Ala His Asp Tyr Ile His Arg Asp Leu
        1010                1015                1020

Ala Ala Arg Asn Val Leu Leu Asp Asn Asp Arg Leu Val Lys Ile Gly
1025                1030                1035                1040

Asp Phe Gly Leu Ala Lys Ala Val Pro Glu Gly His Glu Tyr Tyr Arg
                1045                1050                1055

Val Arg Glu Asp Gly Asp Ser Pro Val Phe Trp Tyr Ala Pro Glu Cys
        1060                1065                1070

Leu Lys Glu Tyr Lys Phe Tyr Tyr Ala Ser Asp Val Trp Ser Phe Gly
        1075                1080                1085

Val Thr Leu Tyr Glu Leu Leu Thr His Cys Asp Ser Ser Gln Ser Pro
        1090                1095                1100

Pro Thr Lys Phe Leu Glu Leu Ile Gly Ile Ala Gln Gly Gln Met Thr
1105                1110                1115                1120

Val Leu Arg Leu Thr Glu Leu Leu Glu Arg Gly Glu Arg Leu Pro Arg
                1125                1130                1135

Pro Asp Lys Cys Pro Cys Glu Val Tyr His Leu Met Lys Asn Cys Trp
        1140                1145                1150

Glu Thr Glu Ala Ser Phe Arg Pro Thr Phe Glu Asn Leu Ile Pro Ile
        1155                1160                1165

Leu Lys Thr Val His Glu Lys Tyr Gln Gly Gln Ala Pro Ser Val Phe
        1170                1175                1180

Ser Val Cys
1185

( 2 ) INFORMATION FOR SEQ ID NO:14:

( i ) SEQUENCE CHARACTERISTICS:
        ( A ) LENGTH: 1153 amino acids
        ( B ) TYPE: amino acid
        ( C ) STRANDEDNESS: Not Relevant
        ( D ) TOPOLOGY: Not Relevant ( i i ) MOLECULE TYPE: protein ( x i ) SEQUENCE DESCRIPTION: SEQ ID NO:14:

Met Gln Tyr Leu Asn Ile Lys Glu Asp Cys Asn Ala Met Ala Phe Cys
1               5                   10                  15

Ala Lys Met Arg Ser Phe Lys Lys Thr Glu Val Lys Gln Val Val Pro
                20                  25                  30

Glu Pro Gly Val Glu Val Thr Phe Tyr Leu Leu Asp Arg Glu Pro Leu
        35                  40                  45

Arg Leu Gly Ser Gly Glu Tyr Thr Ala Glu Glu Leu Cys Ile Arg Ala
        50                  55                  60

Ala Gln Gly Cys Ser Ile Ser Pro Leu Cys His Asn Leu Phe Ala Leu
65                  70                  75                  80

Tyr Asp Glu Ser Thr Lys Leu Trp Tyr Ala Pro Asn Arg Ile Ile Thr
                85                  90                  95

Val Asp Asp Lys Thr Ser Leu Arg Leu His Tyr Arg Met Arg Phe Tyr
                100                 105                 110

Phe Thr Asn Trp His Gly Thr Asn Asp Asn Glu Gln Ser Val Trp Arg
                115                 120                 125

His Ser Pro Lys Lys Gln Lys Asn Gly Tyr Glu Lys Lys Arg Val Pro
        130                 135                 140

```
Glu Ala Thr Pro Leu Leu Asp Ala Ser Ser Leu Glu Tyr Leu Phe Ala
145                 150                 155                 160

Gln Gly Gln Tyr Asp Leu Ile Lys Phe Leu Ala Pro Ile Arg Asp Pro
                165                 170                 175

Lys Thr Glu Gln Asp Gly His Asp Ile Glu Asn Glu Cys Leu Gly Met
            180                 185                 190

Ala Val Leu Ala Ile Ser His Tyr Ala Met Met Lys Lys Met Gln Leu
        195                 200                 205

Pro Glu Leu Pro Lys Asp Ile Ser Tyr Lys Arg Tyr Ile Pro Glu Thr
    210                 215                 220

Leu Asn Lys Ser Ile Arg Gln Arg Asn Leu Leu Thr Arg Met Arg Ile
225                 230                 235                 240

Asn Asn Val Phe Lys Asp Phe Leu Lys Glu Phe Asn Asn Lys Thr Ile
                245                 250                 255

Cys Asp Ser Ser Val Ser Thr His Asp Leu Lys Val Lys Tyr Leu Ala
            260                 265                 270

Thr Leu Glu Thr Leu Thr Lys His Tyr Gly Ala Glu Ile Phe Glu Thr
        275                 280                 285

Ser Met Leu Leu Ile Ser Ser Glu Asn Glu Leu Ser Arg Cys His Ser
290                 295                 300

Asn Asp Ser Gly Asn Val Leu Tyr Glu Val Met Val Thr Gly Asn Leu
305                 310                 315                 320

Gly Ile Gln Trp Arg Gln Lys Pro Asn Val Val Pro Val Glu Lys Glu
                325                 330                 335

Lys Asn Lys Leu Lys Arg Lys Lys Leu Glu Tyr Asn Lys His Lys Lys
            340                 345                 350

Asp Asp Glu Arg Asn Lys Leu Arg Glu Glu Trp Asn Asn Phe Ser Tyr
        355                 360                 365

Phe Pro Glu Ile Thr His Ile Val Ile Lys Glu Ser Val Val Ser Ile
    370                 375                 380

Asn Lys Gln Asp Asn Lys Asn Met Glu Leu Lys Leu Ser Ser Arg Glu
385                 390                 395                 400

Glu Ala Leu Ser Phe Val Ser Leu Val Asp Gly Tyr Phe Arg Leu Thr
                405                 410                 415

Ala Asp Ala His His Tyr Leu Cys Thr Asp Val Ala Pro Pro Leu Ile
            420                 425                 430

Val His Asn Ile Gln Asn Gly Cys His Gly Pro Ile Cys Thr Glu Tyr
        435                 440                 445

Ala Ile Asn Lys Leu Arg Gln Glu Gly Ser Glu Glu Gly Met Tyr Val
    450                 455                 460

Leu Arg Trp Ser Cys Thr Asp Phe Asp Asn Ile Leu Met Thr Val Thr
465                 470                 475                 480

Cys Gly Glu Lys Ser Glu Val Leu Gly Gly Gln Lys Gln Phe Asn Phe
                485                 490                 495

Gln Ile Glu Val Gln Lys Phe Arg Tyr Ser Leu His Gly Ser Met Asp
            500                 505                 510

His Phe Pro Ser Leu Arg Asp Leu Met Asn His Leu Lys Lys Gln Ile
        515                 520                 525

Leu Arg Thr Asp Asn Ile Ser Phe Val Leu Lys Arg Cys Cys Gln Pro
    530                 535                 540

Lys Pro Arg Glu Ile Ser Asn Leu Leu Val Ala Thr Lys Lys Ala Gln
545                 550                 555                 560

Glu Trp Gln Pro Val Tyr Ser Met Ser Gln Leu Ser Phe Asp Arg Ile
                565                 570                 575
```

```
Leu Lys Lys Asp Ile Ile Gln Gly Glu His Leu Gly Arg Gly Thr Arg
            580             585                 590

Thr His Ile Tyr Ser Gly Thr Leu Leu Asp Tyr Lys Asp Glu Glu Gly
        595             600             605

Ile Ala Glu Glu Lys Lys Ile Lys Val Ile Leu Lys Val Leu Asp Pro
    610             615             620

Ser His Arg Asp Ile Ser Leu Ala Phe Phe Glu Ala Ala Ser Met Met
625             630             635                     640

Arg Gln Val Ser His Lys His Ile Val Tyr Leu Tyr Gly Val Cys Val
            645             650             655

Arg Asp Val Glu Asn Ile Met Val Glu Glu Phe Val Glu Gly Gly Pro
            660             665             670

Leu Asp Leu Phe Met His Arg Lys Ser Asp Ala Leu Thr Thr Pro Trp
        675             680             685

Lys Phe Lys Val Ala Lys Gln Leu Ala Ser Ala Leu Ser Tyr Leu Glu
    690             695             700

Asp Lys Asp Leu Val His Gly Asn Val Cys Thr Lys Asn Leu Leu Leu
705             710             715                     720

Ala Arg Glu Gly Ile Asp Ser Asp Ile Gly Pro Phe Ile Lys Leu Ser
                725             730             735

Asp Pro Gly Ile Pro Val Ser Val Leu Thr Arg Gln Glu Cys Ile Glu
            740             745             750

Arg Ile Pro Trp Ile Ala Pro Glu Cys Val Glu Asp Ser Lys Asn Leu
        755             760             765

Ser Val Ala Ala Asp Lys Trp Ser Phe Gly Thr Thr Leu Trp Glu Ile
    770             775             780

Cys Tyr Asn Gly Glu Ile Pro Leu Lys Asp Lys Thr Leu Ile Glu Lys
785             790             795                     800

Glu Arg Phe Tyr Glu Ser Arg Cys Arg Pro Val Thr Pro Ser Cys Lys
            805             810             815

Glu Leu Ala Asp Leu Met Thr Arg Cys Met Asn Tyr Asp Pro Asn Gln
            820             825             830

Arg Pro Phe Phe Arg Ala Ile Met Arg Asp Ile Asn Lys Leu Glu Glu
        835             840             845

Gln Asn Pro Asp Ile Val Ser Glu Lys Gln Pro Thr Thr Glu Val Asp
850             855             860

Pro Thr His Phe Glu Lys Arg Phe Leu Lys Lys Arg Ile Arg Asp Leu
865             870             875                     880

Gly Glu Gly His Phe Gly Lys Val Glu Leu Cys Arg Tyr Asp Pro Glu
            885             890             895

Cys Asp Asn Thr Gly Glu Gln Val Ala Val Lys Ser Leu Lys Pro Glu
            900             905             910

Ser Gly Gly Asn His Ile Ala Asp Leu Lys Lys Glu Ile Glu Ile Leu
    915             920             925

Arg Asn Leu Tyr His Glu Asn Ile Val Lys Tyr Lys Gly Ile Cys Met
    930             935             940

Glu Asp Gly Gly Asn Gly Ile Lys Leu Ile Met Glu Phe Leu Pro Ser
945             950             955                     960

Gly Ser Leu Lys Glu Tyr Leu Pro Lys Asn Lys Asn Lys Ile Asn Leu
            965             970             975

Lys Gln Gln Leu Lys Tyr Ala Ile Gln Ile Cys Lys Gly Met Asp Tyr
        980             985             990

Leu Gly Ser Arg Gln Tyr Val His Arg Asp Leu Ala Ala Arg Asn Val
```

-continued

| | 995 | | | | | 1000 | | | | | | 1005 | | | |
|---|---|---|---|---|---|---|---|---|---|---|---|---|---|---|---|
| Leu | Val | Glu | Ser | Glu | His | Gln | Val | Lys | Ile | Gly | Asp | Phe | Gly | Leu | Thr |
| | 1010 | | | | | 1015 | | | | | 1020 | | | | |
| Lys | Ala | Ile | Glu | Thr | Asp | Lys | Glu | Tyr | Tyr | Thr | Val | Lys | Asp | Asp | Arg |
| 1025 | | | | | 1030 | | | | | 1035 | | | | | 1040 |
| Asp | Ser | Pro | Val | Phe | Trp | Tyr | Ala | Pro | Glu | Cys | Leu | Ile | Gln | Cys | Lys |
| | | | | 1045 | | | | | 1050 | | | | | 1055 | |
| Phe | Tyr | Ile | Ala | Ser | Asp | Val | Trp | Ser | Phe | Gly | Val | Thr | Leu | His | Glu |
| | | | | 1060 | | | | | 1065 | | | | | 1070 | |
| Leu | Leu | Thr | Tyr | Cys | Asp | Ser | Asp | Phe | Ser | Pro | Met | Ala | Leu | Phe | Leu |
| | | 1075 | | | | | 1080 | | | | | 1085 | | | |
| Lys | Met | Ile | Gly | Pro | Thr | His | Gly | Gln | Met | Thr | Val | Thr | Arg | Leu | Val |
| | 1090 | | | | | 1095 | | | | | 1100 | | | | |
| Asn | Thr | Leu | Lys | Glu | Gly | Lys | Arg | Leu | Pro | Cys | Pro | Pro | Asn | Cys | Pro |
| 1105 | | | | | 1110 | | | | | 1115 | | | | | 1120 |
| Asp | Glu | Val | Tyr | Gln | Leu | Met | Arg | Lys | Cys | Trp | Glu | Phe | Gln | Pro | Ser |
| | | | | 1125 | | | | | 1130 | | | | | 1135 | |
| Asn | Arg | Thr | Thr | Phe | Gln | Asn | Leu | Ile | Glu | Gly | Phe | Glu | Ala | Leu | Leu |
| | | | 1140 | | | | | 1145 | | | | | 1150 | | |
| Lys | | | | | | | | | | | | | | | |